United States Patent
Moon et al.

(10) Patent No.: US 10,854,824 B2
(45) Date of Patent: Dec. 1, 2020

(54) ORGANIC ELECTROLUMINESCENT COMPOUND, ORGANIC ELECTROLUMINESCENT MATERIAL AND ORGANIC ELECTROLUMINESCENT DEVICE COMPRISING THE SAME

(71) Applicant: Rohm and Haas Electronic Materials Korea Ltd., Cheonan (KR)

(72) Inventors: Doo-Hyeon Moon, Hwaseong (KR); Jeong-Eun Yang, Suwon (KR)

(73) Assignee: Rohm and Haas Electronic Materials Korea Ltd., Seoul (KR)

( * ) Notice: Subject to any disclaimer, the term of this patent is extended or adjusted under 35 U.S.C. 154(b) by 383 days.

(21) Appl. No.: 15/775,136

(22) PCT Filed: Nov. 18, 2016

(86) PCT No.: PCT/KR2016/013314
§ 371 (c)(1),
(2) Date: May 10, 2018

(87) PCT Pub. No.: WO2017/086729
PCT Pub. Date: May 26, 2017

(65) Prior Publication Data
US 2018/0375031 A1    Dec. 27, 2018

(30) Foreign Application Priority Data

Nov. 20, 2015   (KR) .................. 10-2015-0162980
Nov. 17, 2016   (KR) .................. 10-2016-0153209

(51) Int. Cl.
*H01L 51/00*    (2006.01)
*C07D 487/04*    (2006.01)
*C09K 11/06*    (2006.01)
*H01L 51/50*    (2006.01)

(52) U.S. Cl.
CPC ........ *H01L 51/0072* (2013.01); *C07D 487/04* (2013.01); *C09K 11/06* (2013.01); *H01L 51/006* (2013.01); *H01L 51/0052* (2013.01); *H01L 51/0059* (2013.01); *H01L 51/0061* (2013.01); *H01L 51/0065* (2013.01); *H01L 51/0067* (2013.01); *H01L 51/0071* (2013.01); *H01L 51/0073* (2013.01); *H01L 51/0074* (2013.01); *C09K 2211/1018* (2013.01); *H01L 51/0085* (2013.01); *H01L 51/508* (2013.01); *H01L 51/5016* (2013.01); *H01L 51/5076* (2013.01); *H01L 51/5096* (2013.01); *H01L 2251/5384* (2013.01)

(58) Field of Classification Search
CPC ............ H01L 51/0071; H01L 51/0072; H01L 51/0057
See application file for complete search history.

(56) References Cited

U.S. PATENT DOCUMENTS

| | | | | |
|---|---|---|---|---|
| 6,632,256 B1 * | 10/2003 | Ishizaki | ............ | H01M 2/0212 29/623.5 |
| 2012/0077091 A1 * | 3/2012 | Lee | ............ | H01G 11/06 429/303 |
| 2013/0012700 A1 * | 1/2013 | Parham | ............ | C07D 471/16 540/492 |
| 2016/0163998 A1 * | 6/2016 | Saito | ............ | C07D 487/06 257/40 |
| 2017/0301867 A1 * | 10/2017 | Kim | ............ | C07D 487/22 |
| 2020/0058881 A1 * | 2/2020 | Groarke | ............ | H01L 51/0074 |

FOREIGN PATENT DOCUMENTS

KR    2015-0070827 A    6/2015

* cited by examiner

Primary Examiner — Matthew E. Hoban
(74) Attorney, Agent, or Firm — S. Matthew Cairns

(57) ABSTRACT

The present disclosure relates to an organic electroluminescent compound, an organic electroluminescent material, and an organic electroluminescent device comprising the same. By using the organic electroluminescent compound of the present disclosure, it is possible to provide an organic electroluminescent device having low driving voltage, and/or excellent current and/or power efficiencies.

10 Claims, No Drawings

ORGANIC ELECTROLUMINESCENT COMPOUND, ORGANIC ELECTROLUMINESCENT MATERIAL AND ORGANIC ELECTROLUMINESCENT DEVICE COMPRISING THE SAME

TECHNICAL FIELD

The present disclosure relates to an organic electroluminescent compound, an organic electroluminescent material and an organic electroluminescent device comprising the same.

BACKGROUND ART

Among display devices, an electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device is light-emitting materials. Until now, fluorescent materials have been widely used as the light-emitting material. However, in view of electroluminescent mechanisms, since phosphorescent light-emitting materials theoretically enhance luminous efficiency by four (4) times compared to fluorescent light-emitting materials, phosphorescent light-emitting materials have been widely researched. Iridium(III) complexes have been widely known as phosphorescent light-emitting materials, including bis(2-(2'-benzothienyl)-pyridinato-N,C-3') iridium(acetylacetonate) [(acac)Ir(btp)$_2$], tris(2-phenylpyridine)iridium [Ir(ppy)$_3$] and bis(4,6-difluorophenylpyridinato-N,C2)picolinato iridium (Firpic) as red-, green- and blue-emitting materials, respectively.

In conventional technology, 4,4'-N,N'-dicarbazol-biphenyl (CBP) is the most widely known host material for phosphorescent materials. Recently, Pioneer (Japan) et al., developed a high performance organic electroluminescent device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the organic electroluminescent device is given by [(π/voltage)× current efficiency], and the power efficiency is inversely proportional to the voltage. Although the organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the organic electroluminescent device is short, and luminous efficiency is still necessary to improve. Accordingly, the materials constituting the organic layer in the device, in particular a host constituting the light-emitting material, must be selected appropriately in order to realize the excellent characteristics of the organic EL device.

To improve efficiencies and stability, the organic electroluminescent device may consist of a multi-layered structure in which a hole injection layer, a hole transport layer, a light-emitting layer, an electron transport layer, an electron injection layer, etc., are comprised. In the structure, a compound comprised for the hole transport layer is important to enhance characteristics of the device, such as efficiency for transporting holes to the light-emitting layer, luminous efficiency, and lifespan.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4"-tris(3-methylphenylphenylamino)triphenylamine (MTDATA), etc., were used as hole injection and transport materials for an organic electroluminescent device. However, the organic electroluminescent device using these materials is problematic in lowering quantum efficiency and lifespan. It is due to thermal stress occuring between an anode and a hole injection layer, when the organic electroluminescent device is driven under high current. Thermal stress significantly reduces the lifespan of the device. Furthermore, since the organic material used for the hole injection layer has very high hole mobility, the hole-electron charge balance may be broken and quantum yield (cd/A) may decrease. Thus, development of a hole transport layer for improving the durability of an organic electroluminescent device is still required.

Meanwhile, in order to improve the efficiency of an organic electroluminescent device, optimizing the device is required as well as developing an organic electroluminescent material comprised in the device. Thus, studies have been made to improve the efficiency of an organic electroluminescent device by inserting an electron buffer layer between a light-emitting layer and an electron injection layer. The electron buffer layer is equipped to improve a problem of light-emitting luminance reduction which may occur due to the change of current properties in the device when the device is exposed to a high temperature during a process of producing panels. Thus, the properties of the compounds comprised for the electron buffer layer are important. In addition, the compound used for the electron buffer layer is desirable to perform a role of controlling an electron injection by the electron withdrawing characteristics and the electron affinity LUMO (lowest unoccupied molecular orbital) energy level, and thus may perform a role to improve the efficiency of the organic electroluminescent device. Thus, the development of an electron buffer material constituting an electron buffer layer is required in order to improve deterioration characteristics according to temperature of an organic electroluminescent device and improve the efficiency by controlling electron injection.

Korean Patent Application Laid-Open No. 2015-0070827 discloses an organic electroluminescent device comprising a compound having a backbone in which arylamine moieties are respectively bonded to carbon positions 2 and 3 of a carbazole moiety and fused with each other to form an 8-membered ring. However, the above reference fails to disclose a compound having a structure in which two aryls bonded directly to carbon position 1 and the nitrogen atom of a carbazole moiety form an 8-membered ring via a nitrogen atom, an oxygen atom or a sulfur atom as a linker.

DISCLOSURE OF THE INVENTION

Problems to be Solved

The object of the present disclosure is firstly, to provide an organic electroluminescent compound effective to produce an organic electroluminescent device having low driving voltage and/or excellent luminous efficiency such as current and/or power efficiencies, secondly, to provide an organic electroluminescent material comprising the organic electroluminescent compound, and thirdly, to provide an organic electroluminescent device comprising the organic electroluminescent compound.

Solution to Problems

As a result of intensive studies to solve the technical problem above, the present inventors found that the above objective can be achieved by an organic electroluminescent compound represented by the following formula 1:

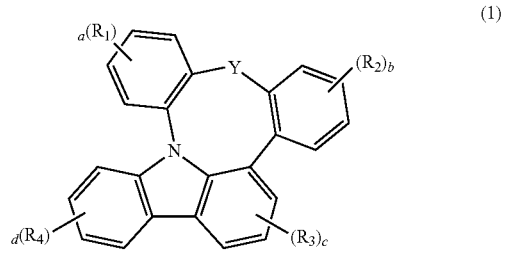

(1)

wherein

Y represents S, O or $NR_5$;

$R_1$ to $R_5$, each independently, represent deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to adjacent $R_1$ to $R_5$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;

the heteroaryl contains at least one heteroatom selected from B, N, O, S, Si, and P;

a, b and d, each independently, represent an integer of 0 to 4, c represents an integer of 0 to 3; where if a to d, each independently, represent an integer of 2 or more, each of $R_1$ to $R_4$ may be the same or different; and with the proviso, when Y represents $NR_5$ and a represents 2, two $R_1$ are not fused with the aryl ring to which they are attached to form a carbazole ring.

The organic electroluminescent compound has the fused ring structure of an 8-membered ring based on a carbazole, and has a relatively high glass transition temperature as compared to low molecular weight. The compound of the present disclosure having a high glass transition temperature is excellent in thermal stability and can have morphological stability even at high temperatures during device operation. In addition, the compound of the present disclosure may be easily substituted due to the structural characteristics, and may be applied to various layers depending on the substituents.

Effects of the Invention

The organic electroluminescent compound of the present disclosure can provide an organic electroluminescent device having low driving voltage and/or excellent current and/or power efficiencies.

EMBODIMENTS OF THE INVENTION

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an organic electroluminescent device, and may be comprised of any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised of any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The compound represented by formula 1 will be described in detail as follows.

In formula 1, Y represents S, O or $NR_5$.

In formula 1, $R_1$ to $R_5$, each independently, represent deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to adjacent $R_1$ to $R_5$ to form a substituted or unsubstituted, mono- or polycyclic, (C3-C30) alicyclic or aromatic ring, or a combination thereof, whose carbon atom(s) may be replaced with at least one heteroatom selected from nitrogen, oxygen, and sulfur. With the proviso, when Y represents $NR_5$ and a represents 2, two $R_1$ are not fused with the aryl ring to which they are attached to form a carbazole ring.

Preferably, $R_1$ to $R_4$, each independently, represent a substituted or unsubstituted (C6-C25)aryl, a substituted or unsubstituted (5- to 25-membered)heteroaryl, or a substituted or unsubstituted di(C6-C25)arylamino; or are linked to adjacent $R_1$ to $R_4$, respectively, to form a substituted or unsubstituted, mono- or polycyclic, (C5-C25) aromatic ring, whose carbon atom(s) may be replaced with at least one heteroatom selected from nitrogen, oxygen, and sulfur. More preferably, $R_1$ to $R_4$, each independently, represent a substituted or unsubstituted (C6-C20)aryl, a substituted or unsubstituted (5- to 20-membered)heteroaryl, or an unsubstituted di(C6-C25)arylamino; or are linked to adjacent $R_1$ to $R_4$, respectively, to form an unsubstituted, mono- or polycyclic, (C5-C20) aromatic ring. For example, $R_1$ to $R_4$, each independently, represent a substituted or unsubstituted phenyl, an unsubstituted biphenyl, an unsubstituted terphenyl, a carbazolyl substituted with a phenyl, an unsubstituted dibenzofuranyl, an unsubstituted dibenzothiophenyl, a quinoxalinyl substituted with a phenyl, a quinazolinyl substituted with a biphenyl, a pyridyl substituted with a dibiphenylamino, a triazinyl substituted with a diphenyl, or an unsubstituted dibiphenylamino; or are linked to adjacent $R_1$ to $R_4$, respectively, to form a benzene ring.

Preferably, $R_5$ represents a substituted or unsubstituted (C6-C30)aryl, or a substituted or unsubstituted (3- to 25-membered)heteroaryl. More preferably, $R_5$ represents a substituted or unsubstituted (C6-C30)aryl, or a substituted or unsubstituted (5- to 18-membered)heteroaryl. For example, $R_5$ represents a substituted or unsubstituted phenyl, an unsubstituted naphthylphenyl, an unsubstituted naphthyl, a biphenyl unsubstituted or substituted with a dibiphenylamino, an unsubstituted terphenyl, an unsubstituted quaterphenyl, an unsubstituted pentaphenyl, a fluorenyl substituted with a methyl or a phenyl, a carbazolyl substituted with a phenyl, an unsubstituted dibenzofuranyl, an unsubstituted dibenzothiophenyl, a triazinyl substituted with at least one phenyl, a quinoxalinyl substituted with a phenyl, a quinazolinyl substituted with a biphenyl, or a pyridyl substituted with a dibiphenylamino.

In formula 1, the heteroaryl contains at least one heteroatom selected from B, N, O, S, Si, and P, and preferably, at least one heteroatom selected from N, O and S.

In formula 1, a, b and d, each independently, represent an integer of 0 to 4, c represents an integer of 0 to 3; where if a to d, each independently, represent an integer of 2 or more, each of $R_1$ to $R_4$ may be the same or different. Preferably, a to d, each independently, represent an integer of 0 to 2.

The organic electroluminescent compound represented by formula 1 may be represented by any one of the following formulas 2 to 4:

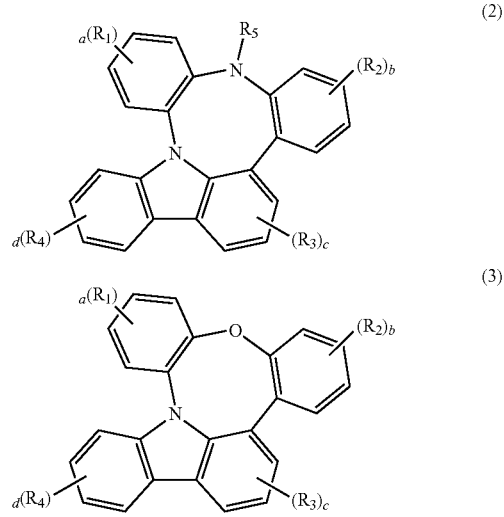

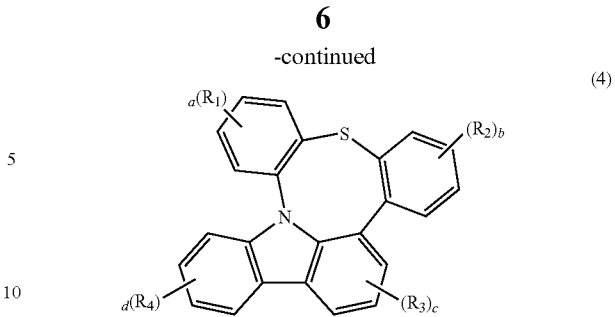

wherein, $R_1$ to $R_5$, and a to d are as defined in formula 1.

In formula 2, when a represents 2, two $R_1$ are not fused with the aryl ring to which they are attached to form a carbazole ring.

Herein, the term "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. The term "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. The term "(3- to 7-membered)heterocycloalkyl" is a cycloalkyl having 3 to 7, preferably 5 to 7, ring backbone atoms, including at least one heteroatom selected from B, N, O, S, Si, and P, preferably O, S, and N, and includes tetrahydrofuran, pyrrolidine, thiolan, tetrahydropyran, etc. The term "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may comprise a spiro structure. The above aryl(ene) may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered)heteroaryl(ene)" is an aryl having 3 to 30 ring backbone atoms, including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); may comprise a spiro structure; and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted (C1-C30)alkyl, the substituted (C2-C30)alkenyl, the substituted (C2-C30)alkynyl, the substituted (C6-C30) aryl(ene), the substituted (3- to 30-membered)heteroaryl (ene), the substituted (C3-C30)cycloalkyl, the substituted (C3-C30)cycloalkenyl, the substituted (3- to 7-membered) heterocycloalkyl, the substituted (C1-C30)alkoxy, the substituted tri(C1-C30)alkylsilyl, the substituted di(C1-C30) alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic or aromatic ring, or the combination thereof, in $R_1$ to $R_8$, Ma, La and Xa to Xi, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30)aryl; a (C6-C30)aryl unsubstituted or substituted with a (5- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30) alkyl(C6-C30)arylboronyl; a (C6-C30)aryl(C1-C30)alkyl; and a (C1-C30)alkyl(C6-C30)aryl; preferably, are at least one selected from the group consisting of a (C1-C20)alkyl, a (5- to 20-membered)heteroaryl unsubstituted or substituted with a (C6-C20)aryl, a substituted or unsubstituted (C6-C20)aryl, and a di(C6-C20)arylamino unsubstituted or substituted with a (C1-C20)alkyl; more preferably, are at least one selected from the group consisting of a (C1-C10) alkyl, a (6- to 18-membered)heteroaryl unsubstituted or substituted with a (C6-C10)aryl, a substituted or unsubstituted (C6-C18)aryl, and a di(C6-C18)arylamino unsubstituted or substituted with a (C1-C10)alkyl; and for example, may be at least one selected from the group consisting of a methyl; a phenyl unsubstituted or substituted with a dibenzothiophenyl, a tert-butyl or a cyano; an unsubstituted biphenyl; an unsubstituted terphenyl; an unsubstituted naphthyl; a quinoxalinyl substituted with a phenyl; a triazinyl substituted with at least one phenyl; a pyrimidinyl substituted with at least one phenyl; an unsubstituted dibenzothiophenyl; a carbazolyl substituted with a phenyl; a dibiphenylamino; a phenylbiphenylamino; and a fluorenylbiphenylamino substituted with a dimethyl.

The organic electroluminescent compound represented by formula 1 includes the following compounds, but is not limited thereto:

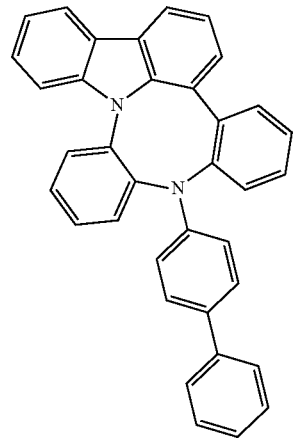

C-1

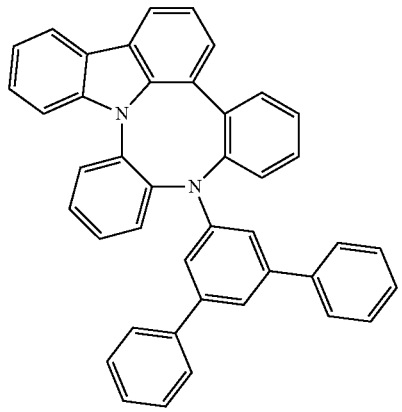

C-2

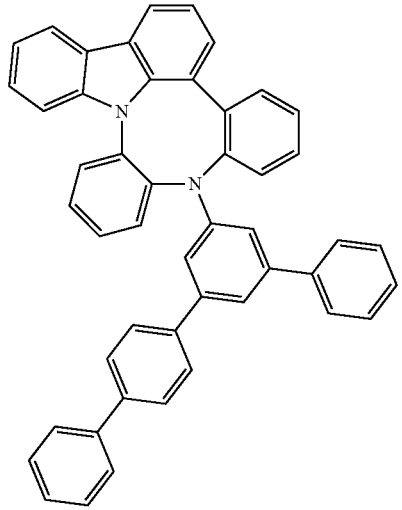

C-3

C-4
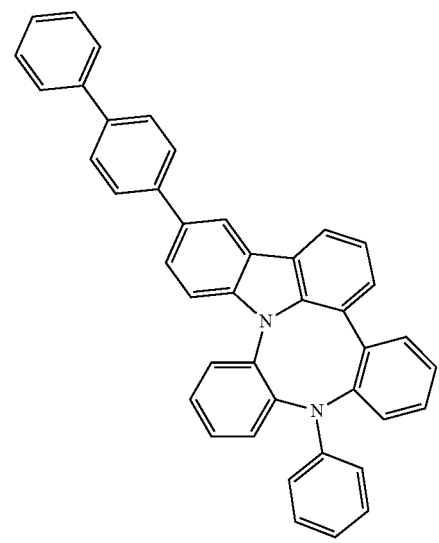
C-5
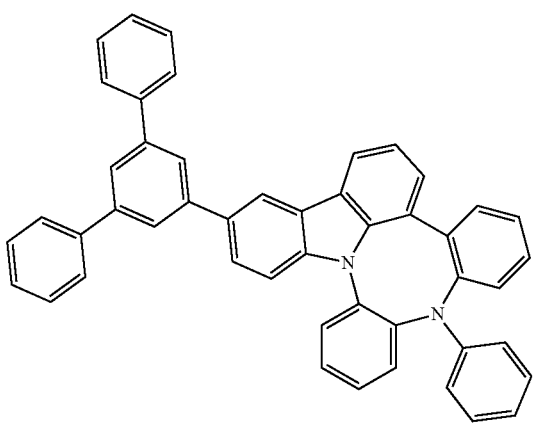
C-6
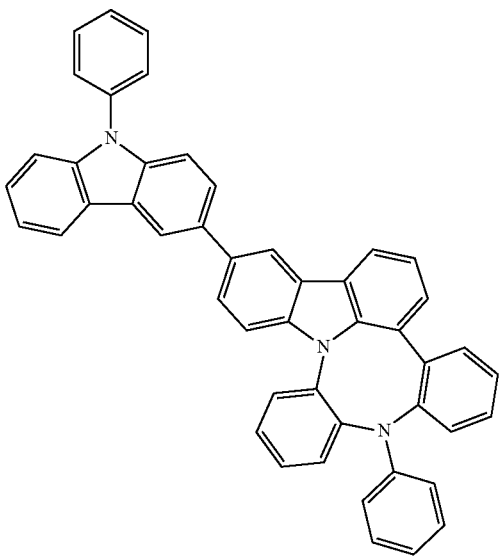
C-7
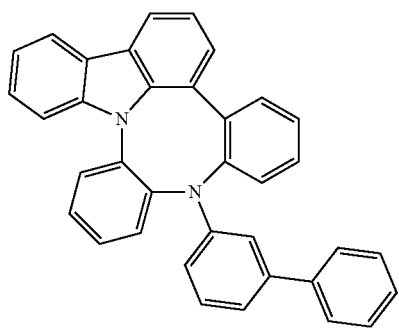
C-8
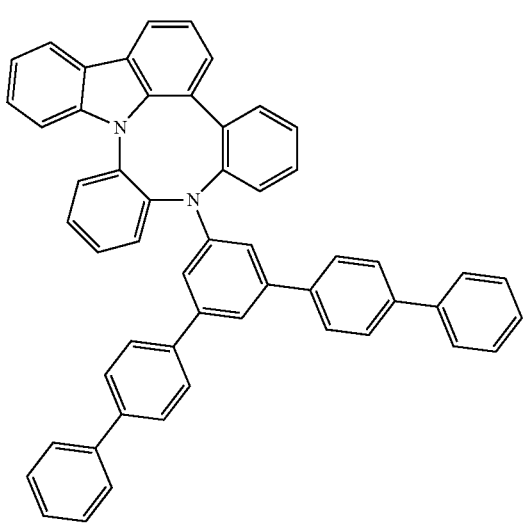
C-9
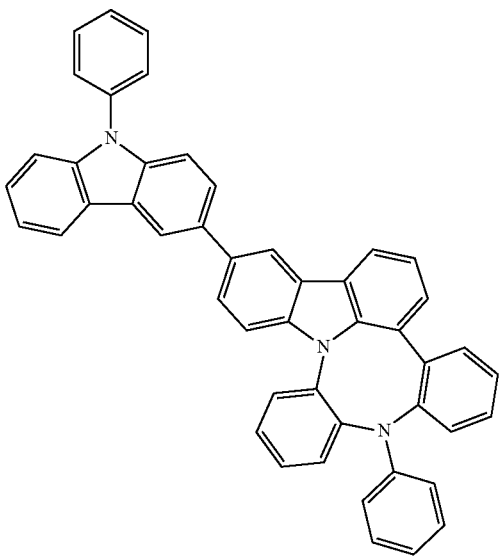

C-10
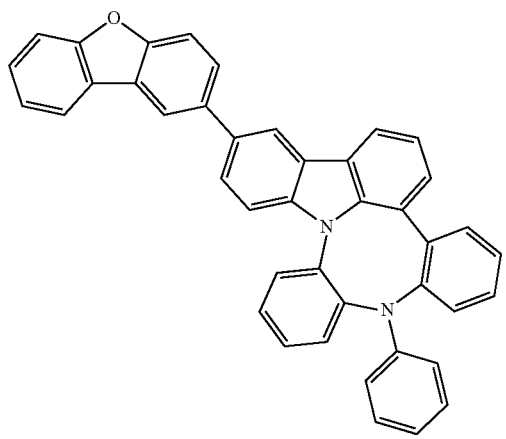
C-13
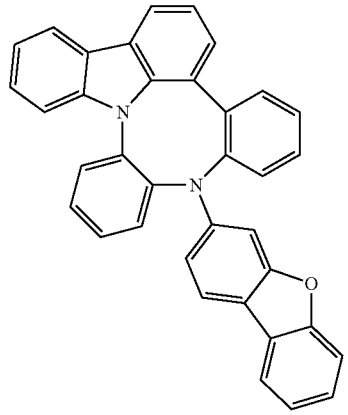
C-11
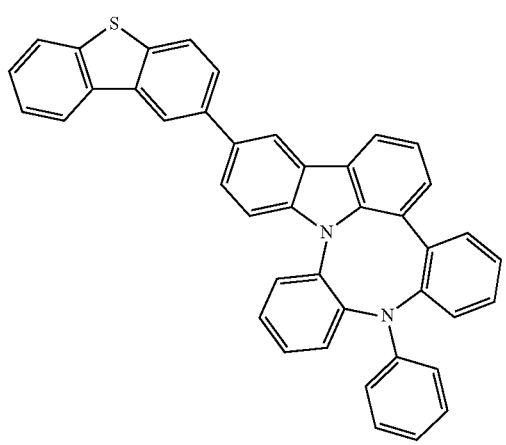
C-14
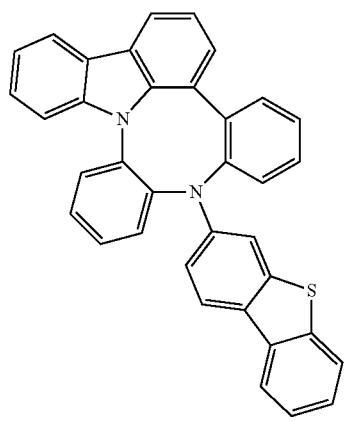
C-12
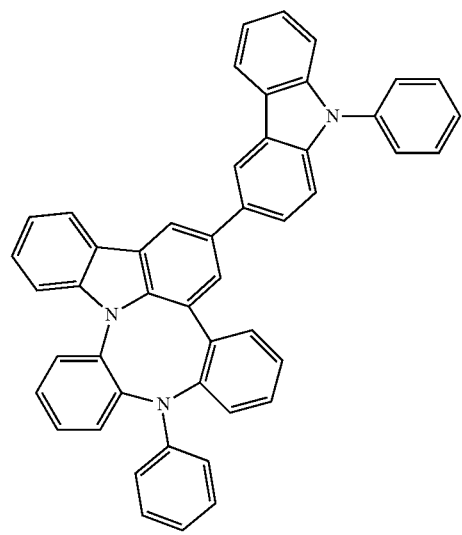
C-15
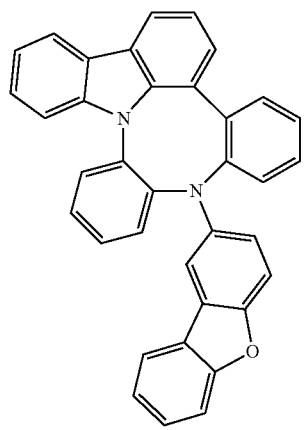

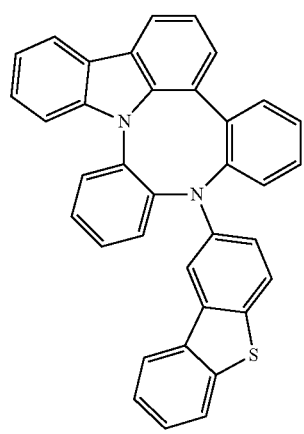
C-16
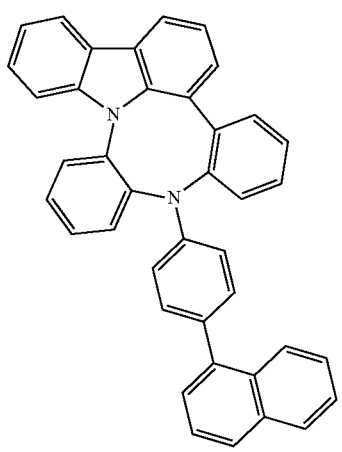
C-19
C-17
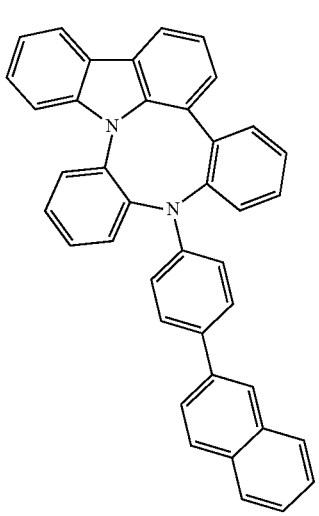
C-20
C-18
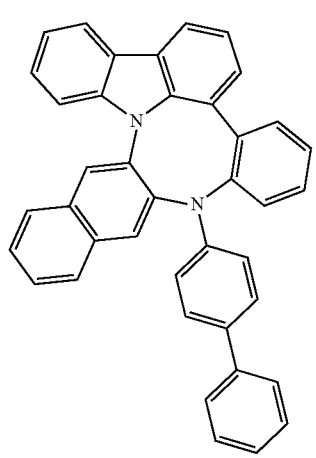
C-21

-continued
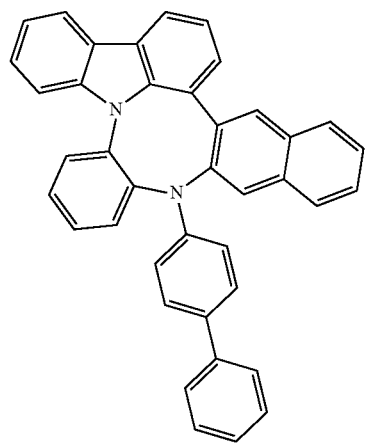
C-22
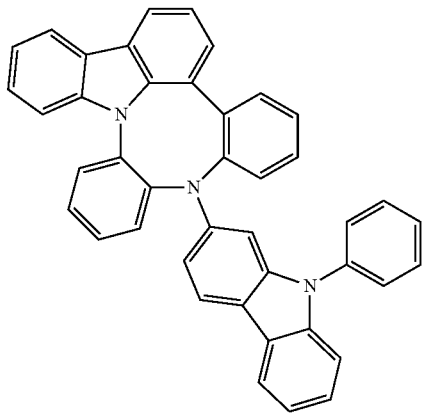
C-25
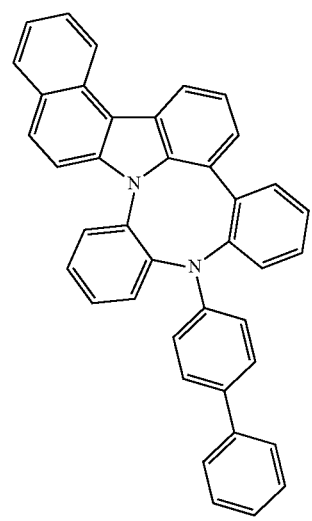
C-23
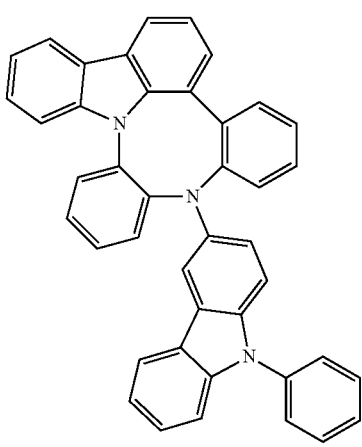
C-26
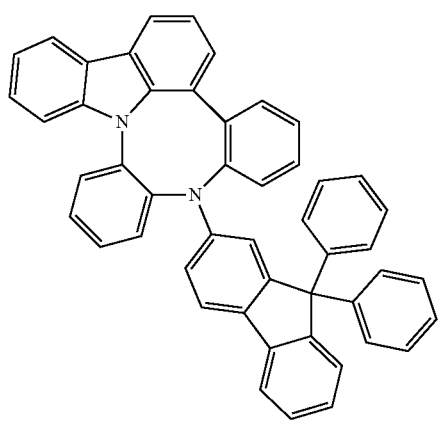
C-24
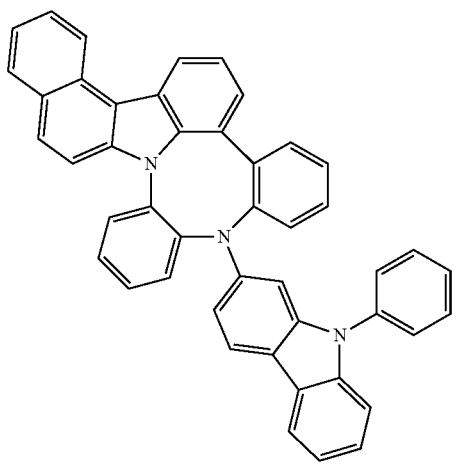
C-27

C-28
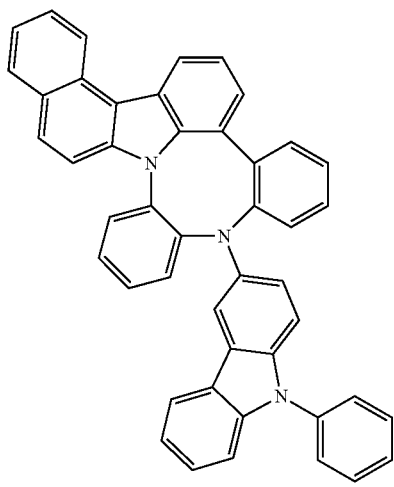
C-31
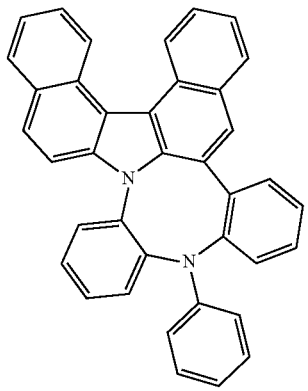
C-29
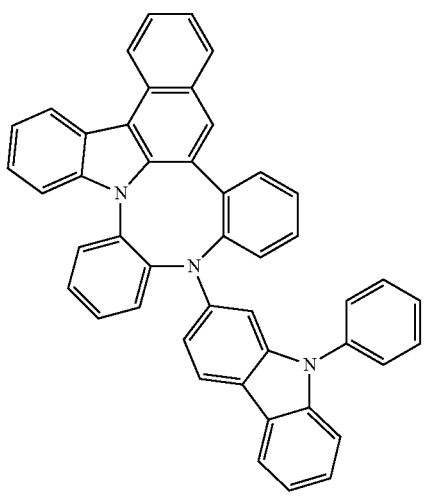
C-32
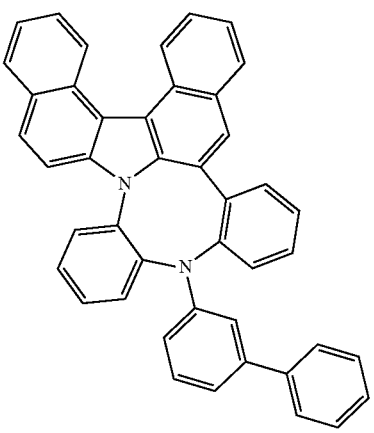
C-30
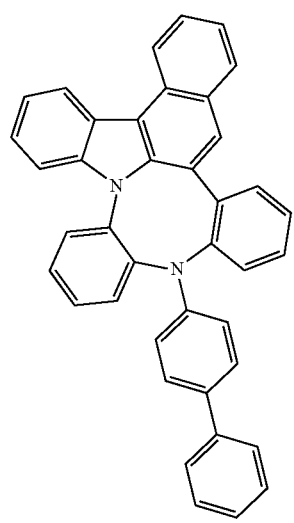
C-33
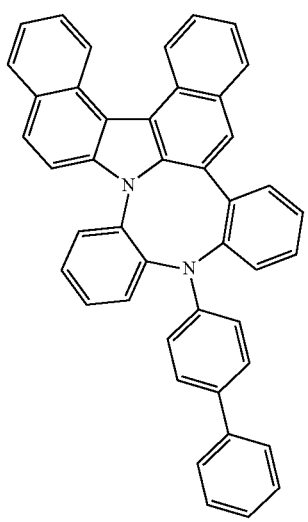

-continued
C-34
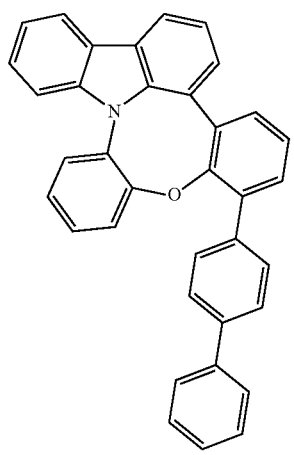
C-35
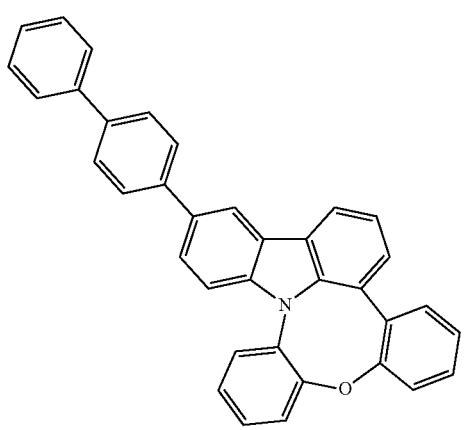
C-36
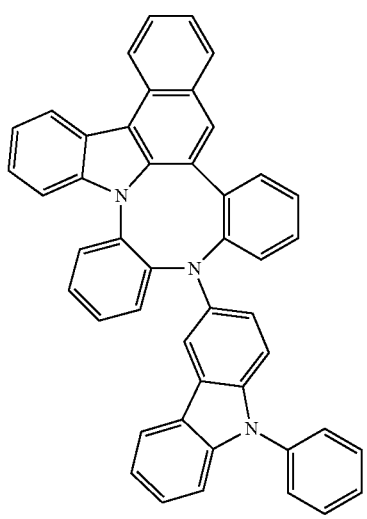
-continued
C-37
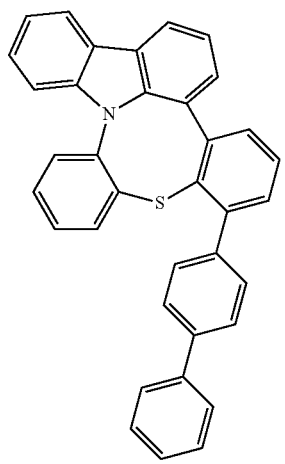
C-38
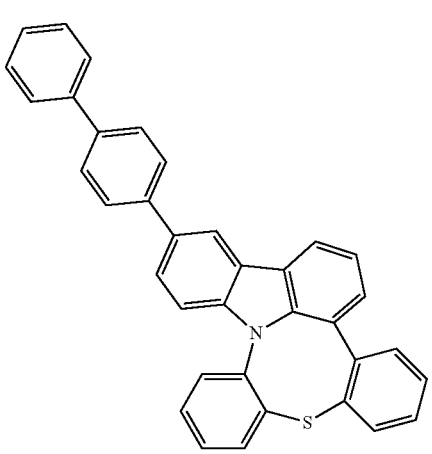
C-39
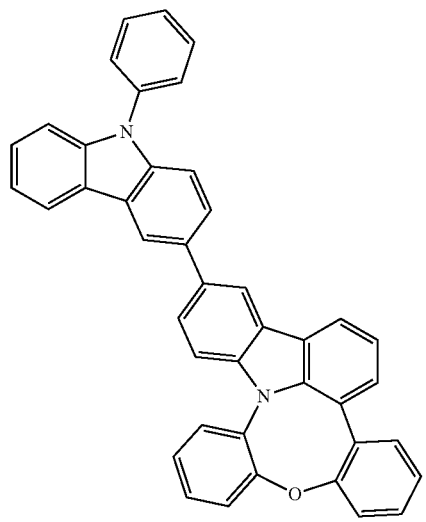

C-40 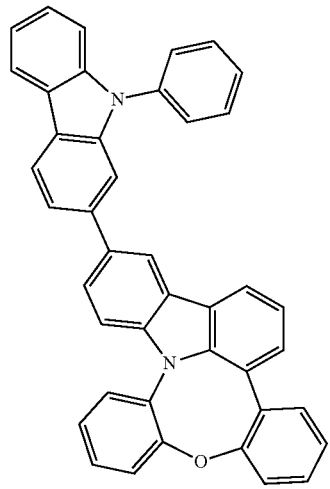
C-41 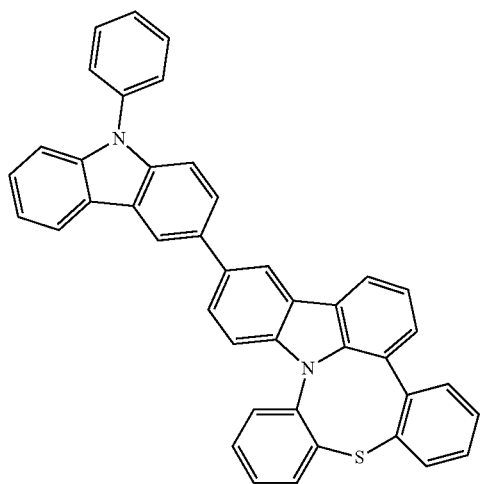
C-42 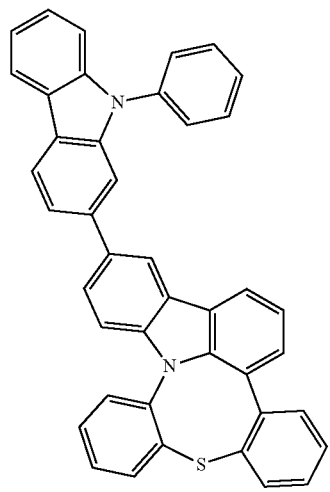
C-43 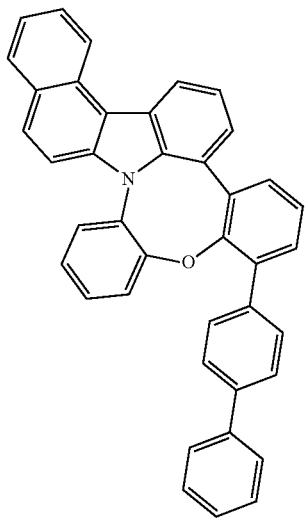
C-44 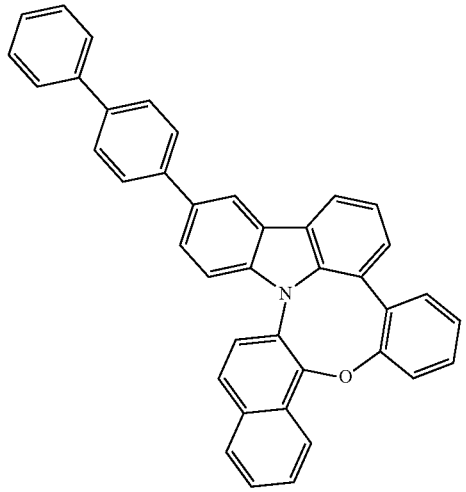
C-45 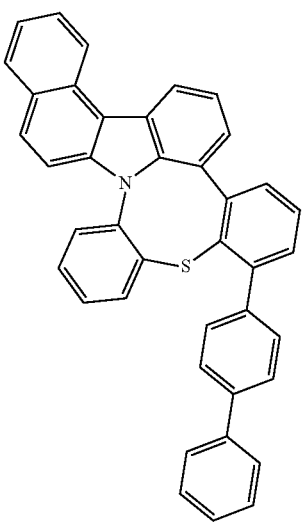

C-46
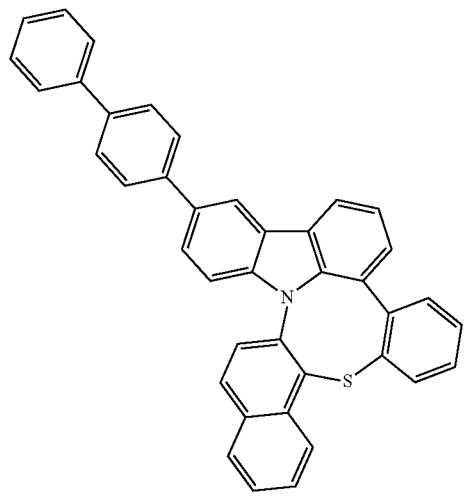
C-47
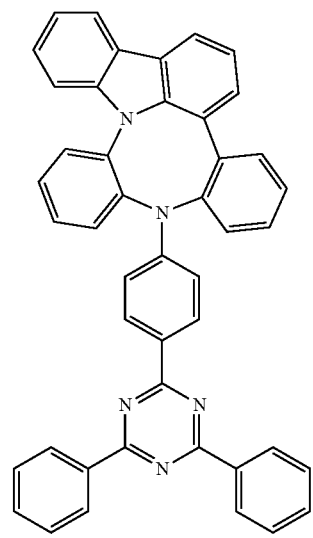
C-48
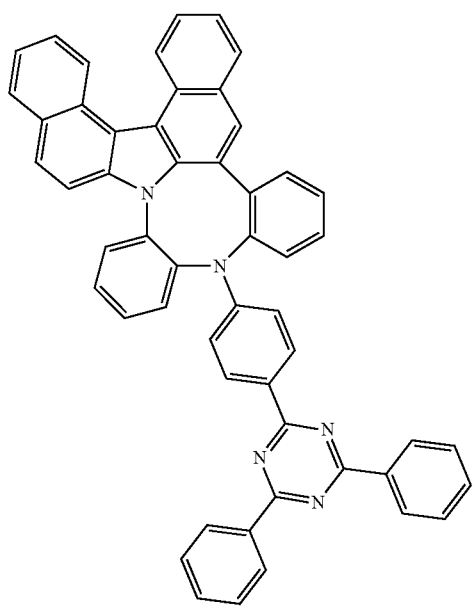
C-49
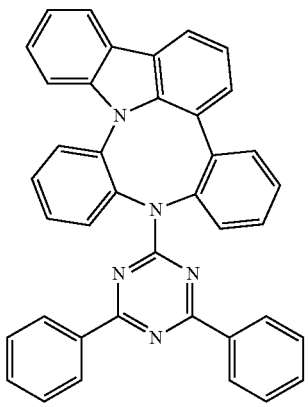
C-50
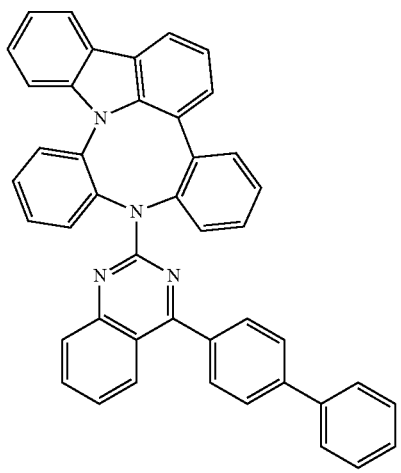
C-51
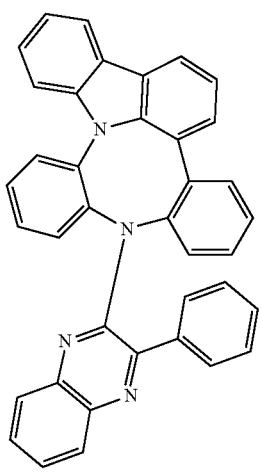

C-52
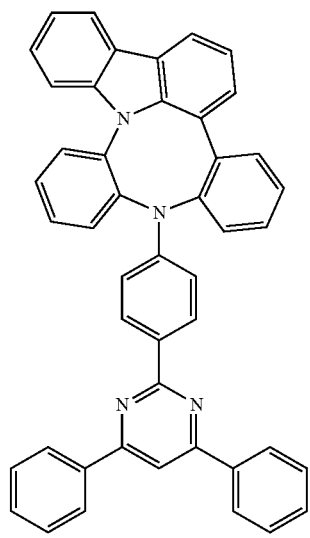
C-53
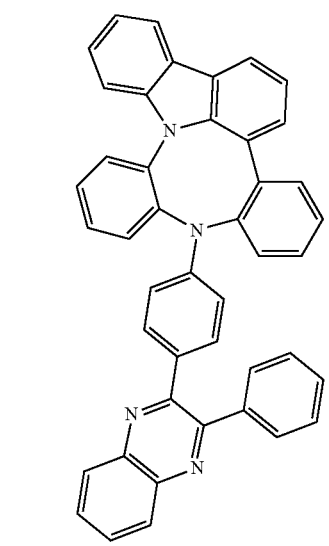
C-54
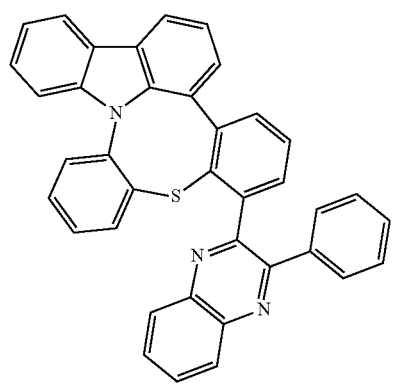
C-55
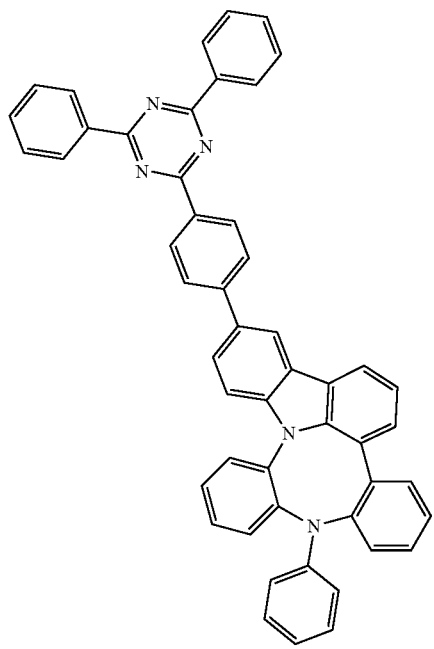
C-56
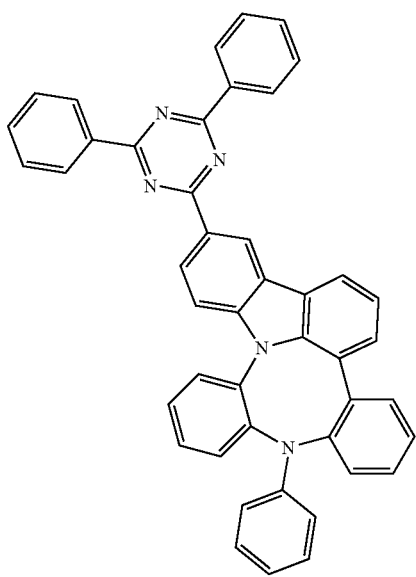

C-57
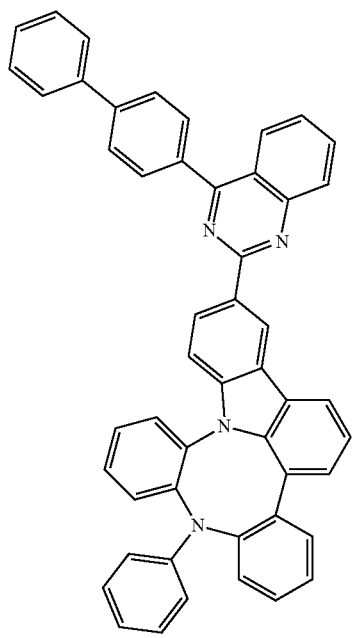
C-59
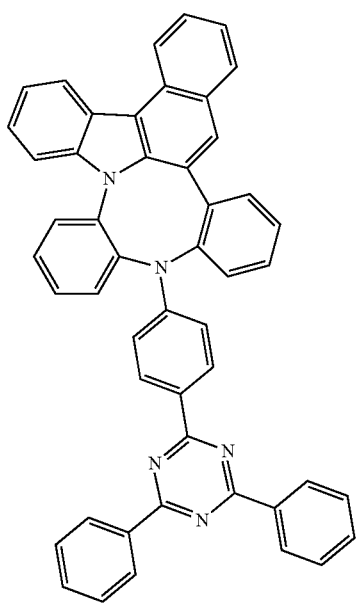
C-58
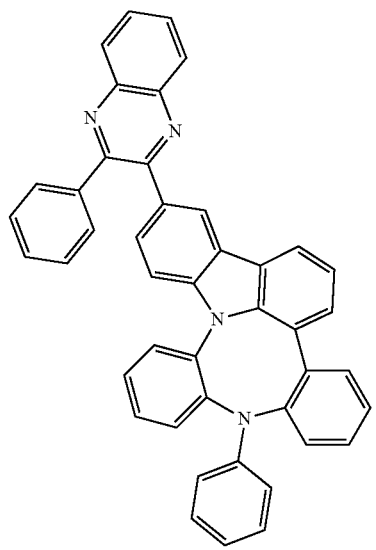
C-60
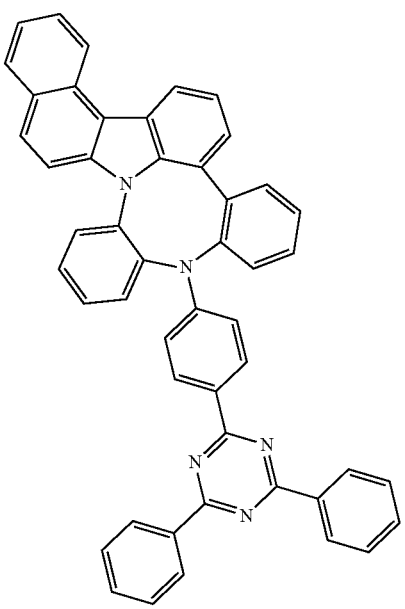

C-61
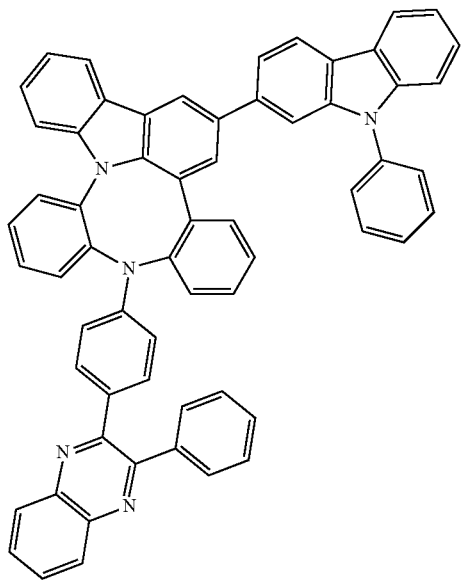
C-62
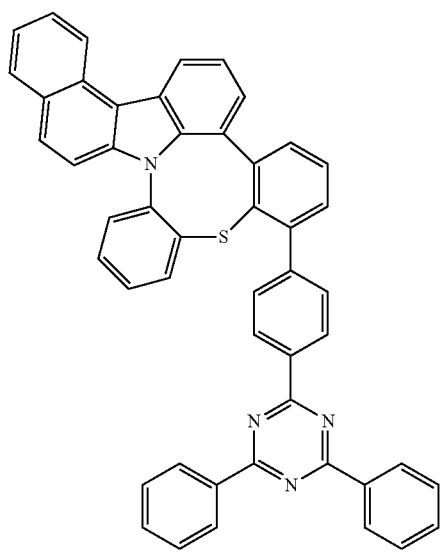
C-63
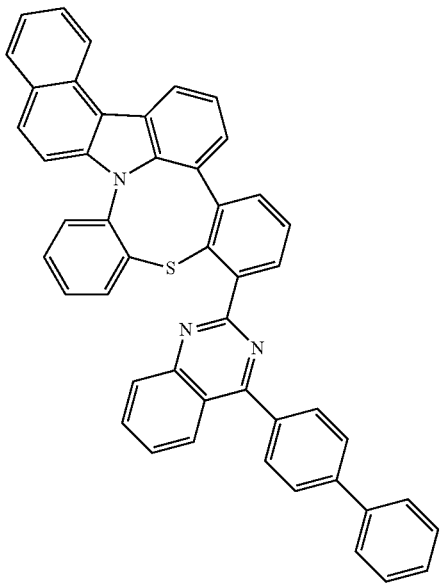
C-64
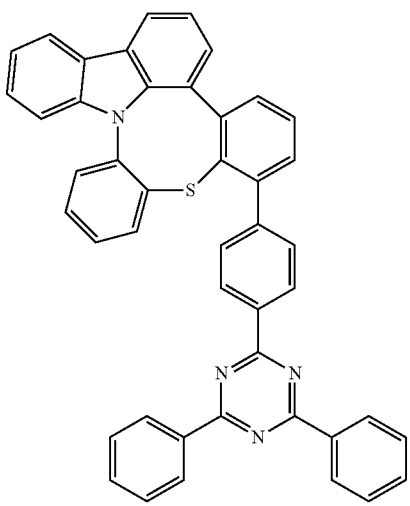
C-65

-continued
C-66
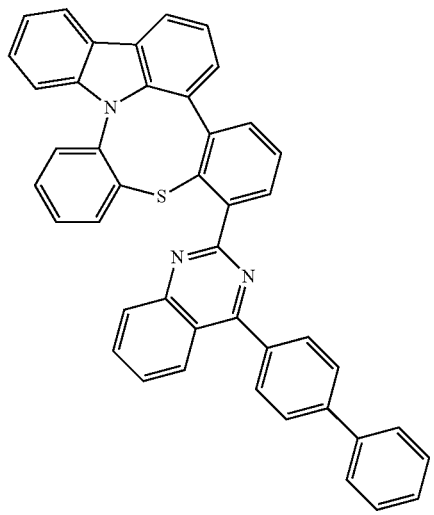
C-67
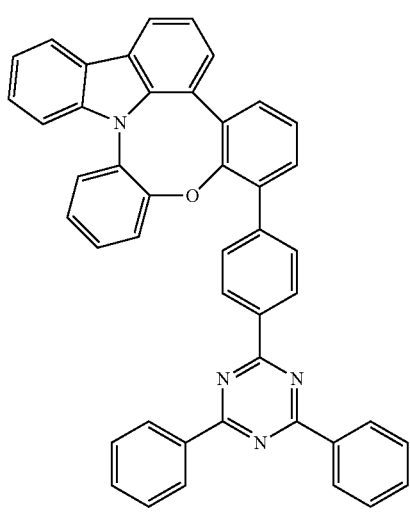
C-68
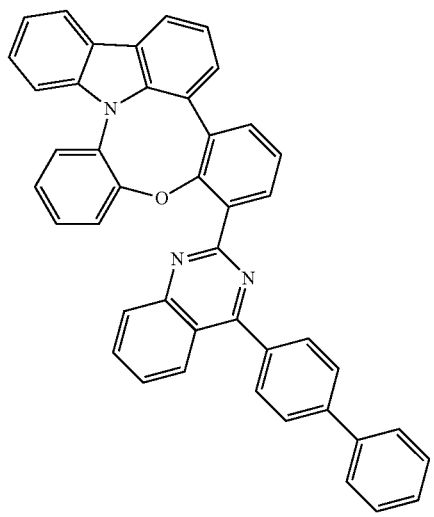
C-69
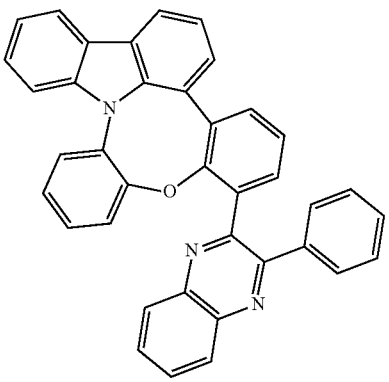
C-70
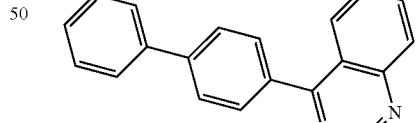
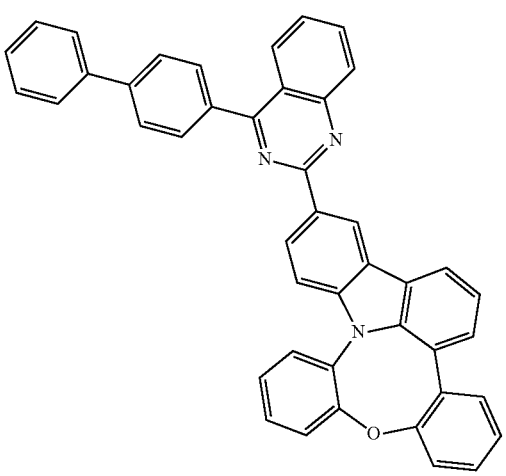
C-71

C-72
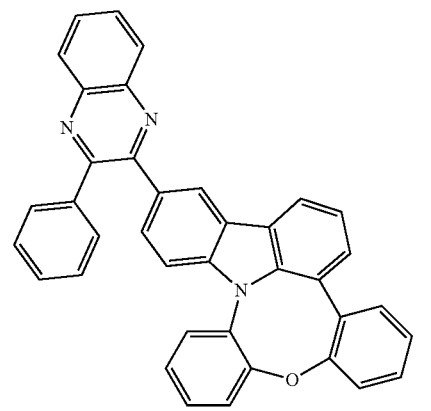
C-73
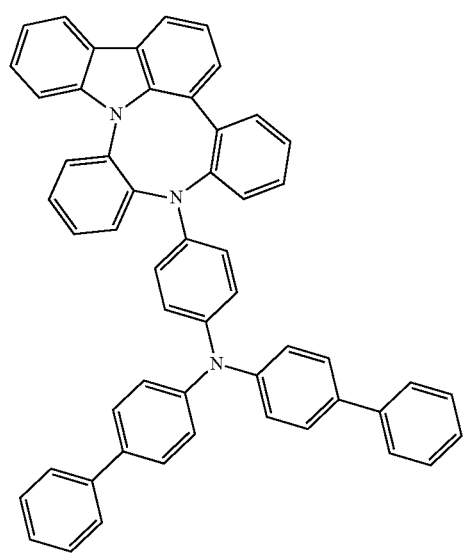
C-74
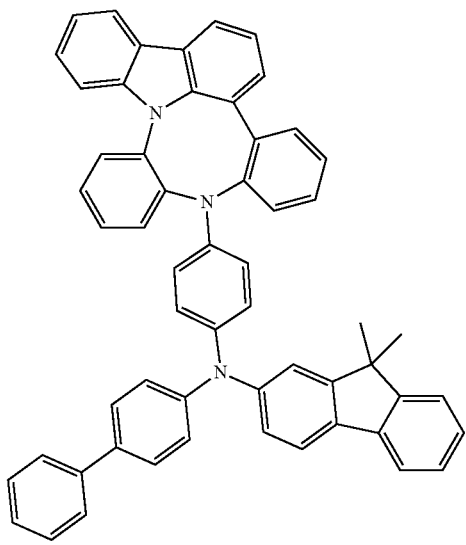
C-75
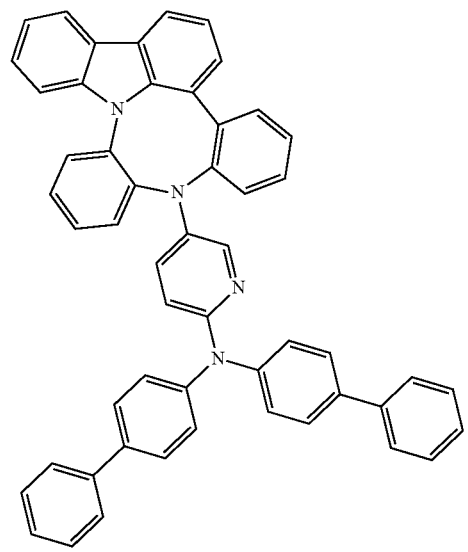
C-76
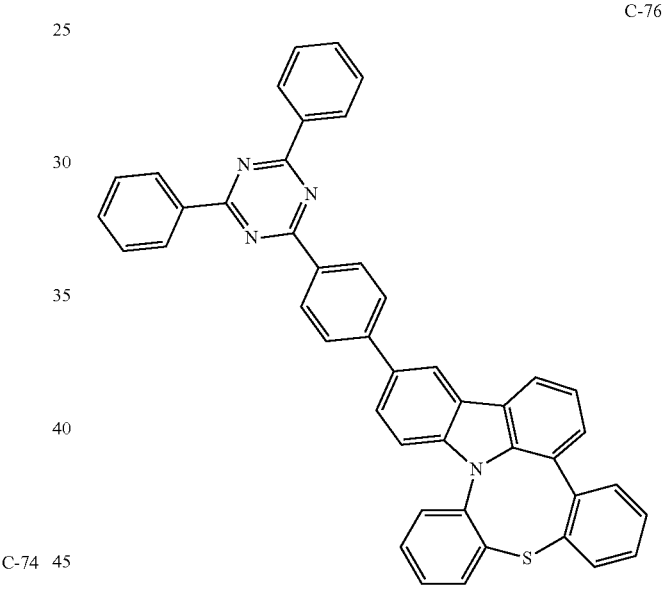
C-77
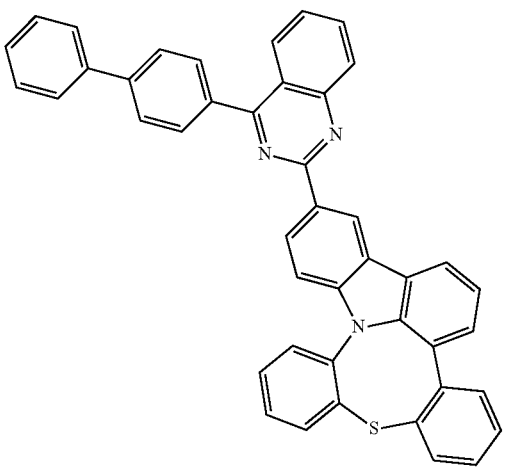

C-78
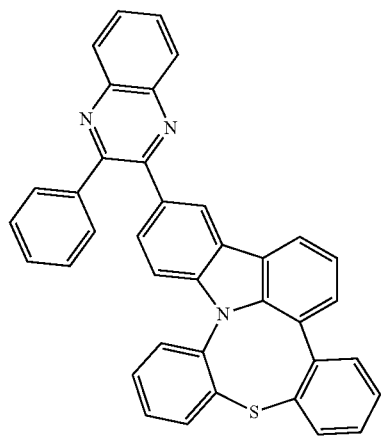
C-80
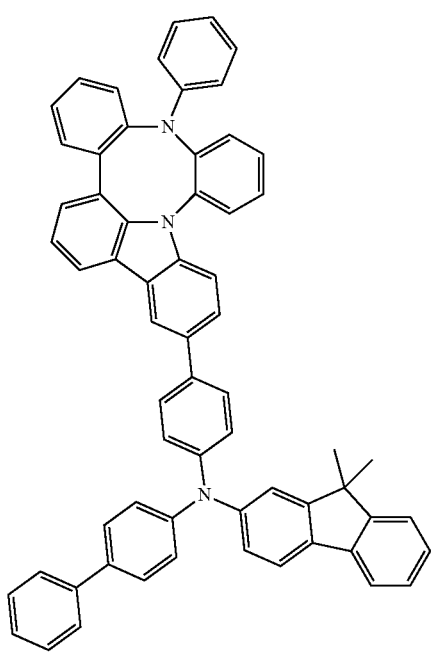
C-79
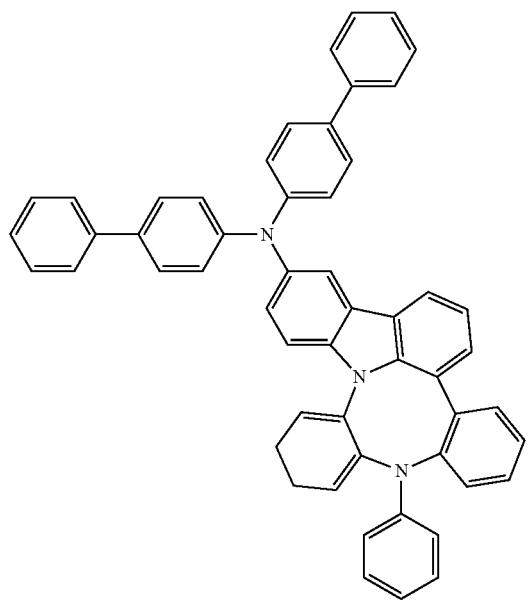
C-81
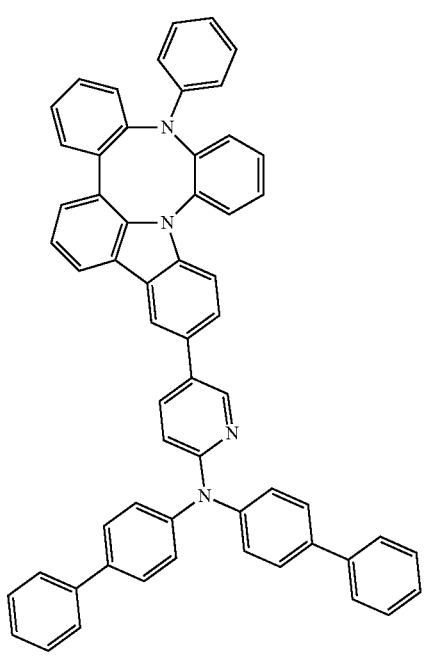

C-82
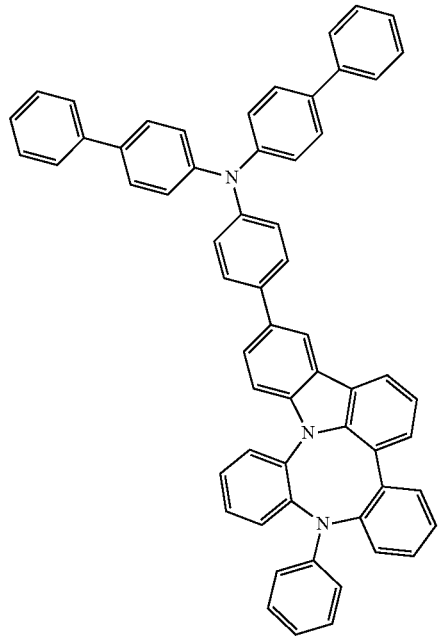
C-84
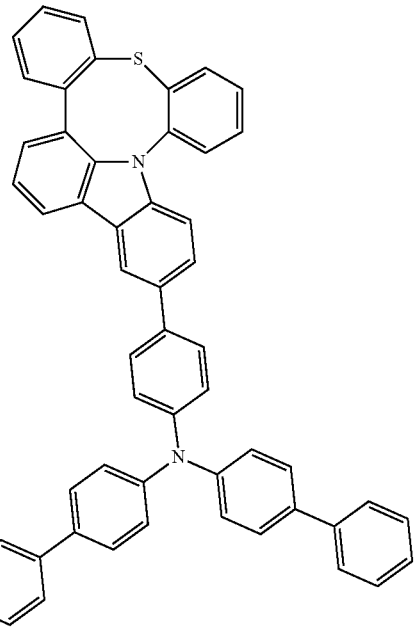
C-83
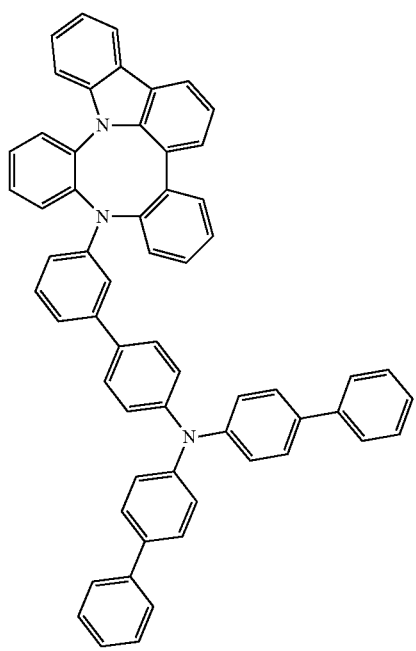
C-85
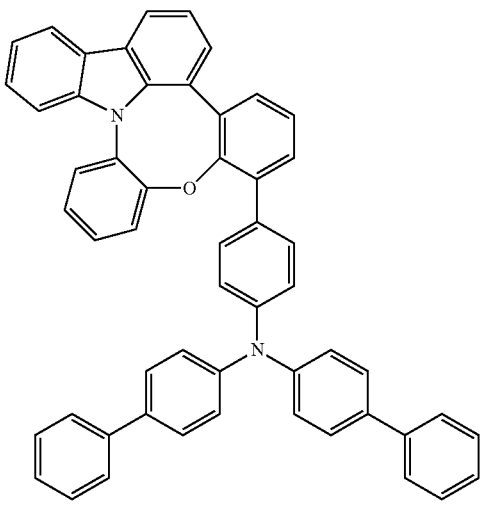

C-86
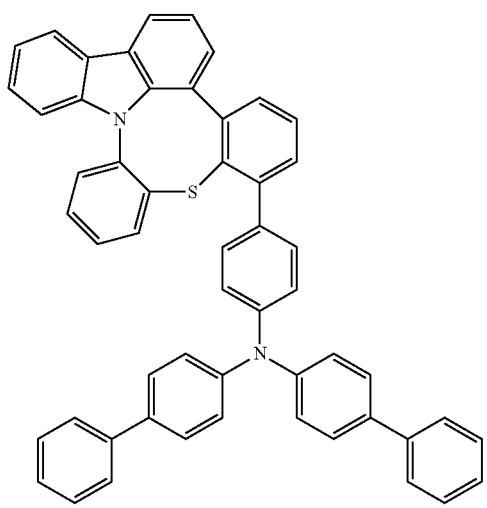
C-88
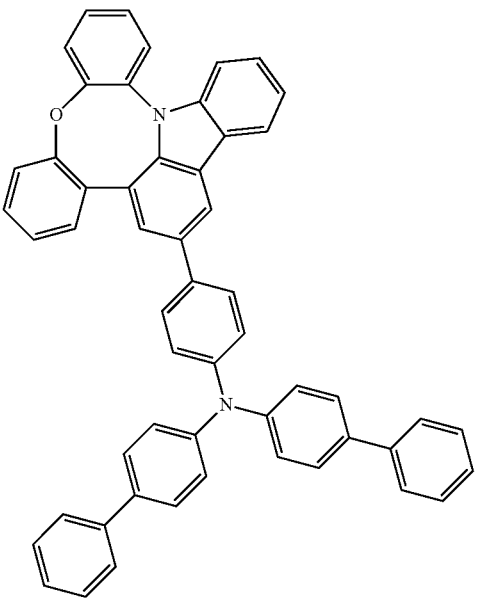
C-87
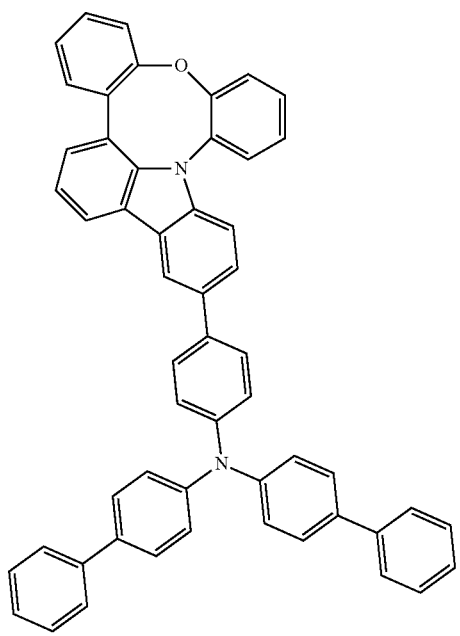
C-89
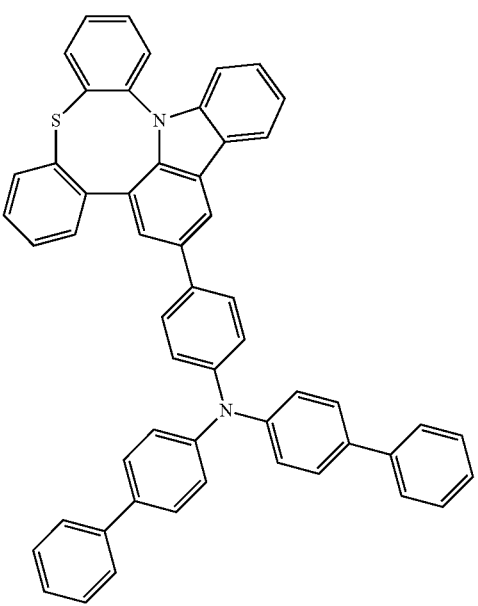

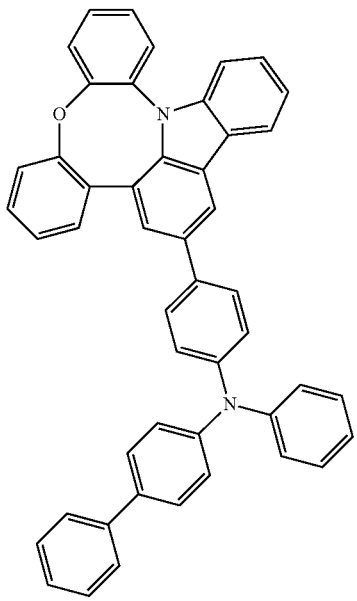
C-90
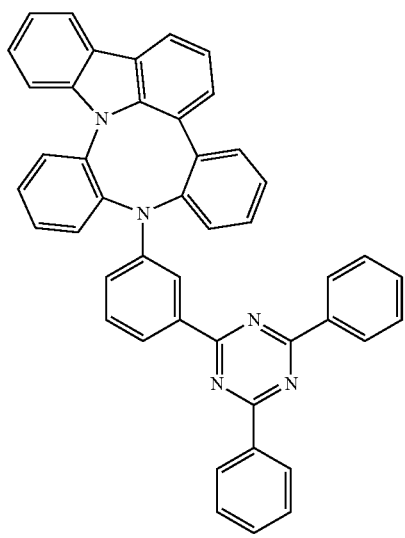
C-91
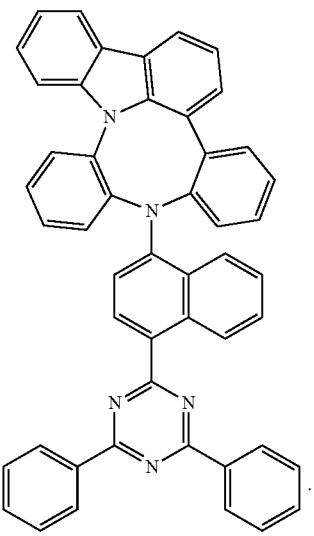
C-92
The organic electroluminescent compound of the present disclosure may be produced by a synthetic method known to a person skilled in the art, for example, the following reaction schemes:
[Reaction Scheme 1]
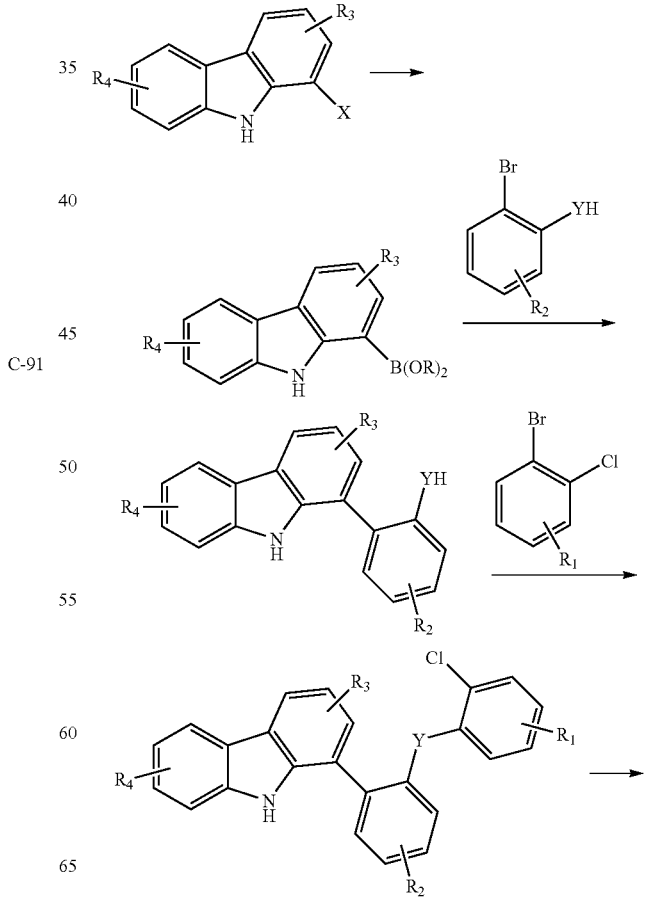

-continued

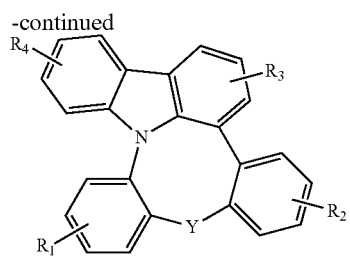

X = Cl, Br, I
Y = NH, O, S wherein, $R_1$ to $R_4$ are as defined in formula 1.

The organic electroluminescent device of the present disclosure may comprise a first electrode, a second electrode, and at least one organic layer between the first and second electrodes. One of the first and second electrodes may be an anode, and the other may be a cathode. The organic layer may comprise at least one light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Herein, the hole auxiliary layer or the light-emitting auxiliary layer may be placed between the hole transport layer and the light-emitting layer, which may control a transport rate of a hole. The hole auxiliary layer or the light-emitting auxiliary layer may be effective to produce an organic electroluminescent device having excellent efficiencies and/or improved lifespan. The electron buffer layer may be composed of two or more layers in order to control the electron injection and improve characteristics of interface between the light-emitting layer and the electron injection layer. Each of the layers may comprise two or more compounds. The hole blocking layer or electron transport layer may be composed of two or more layers, and each of the layers may comprise two or more compounds.

According to one embodiment of the present disclosure, the present disclosure provides an organic electroluminescent material comprising the organic electroluminescent compound represented by formula 1. The organic electroluminescent material may consist of the organic electroluminescent compound represented by formula 1 as a sole compound, or may further comprise conventional materials generally used in organic electroluminescent materials. Preferably, the organic electroluminescent material may comprise the compound represented by formula 1, the compound represented by formula 5, or both of them. The organic electroluminescent material may be a host material, a hole transport material, or an electron buffer material, and preferably, a host material or an electron buffer material, but is not limited thereto.

According to one embodiment of the present disclosure, the compound represented by formula 1 may be comprised in an organic electroluminescent device as an electron buffer material. In other words, the electron buffer material may comprise the compound represented by formula 1. The electron buffer material may control flow properties of an electron. For example, the electron buffer material may trap an electron, block an electron, or lower an energy barrier between an electron transport zone and a light-emitting layer. Specifically, the electron buffer material may be an electron buffer material of an organic electroluminescent device. The electron buffer material in an organic electroluminescent device may be used for an electron buffer layer, or may also be simultaneously used for other zones such as an electron transport layer, an electron injection layer or a light-emitting layer. The electron buffer material may be a mixture or a composition further comprising conventional materials generally used in producing an organic electroluminescent device.

According to one embodiment of the present disclosure, the compound represented by formula 1 may be comprised in an organic electroluminescent device as a host material. In other words, the host material may comprise the compound represented by formula 1. Also, the host material may comprise at least one of a first host compound and at least one of a second host compound. Herein, the weight ratio of the first host compound to the second host compound is in the range of 1:99 to 99:1. The second host compound may be any of the known phosphorescent hosts. It is preferable to use the compound represented by the following formula 5 in terms of driving voltage, luminous efficiency and/or power efficiency. In the host material of the present disclosure, the first host compound may comprise the compound represented by formula 1, and the second host compound may comprise the compound represented by the following formula 5.

The organic electroluminescent material may comprise the organic electroluminescent compound represented by formula 1 and the compound represented by the following formula 5:

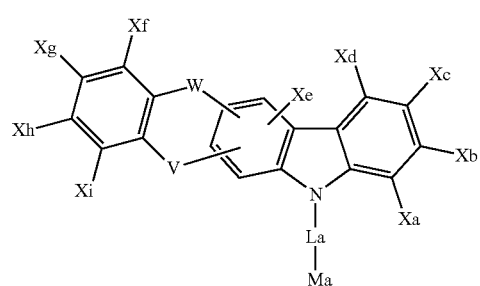

(5)

In formula 5, Ma represents a substituted or unsubstituted nitrogen-containing (5- to 30-membered)heteroaryl; preferably, a substituted or unsubstituted nitrogen-containing (5- to 25-membered)heteroaryl; and more preferably, a substituted or unsubstituted nitrogen-containing (5- to 18-membered)heteroaryl. For example, Ma may represent a substituted triazinyl, a substituted pyrimidinyl, a substituted benzimidazolyl, a substituted quinoxalinyl, a substituted quinolyl, a substituted quinazolinyl, or an unsubstituted naphthyridinyl; and the substituents of the substituted nitrogen-containing (5- to 30-membered)heteroaryl may be a phenyl unsubstituted or substituted with a dibenzothiophenyl, a tert-butyl or a cyano; an unsubstituted biphenyl; an unsubstituted terphenyl; an unsubstituted naphthyl; an unsubstituted dibenzothiophenyl; or a carbazolyl substituted with a phenyl.

In formula 5, La represents a single bond, a substituted or unsubstituted (3- to 30-membered)heteroarylene, or a substituted or unsubstituted (C6-C30)arylene; preferably, a single bond, a substituted or unsubstituted (3- to 25-membered)heteroarylene, or a substituted or unsubstituted (C6-C25)arylene; more preferably, a single bond, an unsubstituted (5- to 18-membered)heteroarylene or an unsubstituted (C6-C18)arylene; and for example, a single bond, an unsubstituted phenylene, an unsubstituted biphenylene, an unsubstituted naphthylene, or an unsubstituted pyridinylene.

In formula 5, one of V and W represents a single bond, and the other of V and W represents any one of NR$_6$, CR$_7$R$_8$, S and O. Preferably, one of V and W represents a single bond, and the other of V and W represents any one of NR$_6$, S and O.

In formula 5, Xa to Xi, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or may be linked to adjacent Xa to Xi, respectively, to form a substituted or unsubstituted mono- or polycyclic (C3-C30), alicyclic or aromatic ring, or the combination thereof, whose carbon atom(s) may be replaced with at least one heteroatom selected from nitrogen, oxygen, and sulfur. Preferably, Xa to Xi, each independently, represent hydrogen, a cyano, a substituted or unsubstituted (C6-C30)aryl, a substituted or unsubstituted (3- to 25-membered)heteroaryl, or a substituted or unsubstituted tri(C6-C25)arylsilyl. More preferably, Xa to Xi, each independently, represent hydrogen, an unsubstituted (C6-C18)aryl, or (6- to 18-membered)heteroaryl unsubstituted or substituted with a (C6-C18)aryl. For example, Xa to Xi, each independently, may represent hydrogen, an unsubstituted phenyl, an unsubstituted naphthyl, an unsubstituted biphenyl, or a carbazolyl substituted with a phenyl.

In formula 5, R$_6$ to R$_8$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; and preferably, a substituted or unsubstituted (C6-C25)aryl; more preferably, an unsubstituted (C6-C18)aryl; and, for example, an unsubstituted phenyl, an unsubstituted naphthyl, or an unsubstituted biphenyl.

In formula 5, the heteroaryl contains at least one heteroatom selected from B, N, O, S, Si, and P, and preferably, N.

The organic electroluminescent compound represented by formula 5 includes the following compounds, but is not limited thereto:

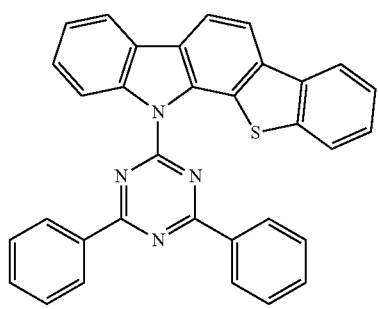

B-1

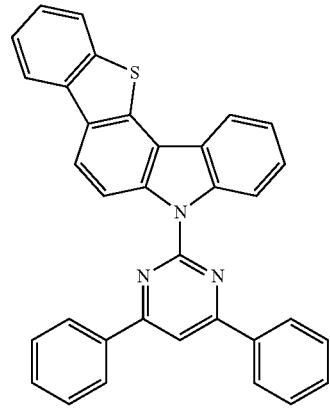

B-2

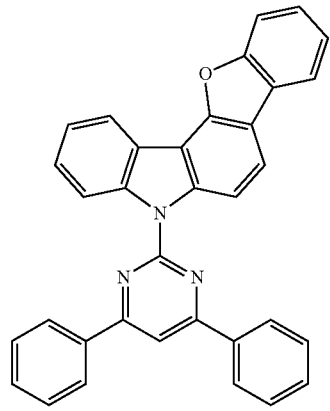

B-3

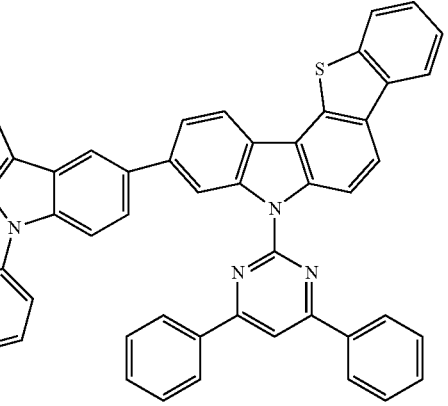

B-4

B-5
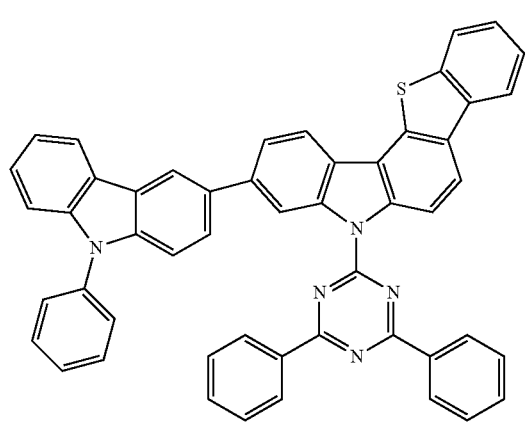
B-8
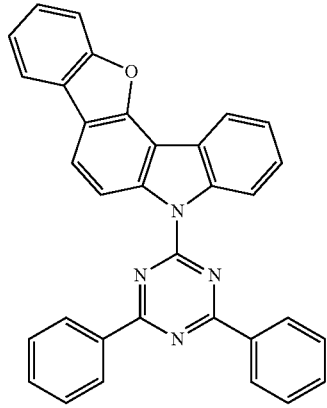
B-6
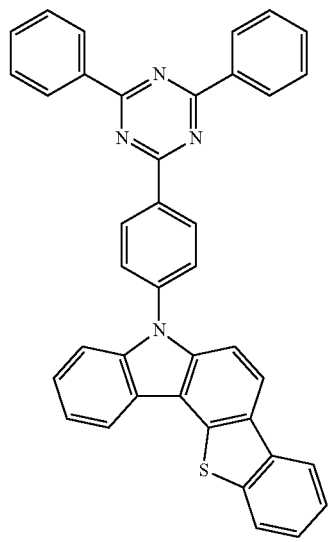
B-9
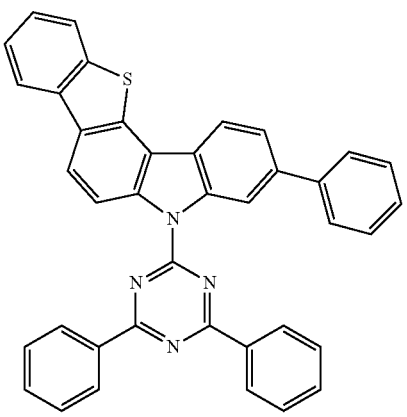
B-7
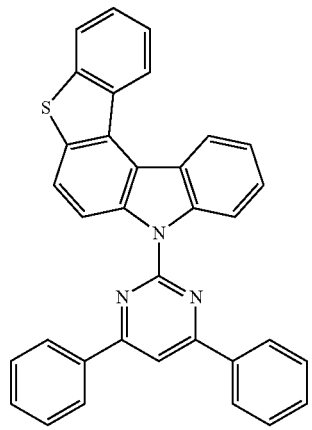
B-10
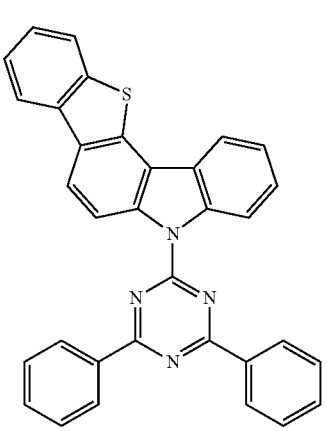

B-11
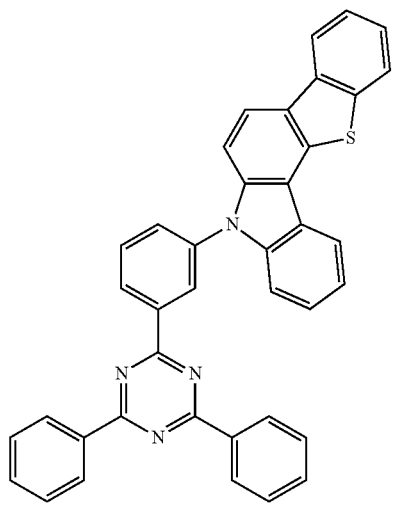
B-12
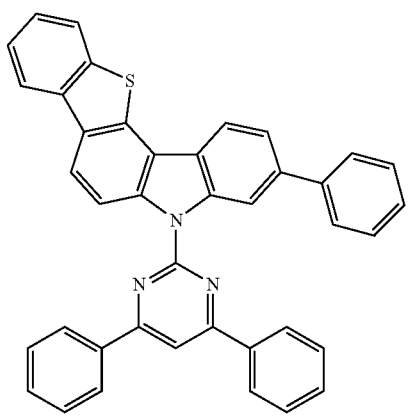
B-13
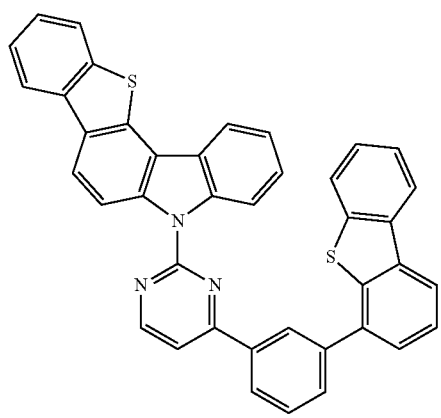
B-14
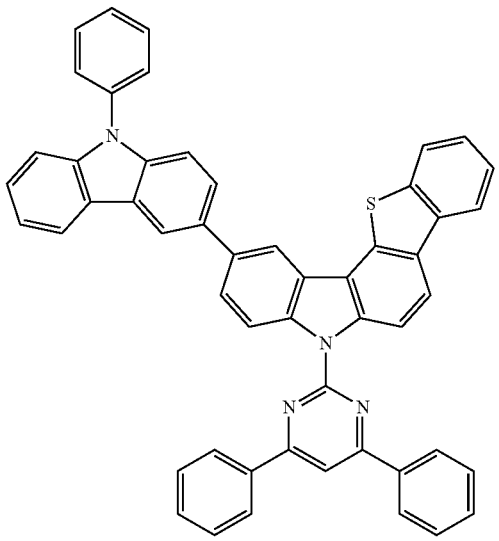
B-15
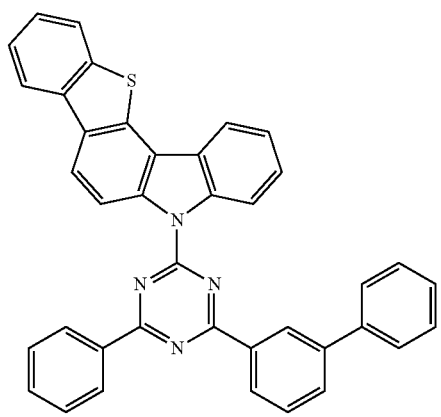
B-16
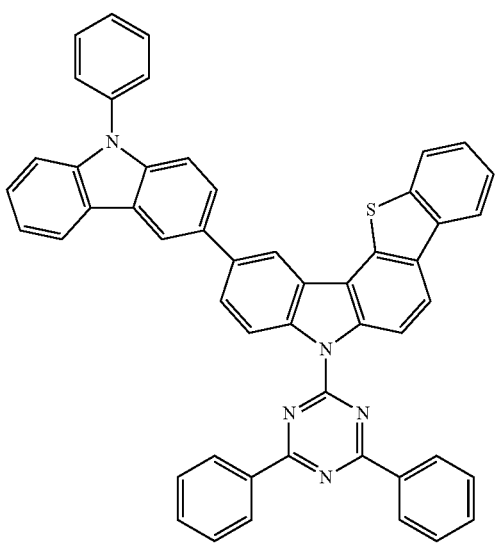

-continued
B-17
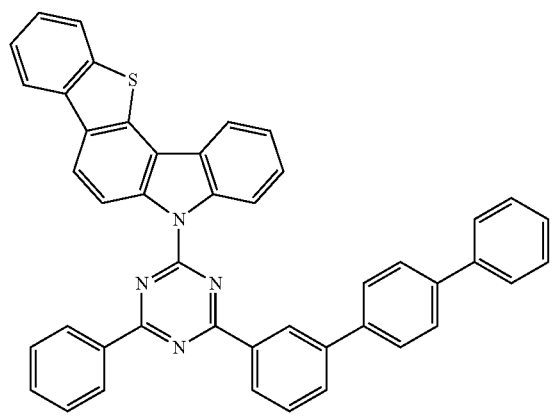
B-18
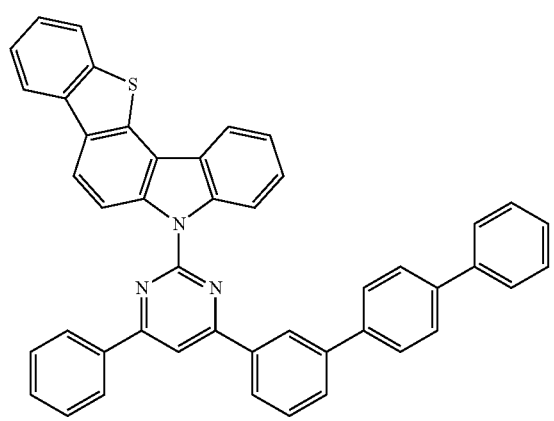
B-19
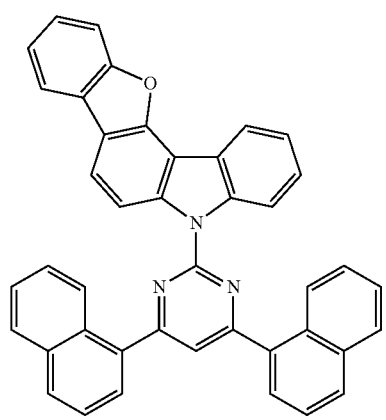
-continued
B-20
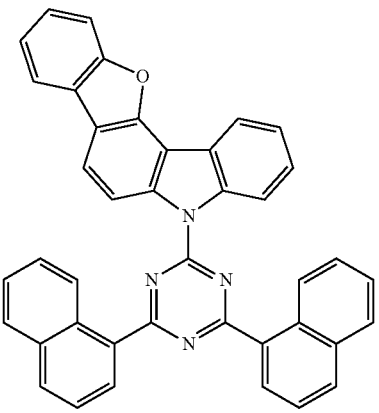
B-21
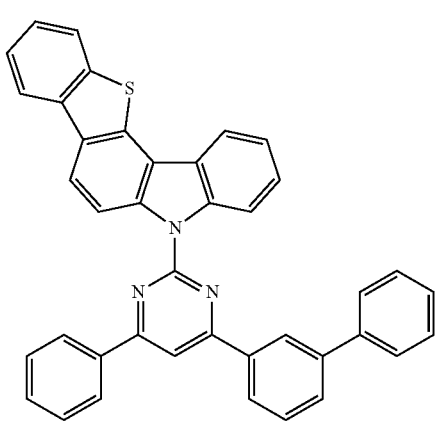
B-22
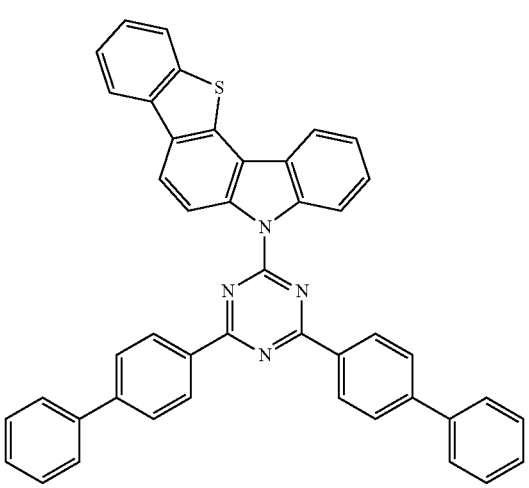

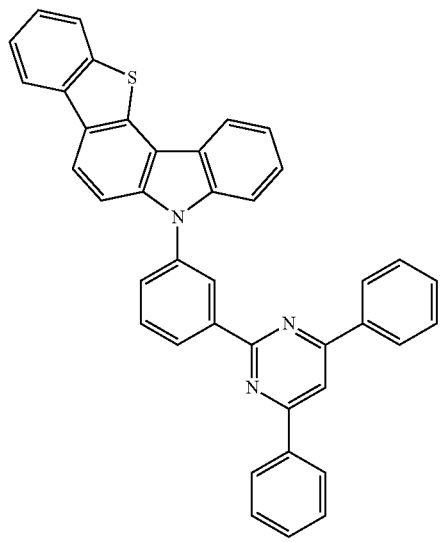
B-23
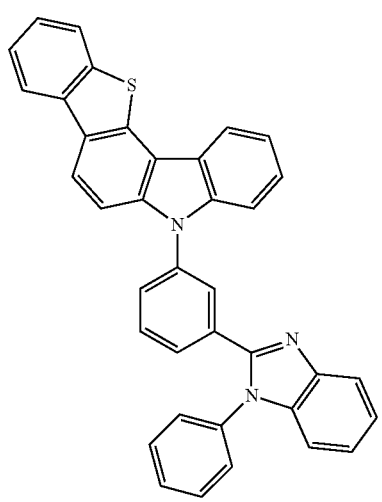
B-24
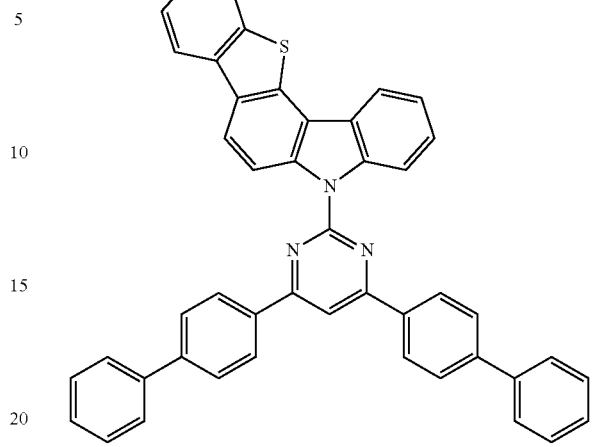
B-26
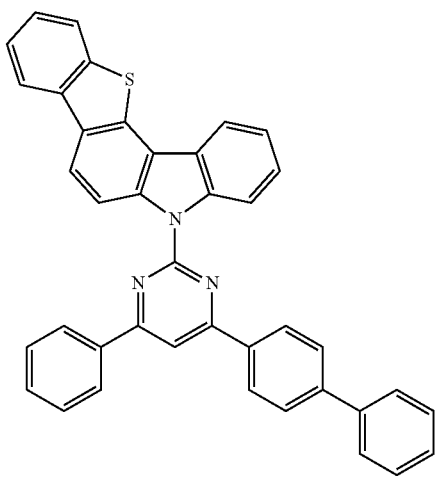
B-27
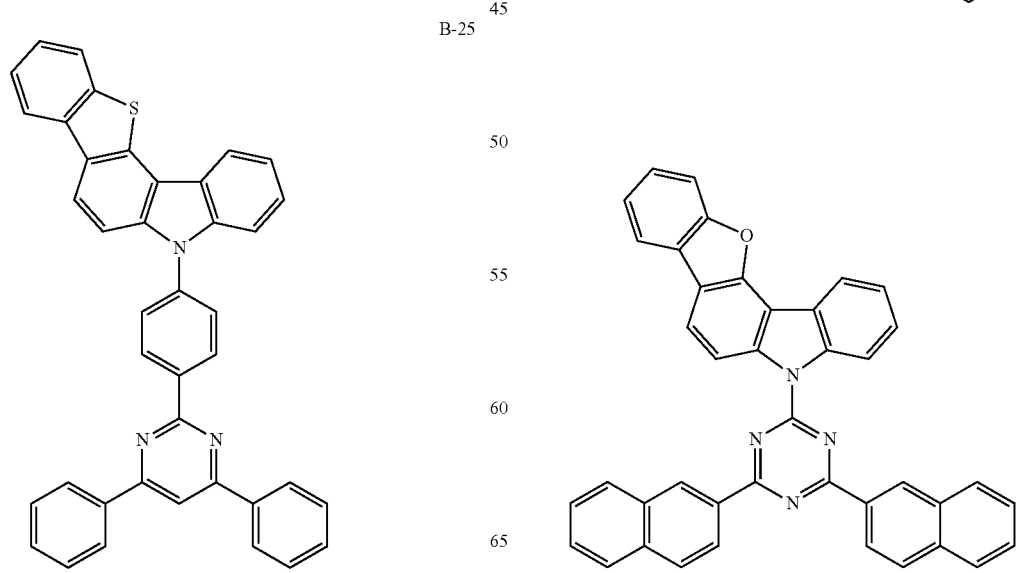
B-25
B-28

B-29
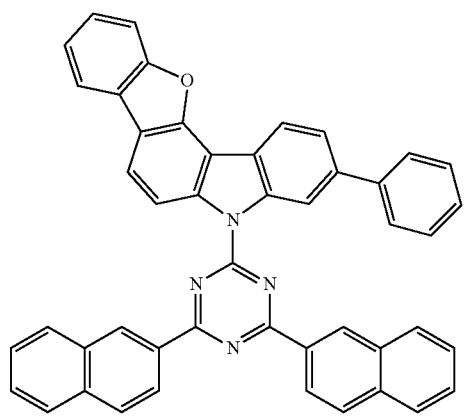
B-30
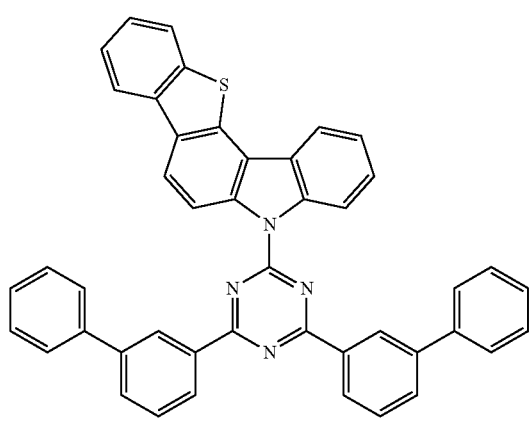
B-31
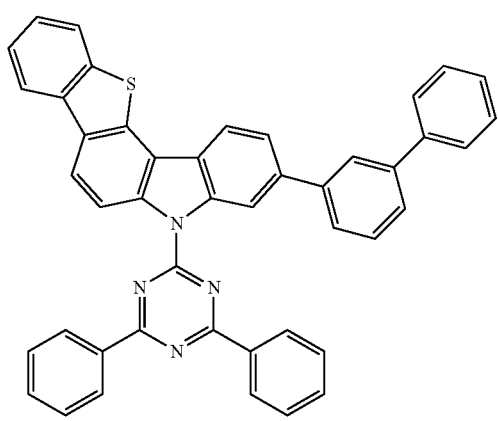
B-32
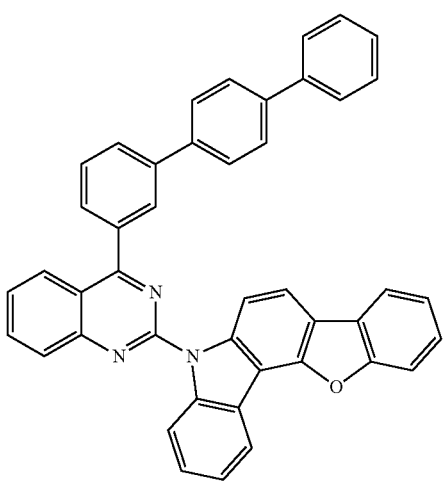
B-33
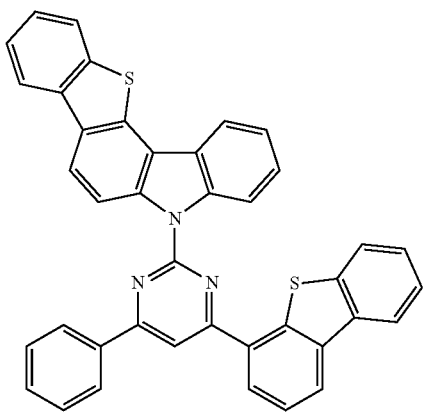
B-34
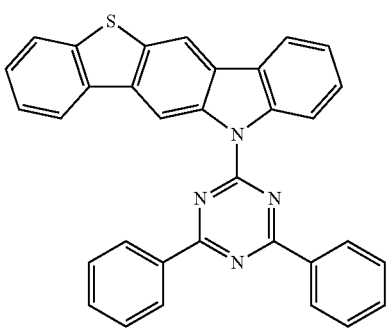

B-35
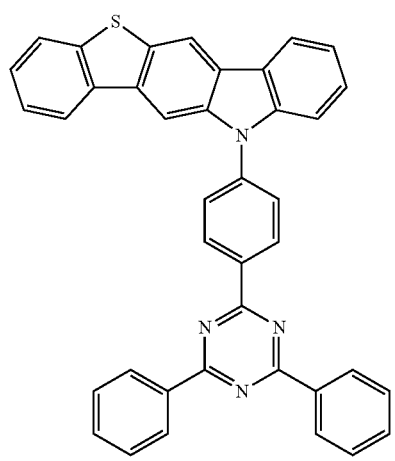
B-36
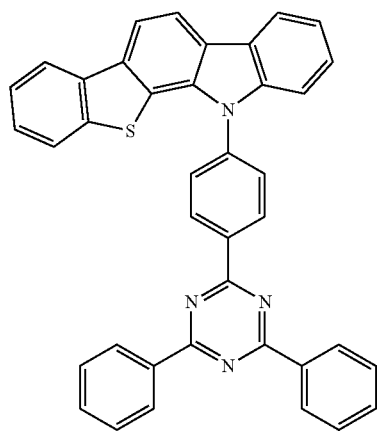
B-37
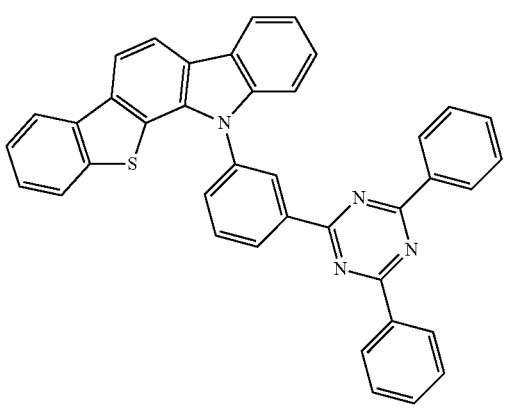
B-38
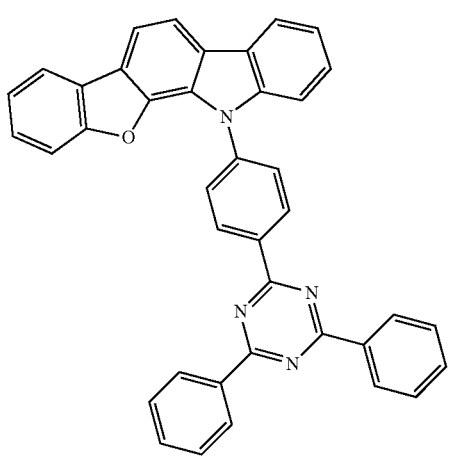
B-39
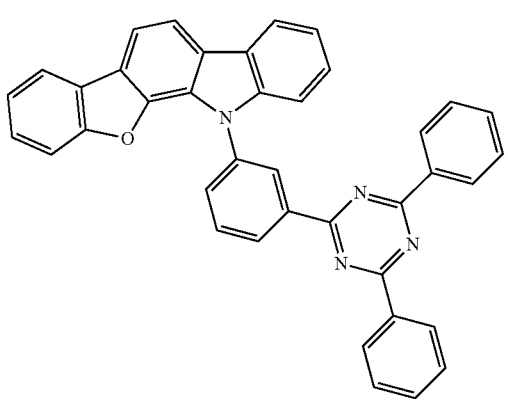
B-40
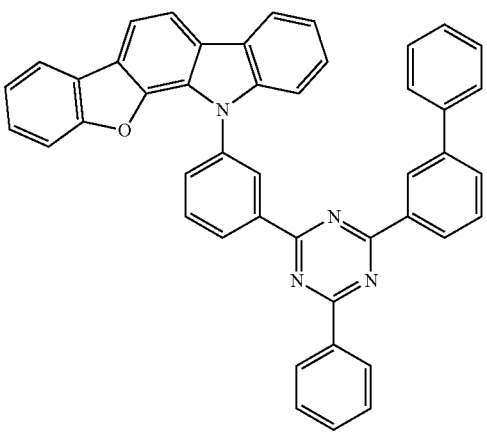
B-41
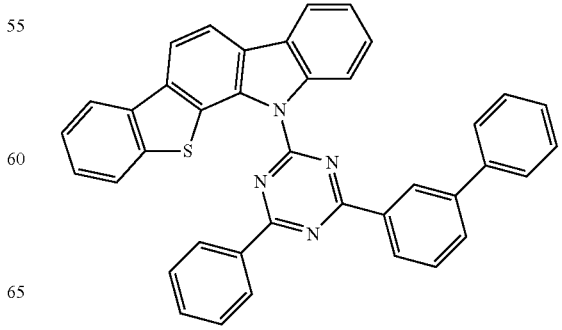

-continued
B-42
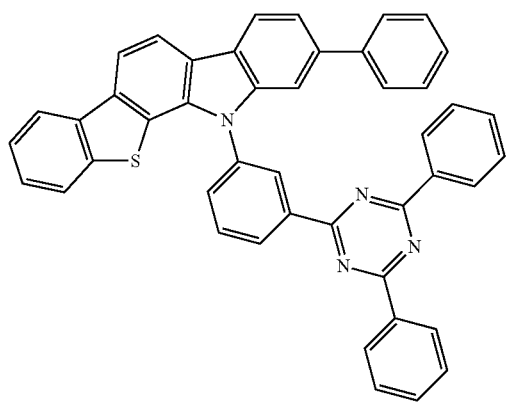
B-43
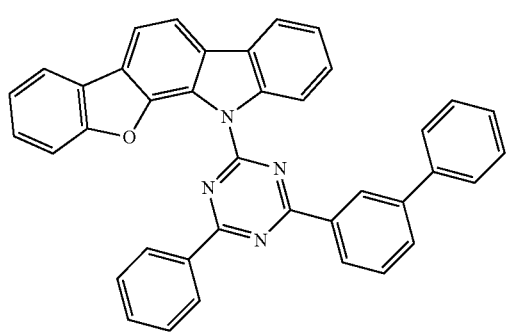
B-44
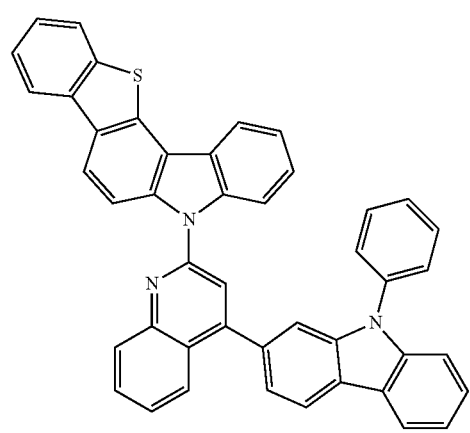
B-45
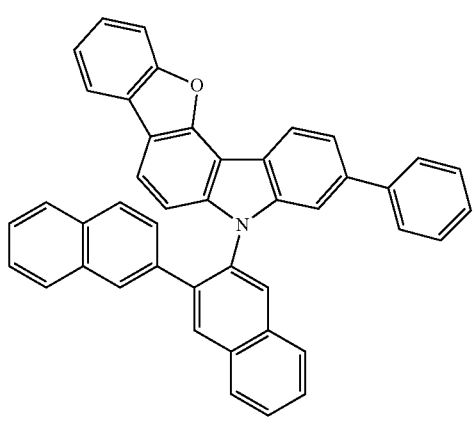
B-46
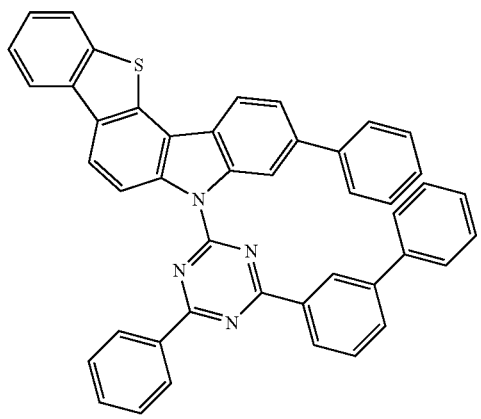
B-47
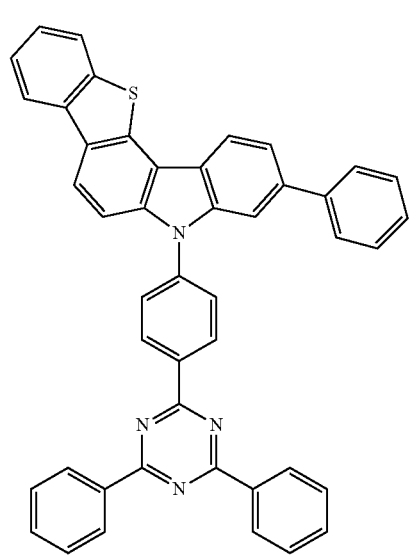
B-48
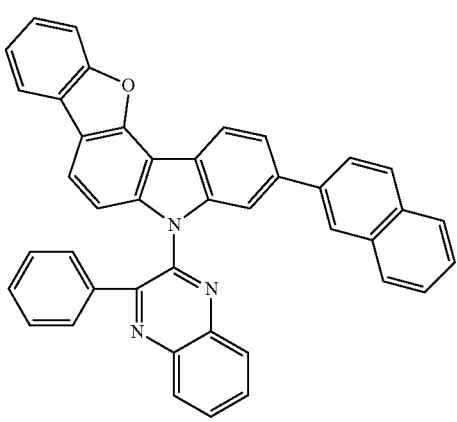

-continued
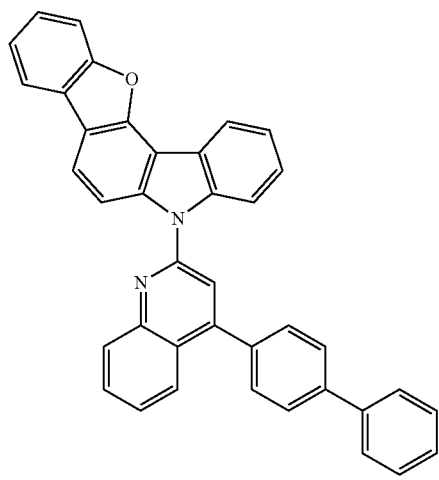
B-49
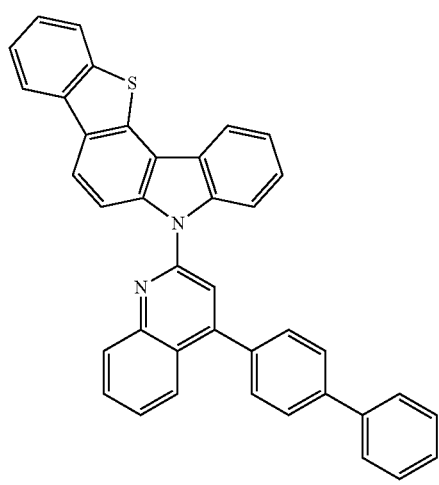
B-50
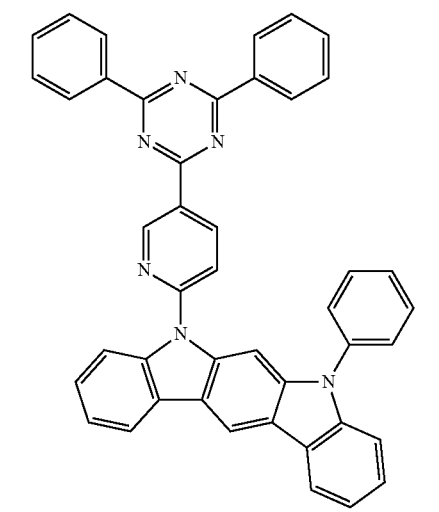
B-51
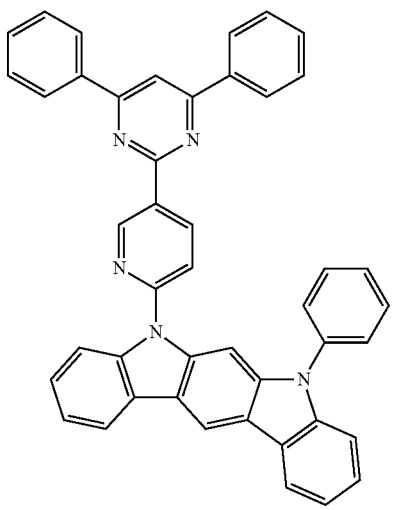
B-52
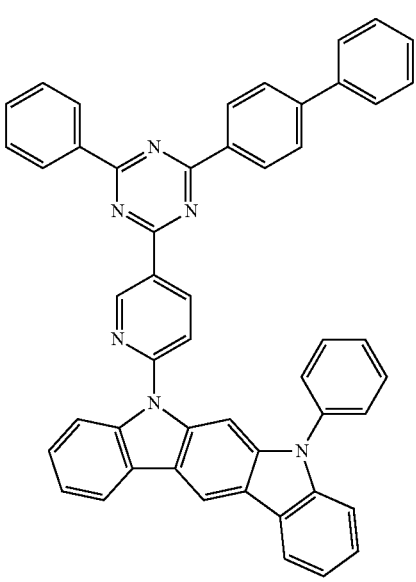
B-53
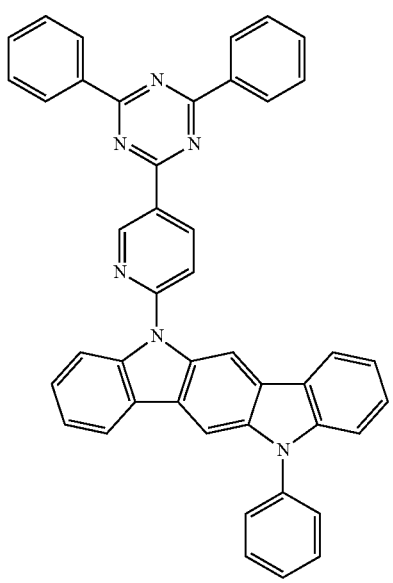
B-54

B-55
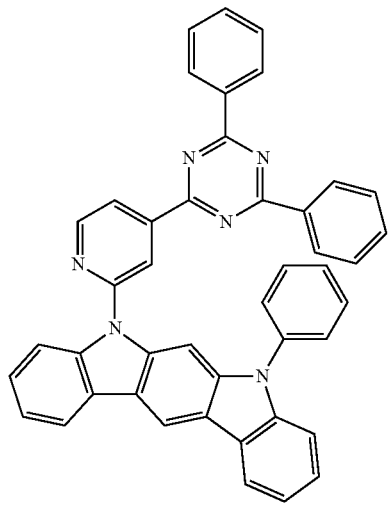
B-58
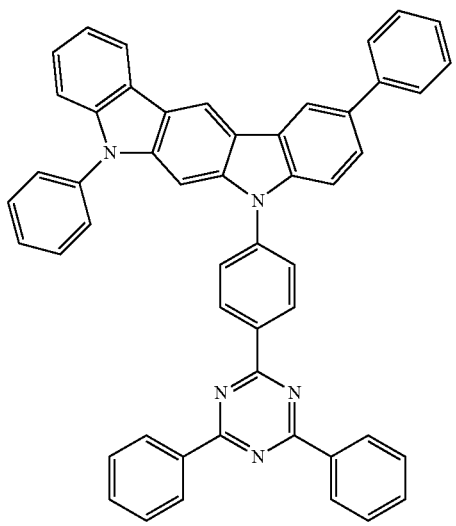
B-56
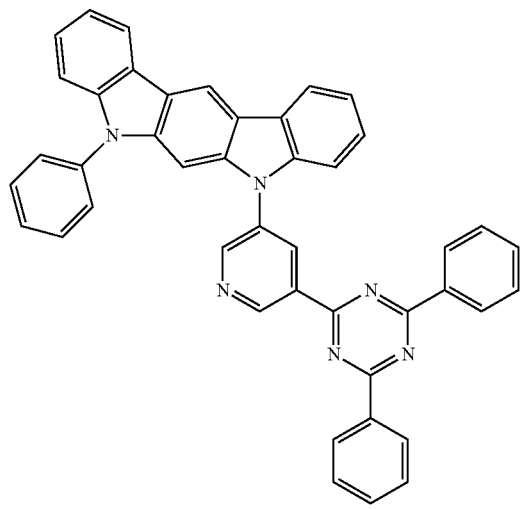
B-59
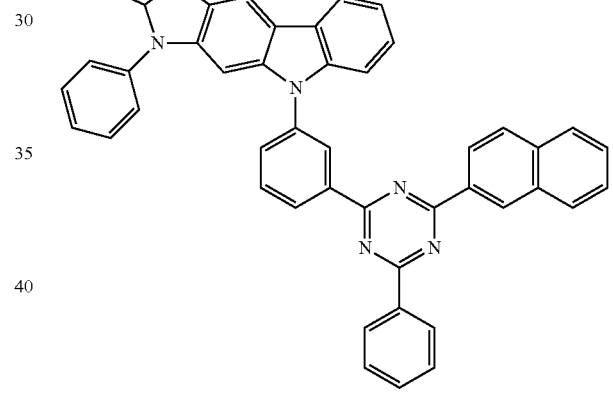
B-57
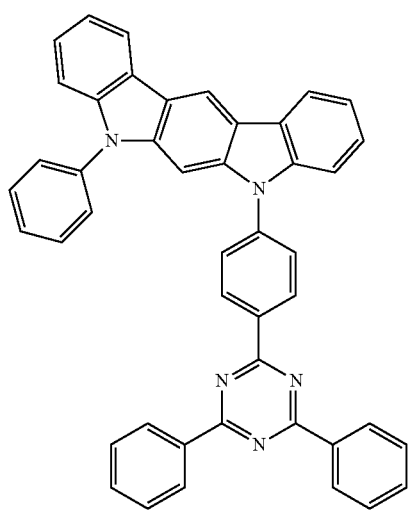
B-60
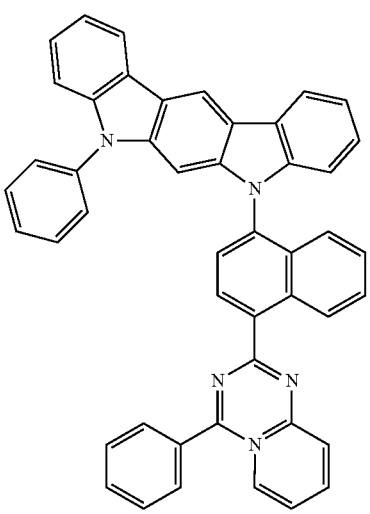

-continued
B-61
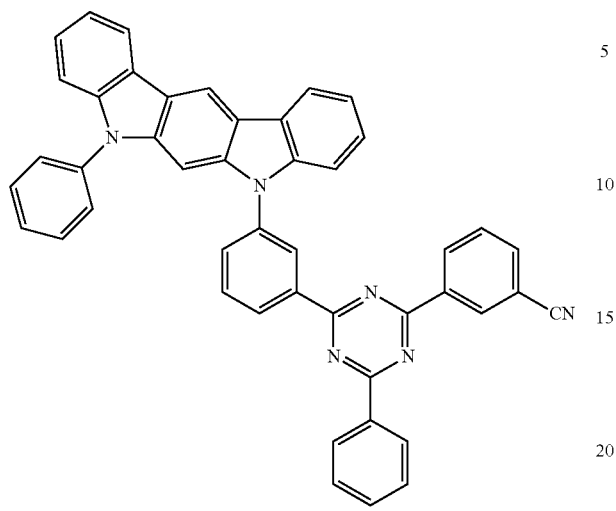
B-62
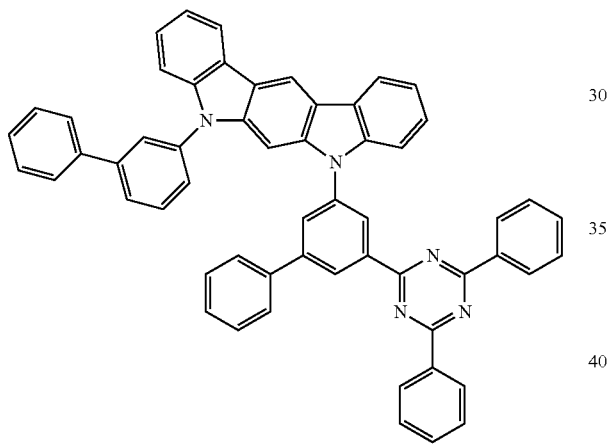
B-63
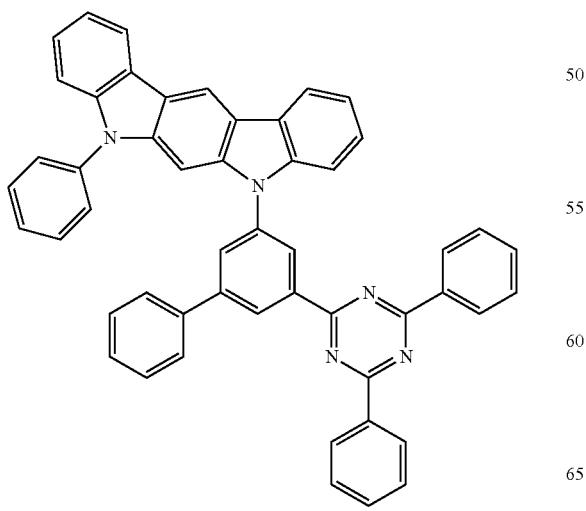
B-64
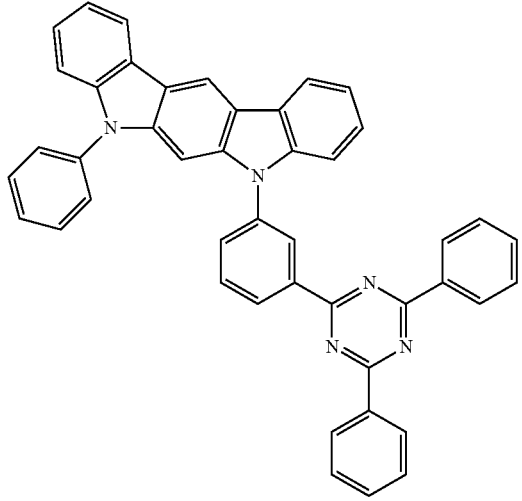
B-65
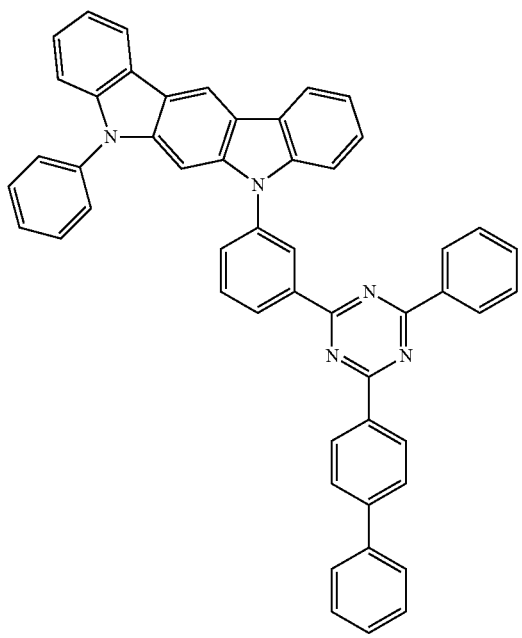

B-66
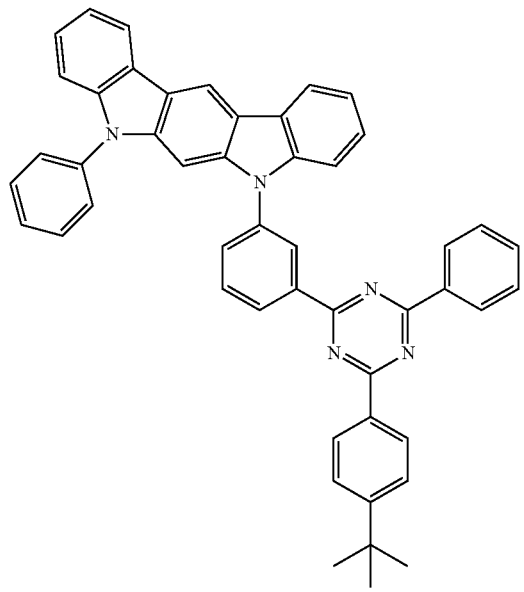
B-67
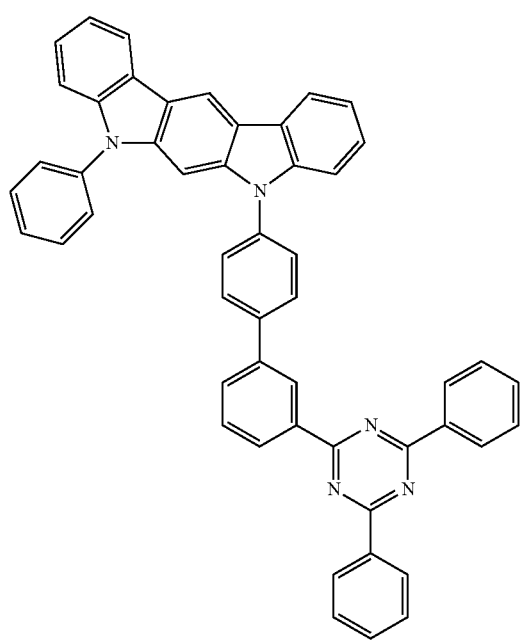
B-68
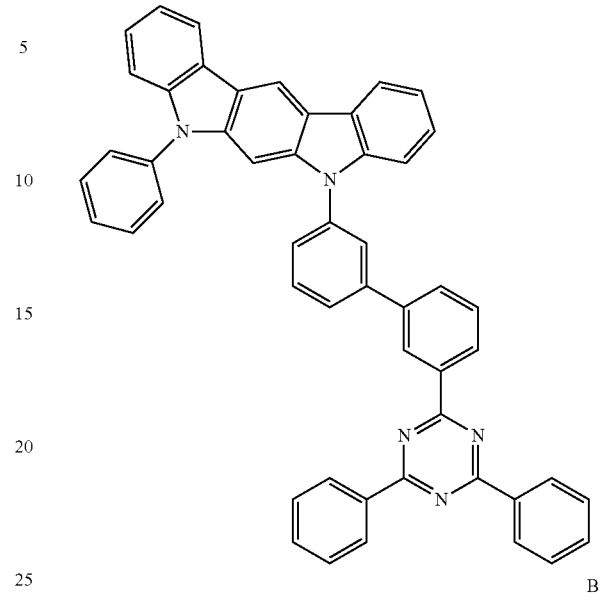
B-69
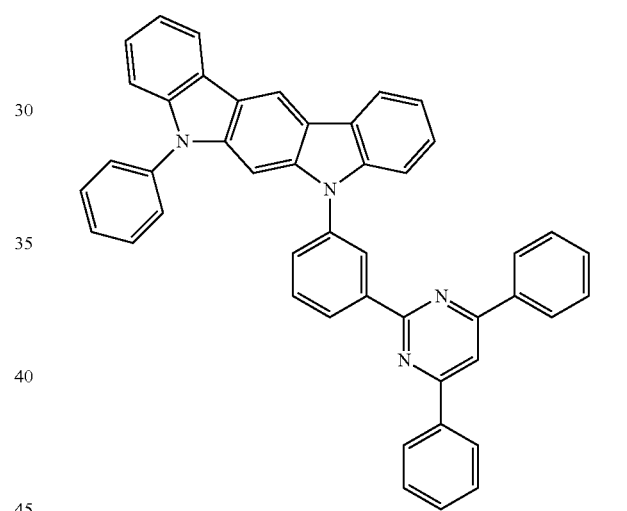
B-70
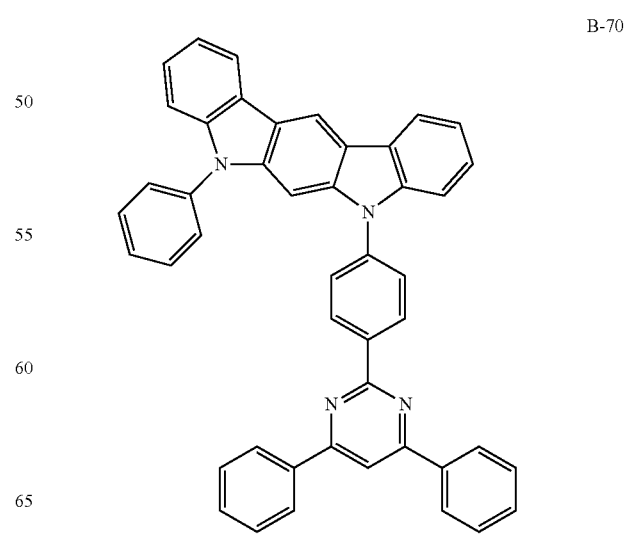

-continued
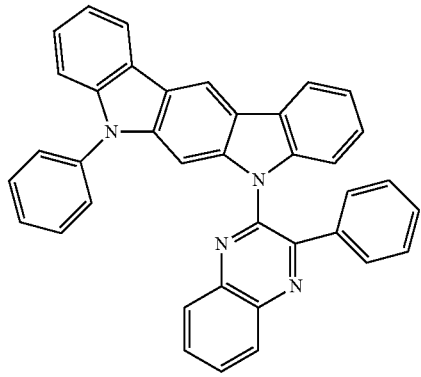
B-71
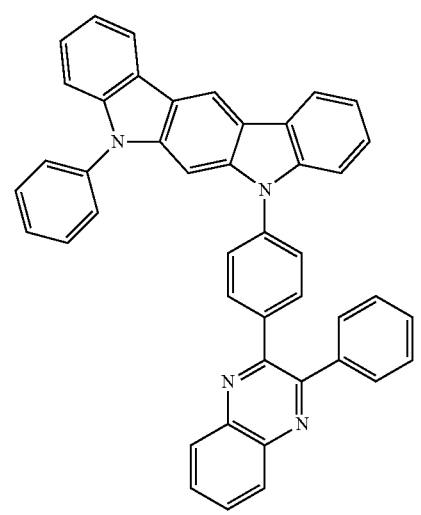
B-72
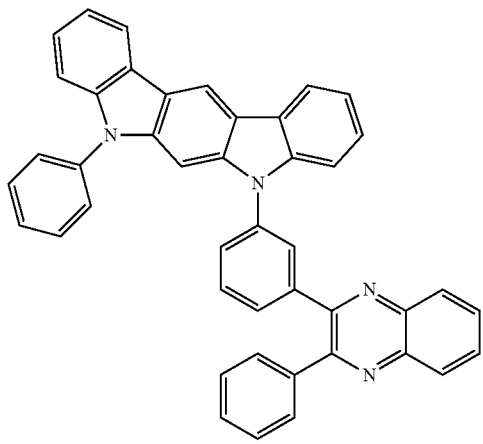
B-73
-continued
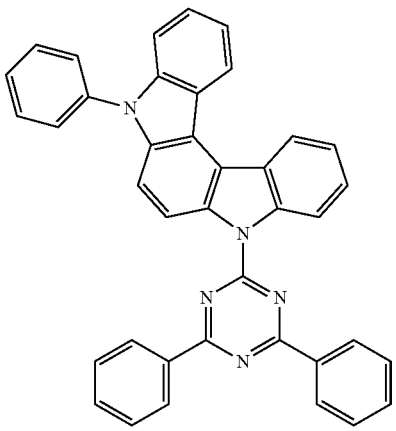
B-74
B-75
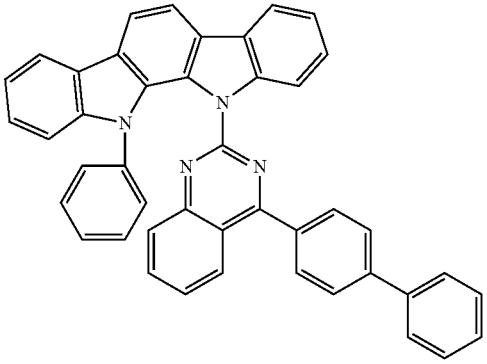
B-76

B-77
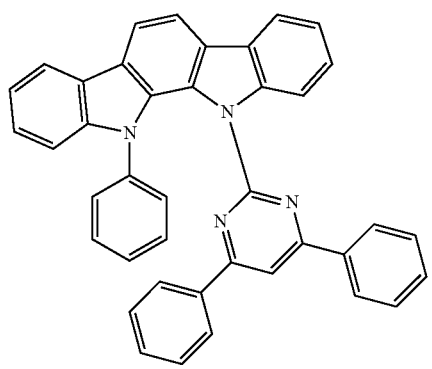
B-78
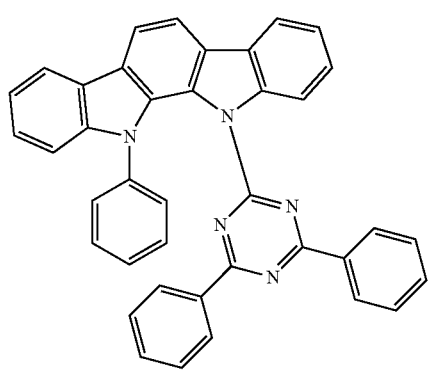
B-79
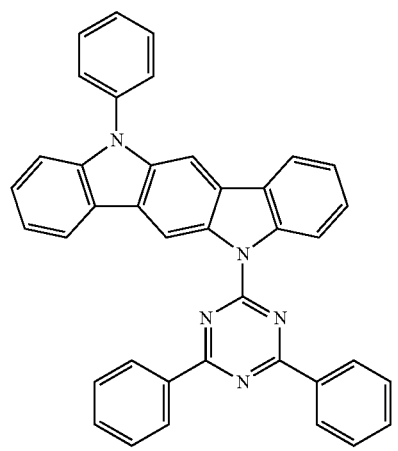
B-80
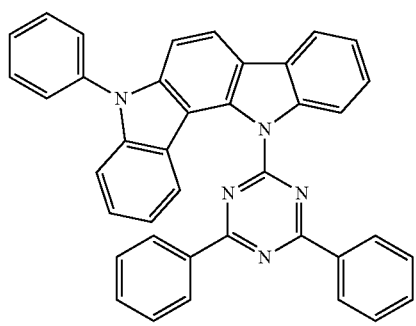
B-81
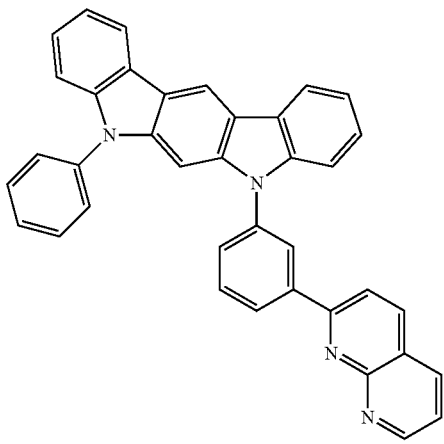
B-82
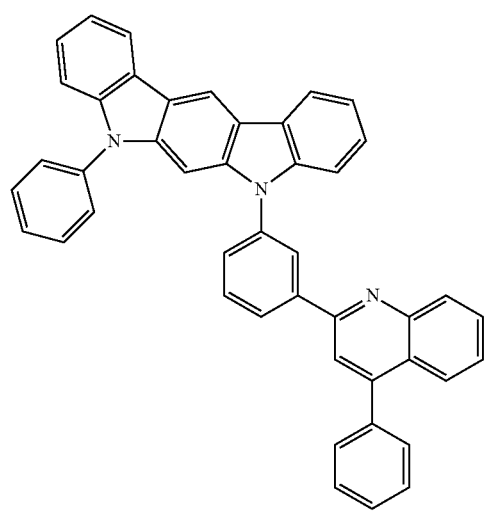
B-83
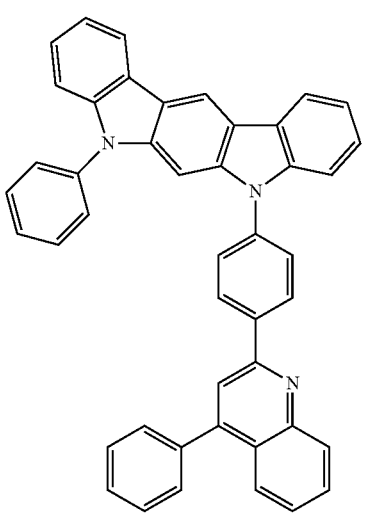

B-84
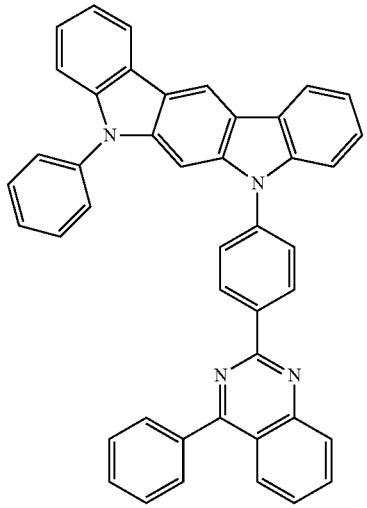

B-87
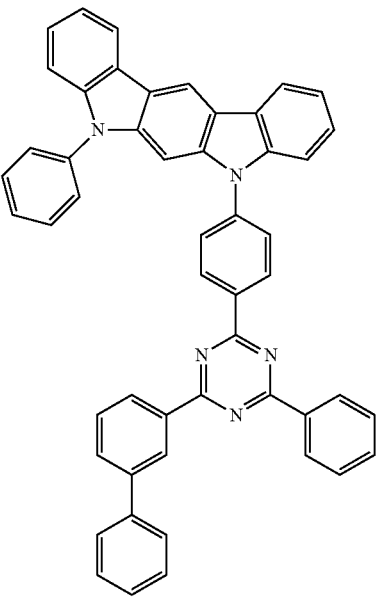

B-85
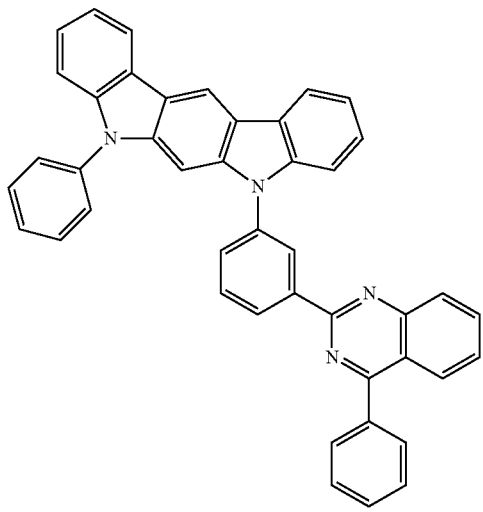

B-88
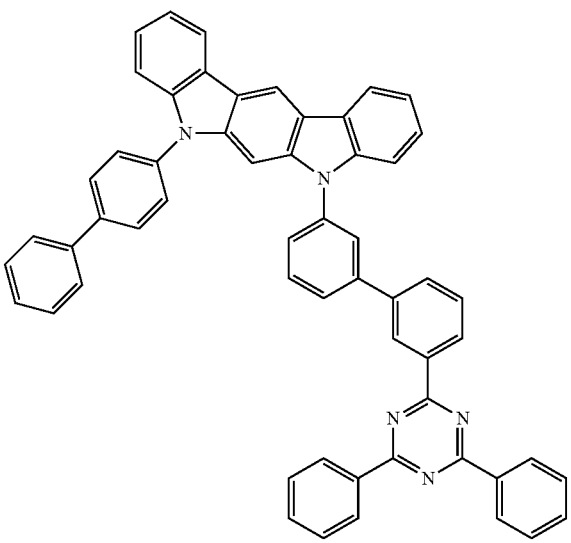

B-86
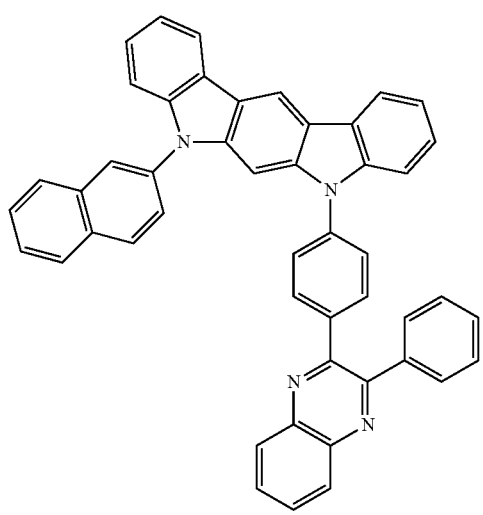

The compound represented by formula 5 of the present disclosure may be produced by a synthetic method known to a person skilled in the art, in particular, a synthetic method disclosed in numerous patent publications. For example, compounds B-1 and B-15, which are well-known materials, may be synthesized by the method disclosed in the following patent application Laid-Open, but are not limited thereto. Specifically, the synthesis methods of compound B-1 and the derivatives thereof are disclosed in Korean Patent Application Laid-Open No. 2016-0010333, published on Jan. 27, 2016. Also, the synthesis methods of compound B-15 and the derivatives thereof are disclosed in Korean Patent Application Laid-Open No. 2013-0011446, published on Jan. 30, 2013.

The dopant comprised in the organic electroluminescent device of the present disclosure may be at least one phosphorescent or fluorescent dopant, preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound selected from the group consisting of the compounds represented by the following formulas 101 to 103.

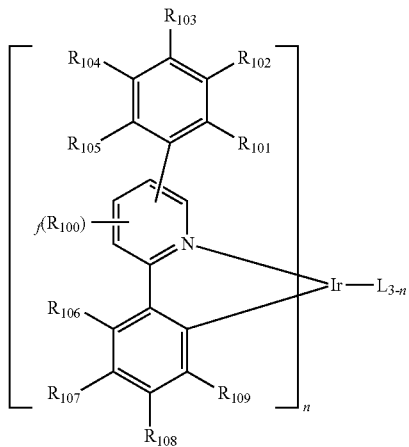
(101)

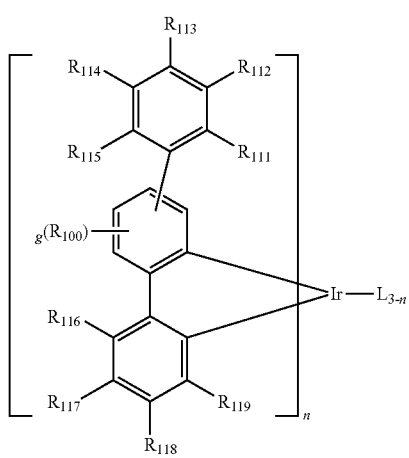
(102)

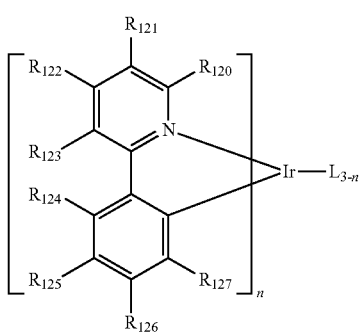
(103)

wherein, L is selected from the following structures:

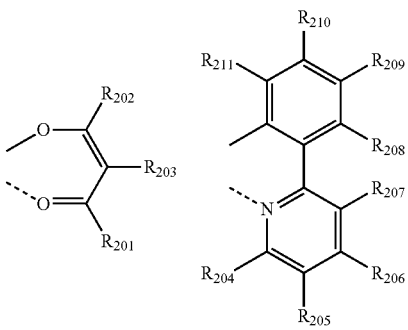

$R_{100}$ represents hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a substituted or unsubstituted (C1-C30)alkyl, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to adjacent $R_{106}$ to $R_{109}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and $R_{120}$ to $R_{123}$ may be linked to adjacent $R_{120}$ to $R_{123}$, respectively, to form a substituted or unsubstituted fused ring, e.g., a quinoline unsubstituted or substituted with an alkyl or an aryl;

$R_{124}$ to $R_{127}$, each independently, represent hydrogen, deuterium, a halogen, a substituted or unsubstituted (C1-C30)alkyl, or a substituted or unsubstituted (C6-C30)aryl; and $R_{124}$ to $R_{127}$ may be linked to adjacent $R_{124}$ to $R_{127}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

$R_{201}$ to $R_{211}$, each independently, represent hydrogen, deuterium, a halogen, a substituted or unsubstituted (C1-C30)alkyl, a substituted or unsubstituted (C3-C30)cycloalkyl, or a substituted or unsubstituted (C6-C30)aryl; and $R_{208}$ to $R_{211}$ may be linked to adjacent $R_{208}$ to $R_{211}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where if f or g is an integer of 2 or more, each $R_{100}$ may be the same or different; and n represents an integer of 1 to 3.

The specific examples of the compound used as a dopant are as follows:

-continued
D-1
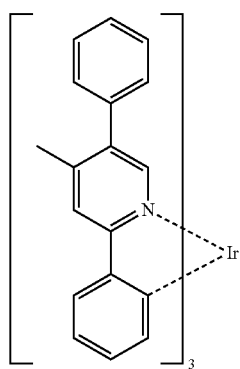
D-5
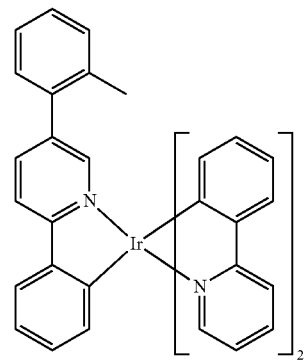
D-2
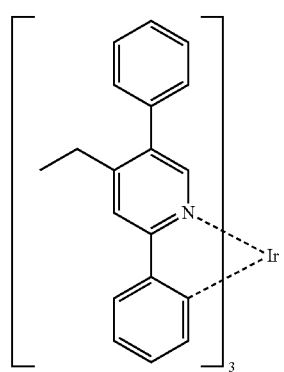
D-6
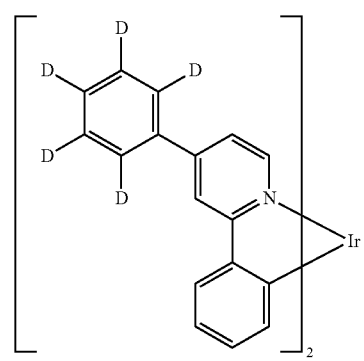
D-3
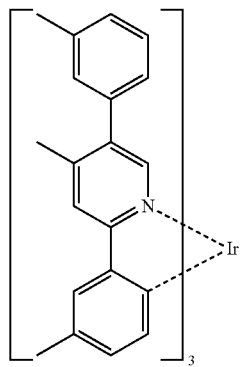
D-7
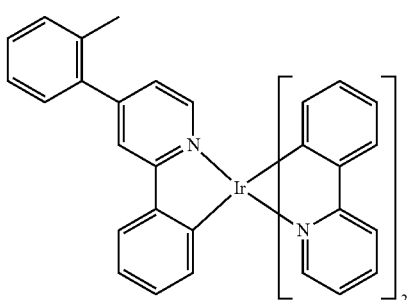
D-4
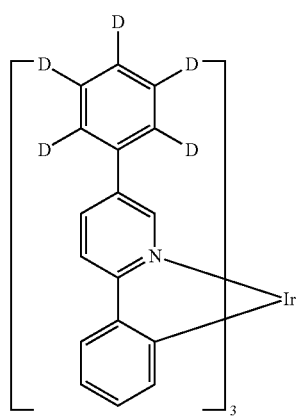
D-8
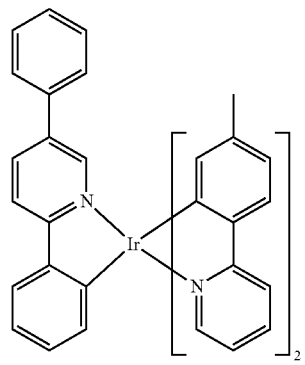

D-9
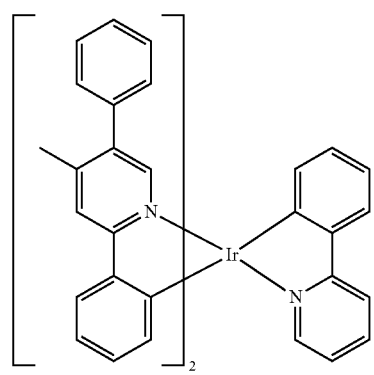
D-13
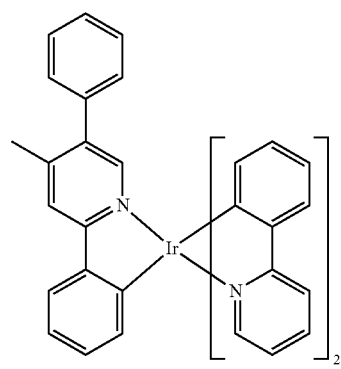
D-10
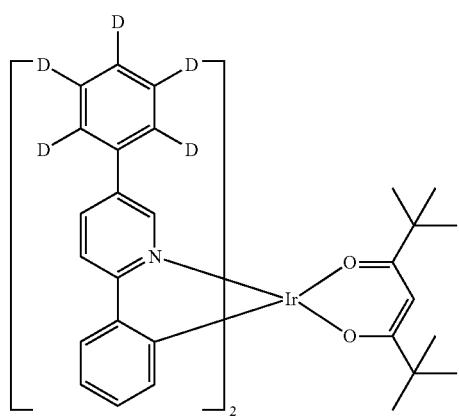
D-14
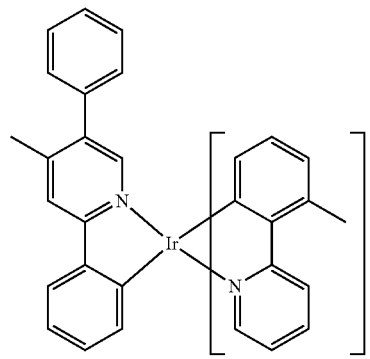
D-11
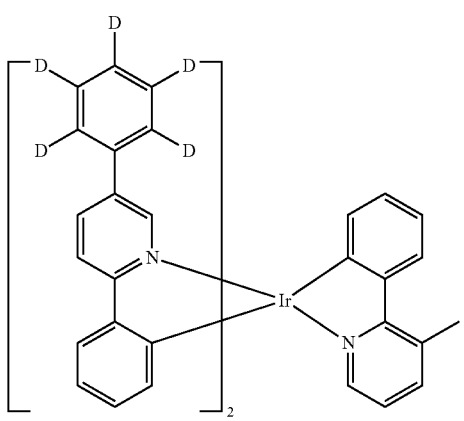
D-15
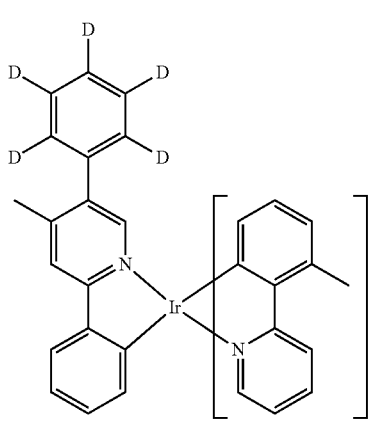
D-12
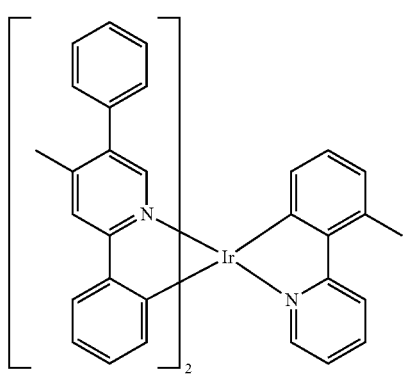
D-16
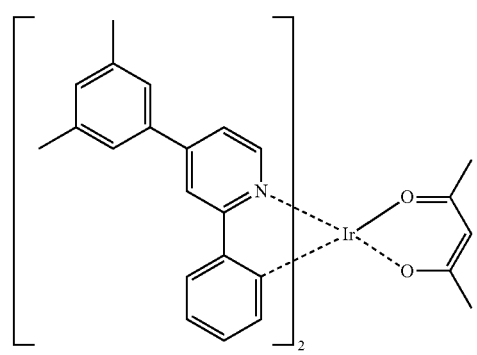

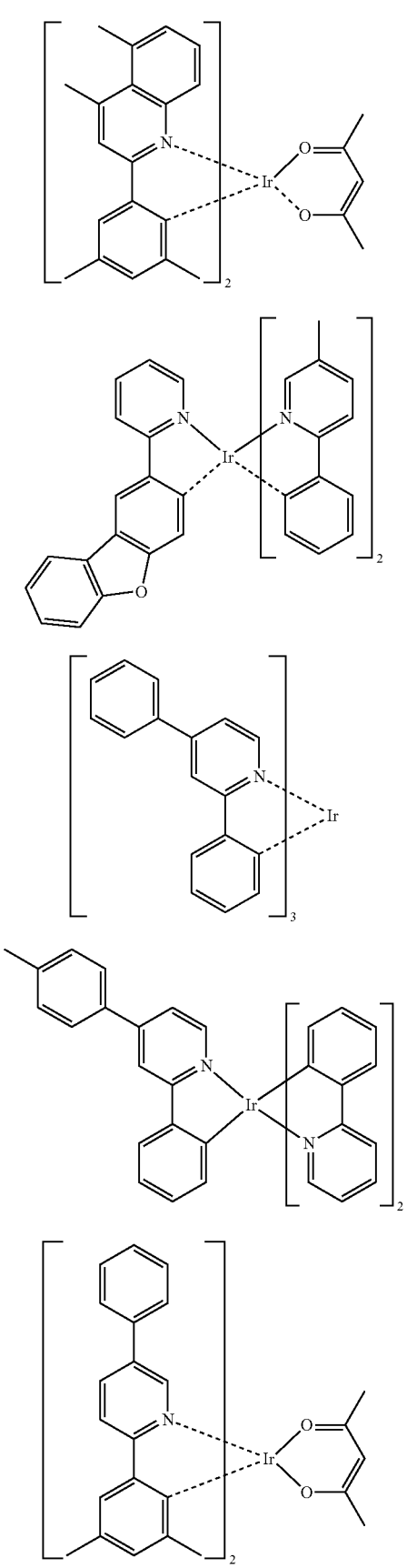
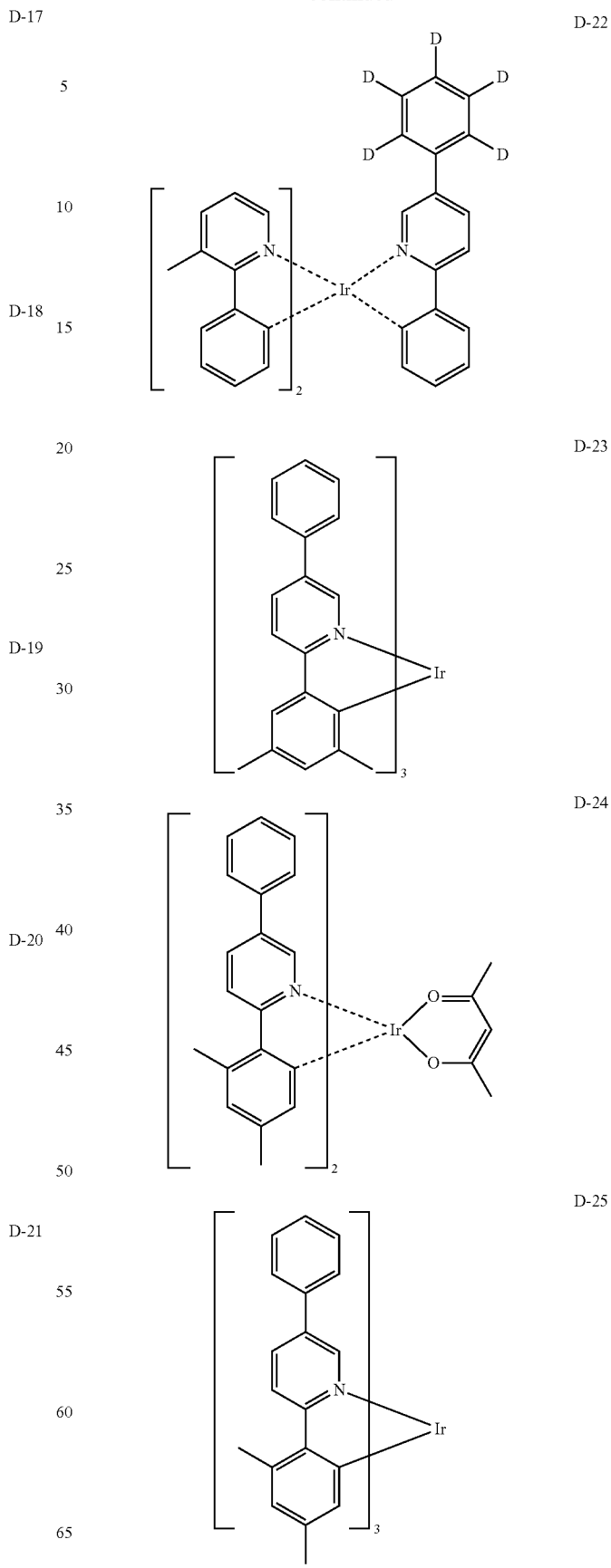

D-26
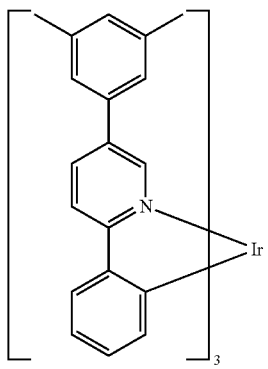
D-27
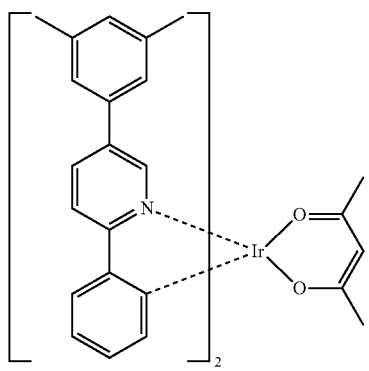
D-28
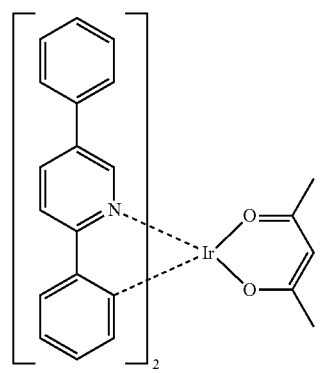
D-29
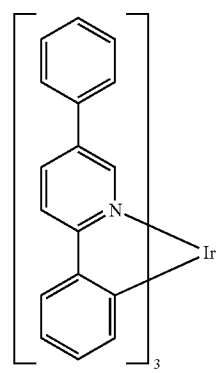
D-30
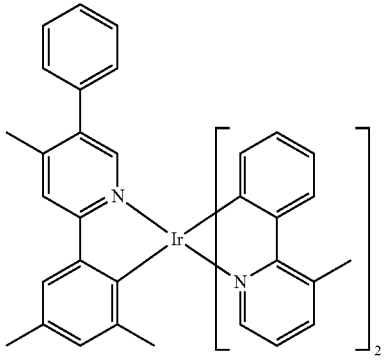
D-31
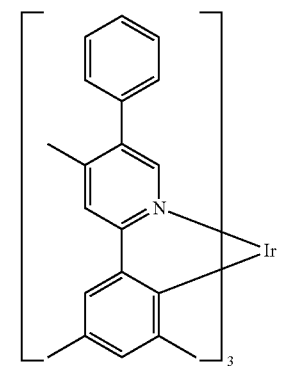
D-32
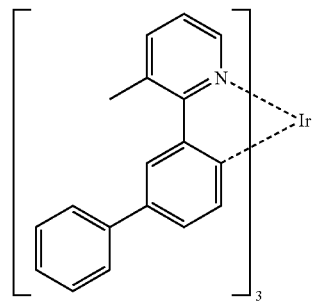
D-33
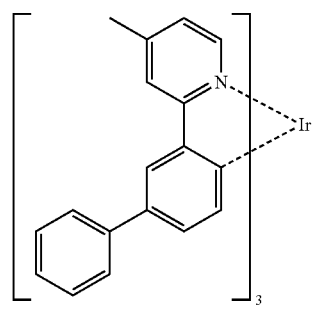
D-34
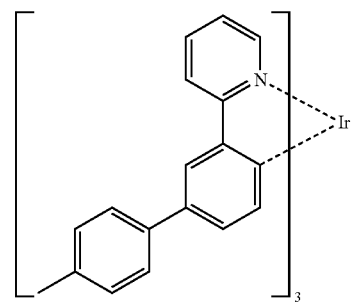

D-35 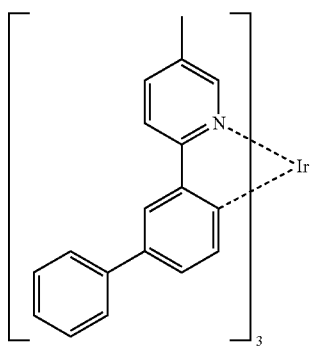
D-36 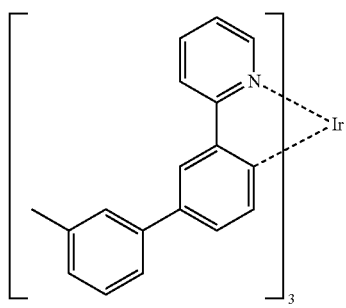
D-37 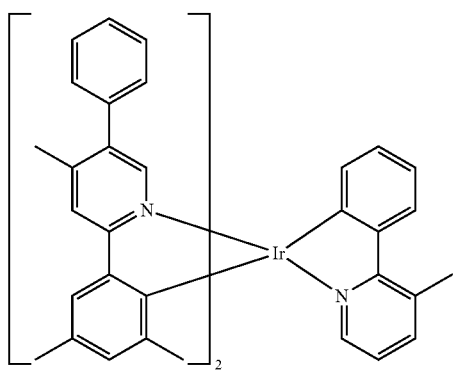
D-38 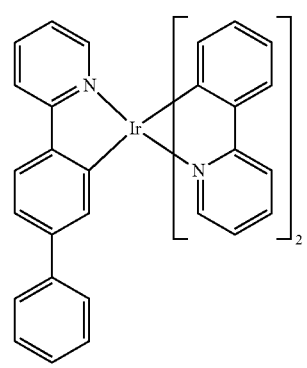
D-39 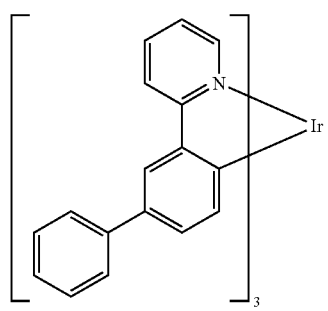
D-40 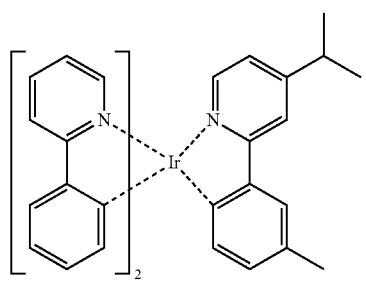
D-41 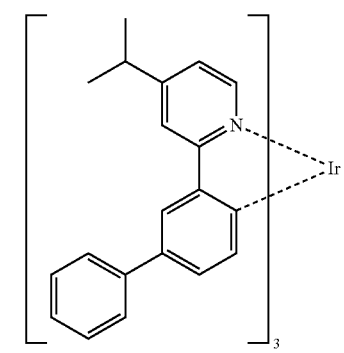
D-42 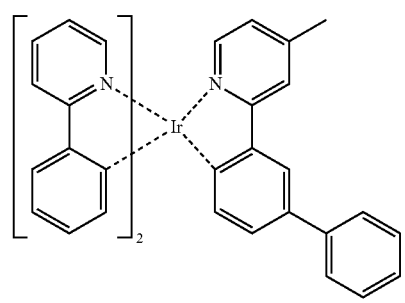
D-43 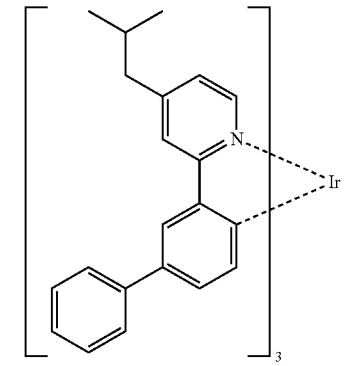

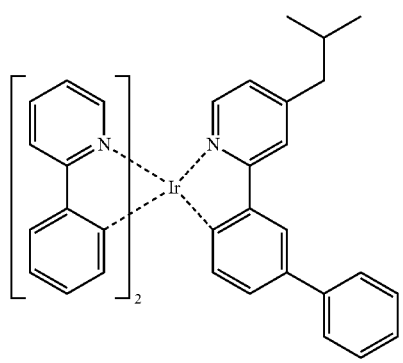 D-44
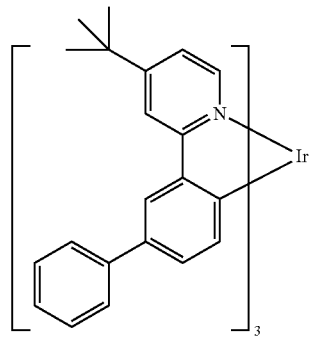 D-48
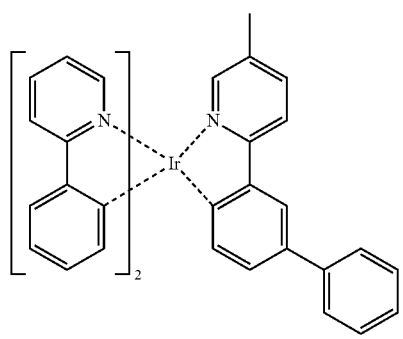 D-45
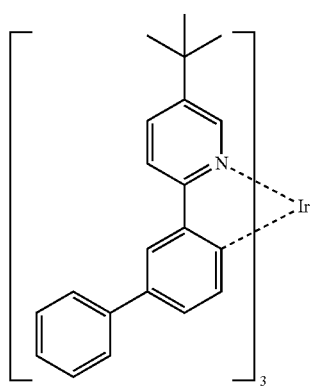 D-49
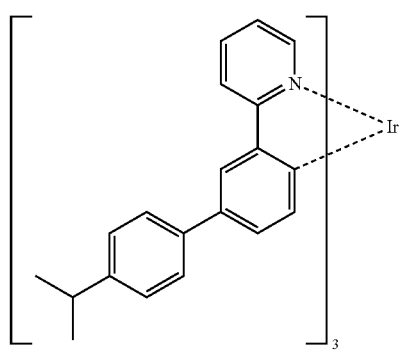 D-46
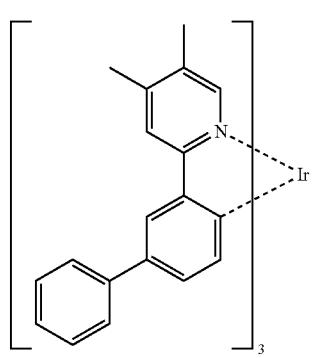 D-50
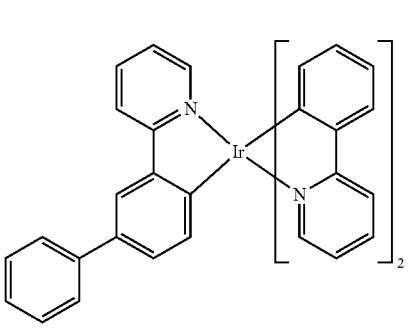 D-47
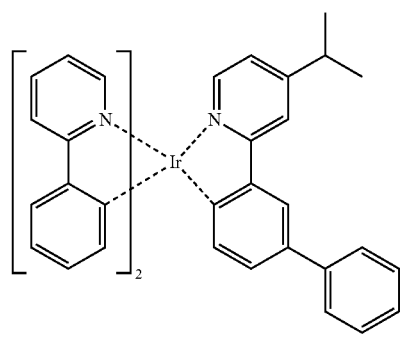 D-51

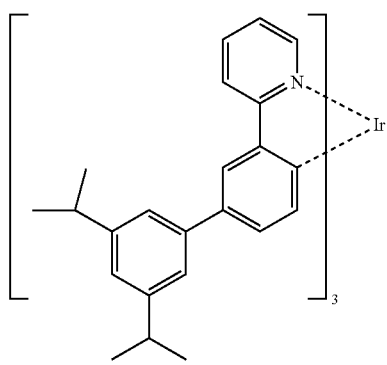
D-52
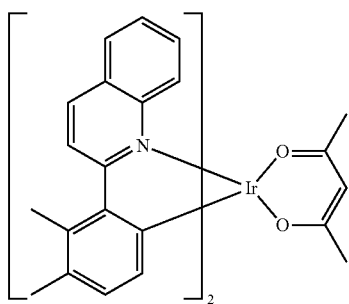
D-57
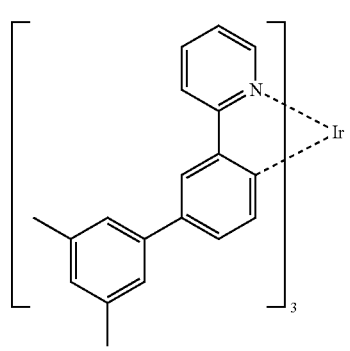
D-53
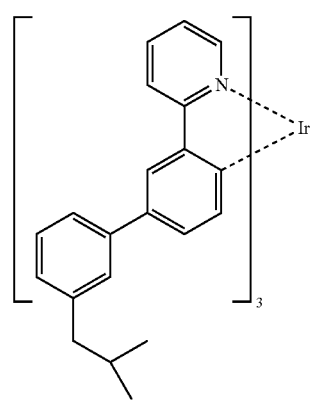
D-58
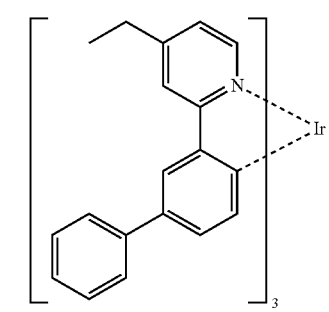
D-54
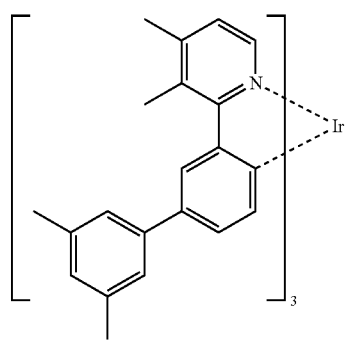
D-55
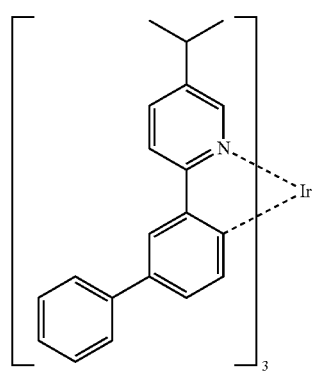
D-59
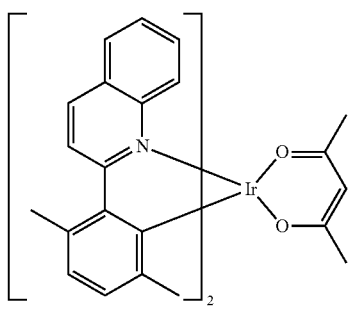
D-56
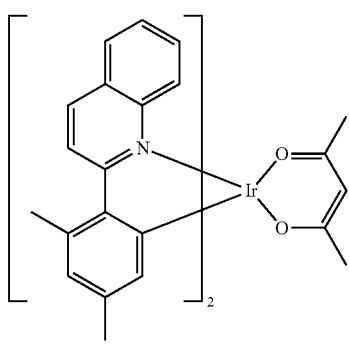
D-60

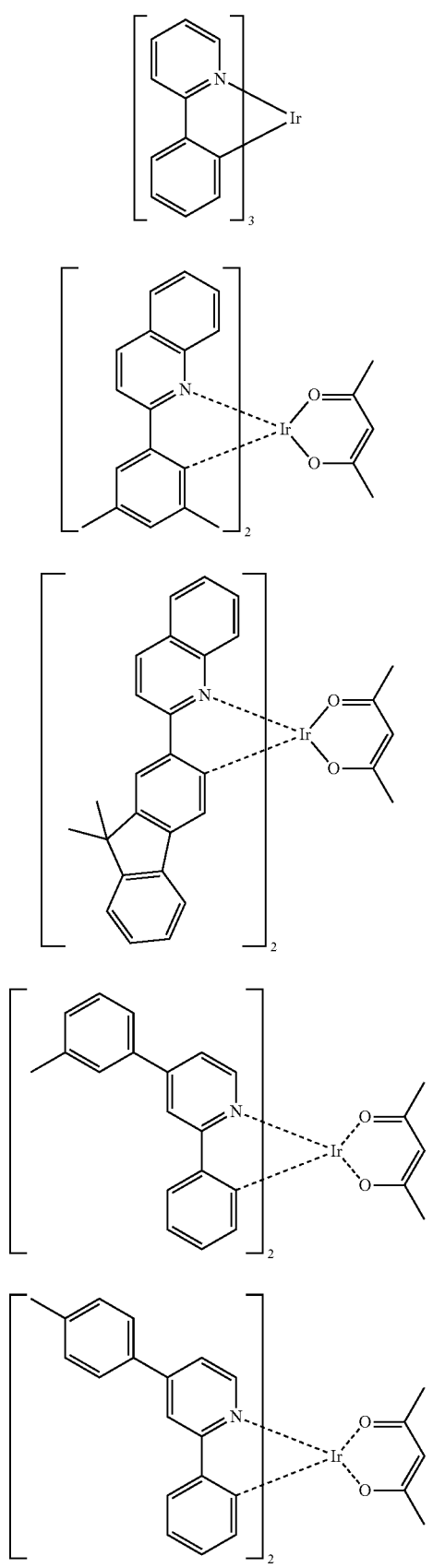
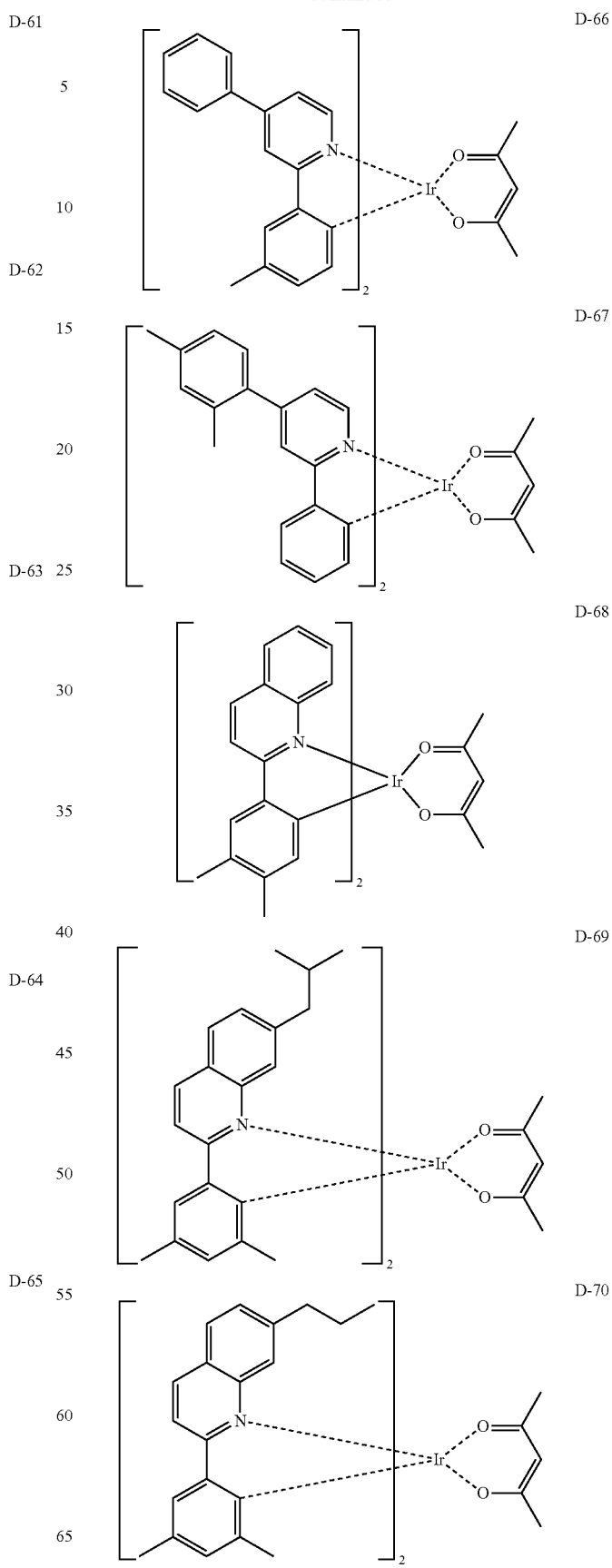

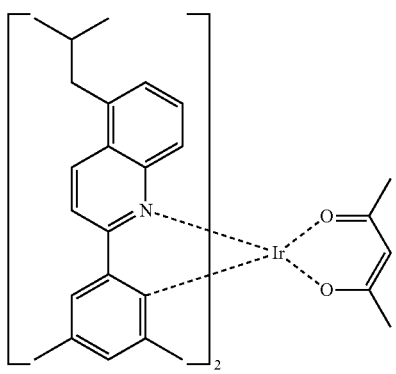
D-71
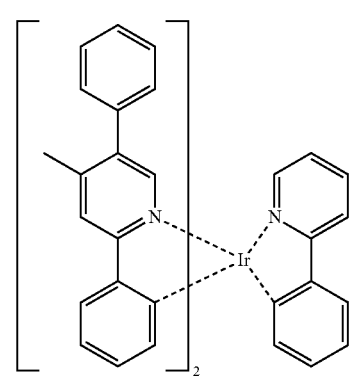
D-75
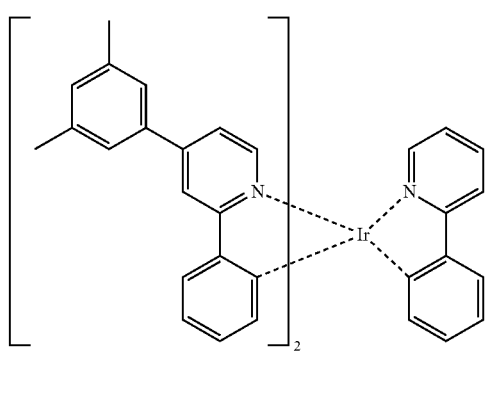
D-72
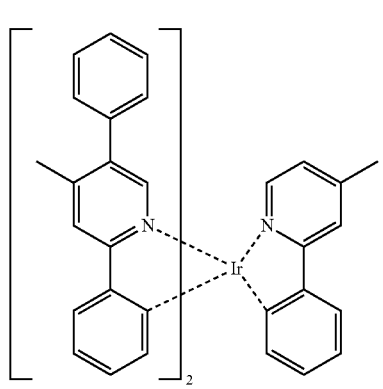
D-76
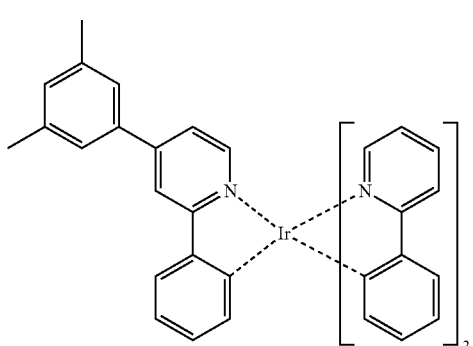
D-73
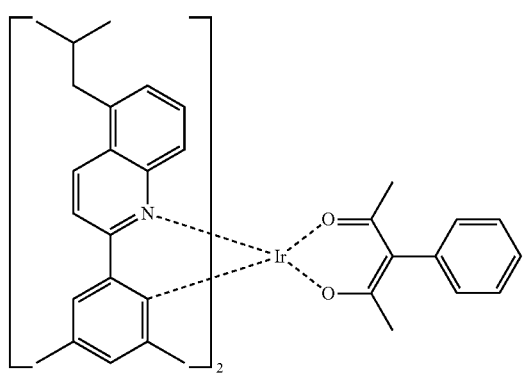
D-77
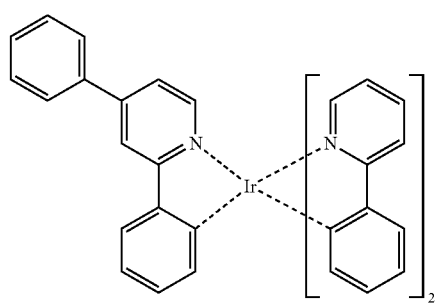
D-74
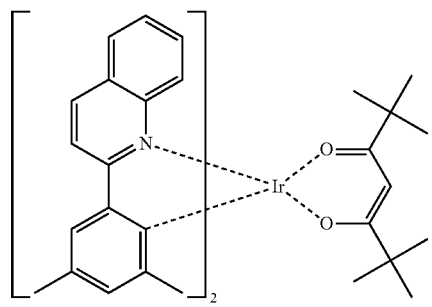
D-78

D-79 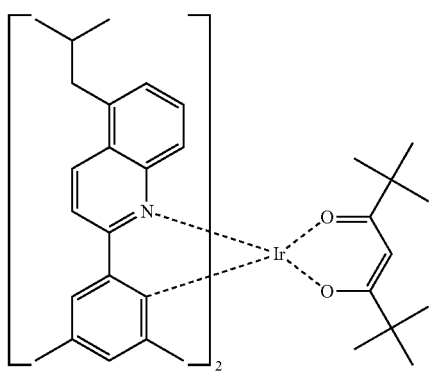
D-80 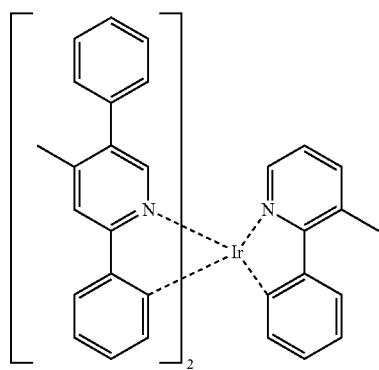
D-81 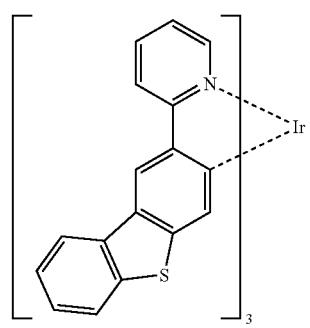
D-82 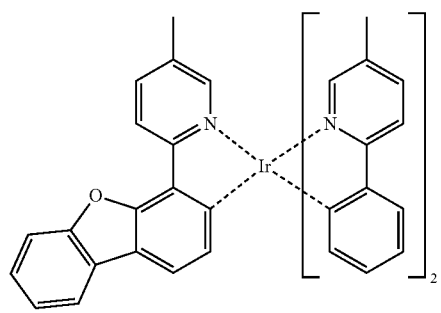
D-83 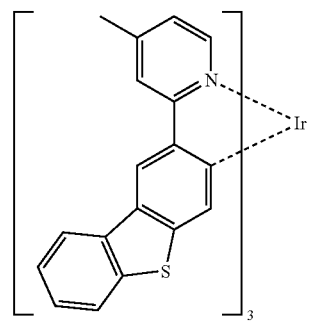
D-84 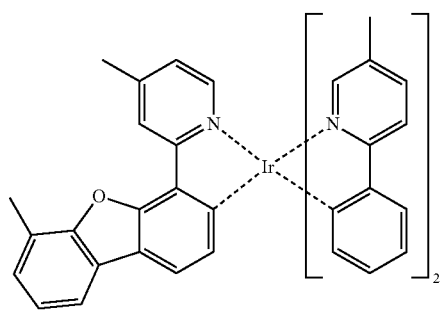
D-85 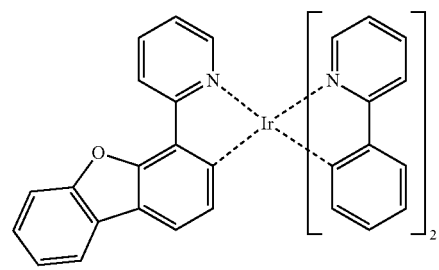
D-86 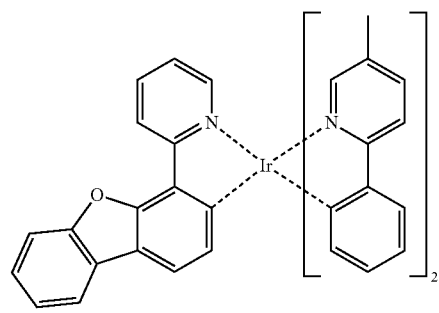
D-87 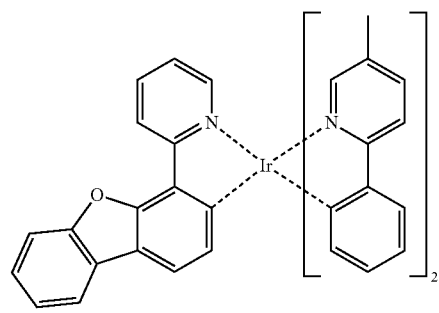

D-88
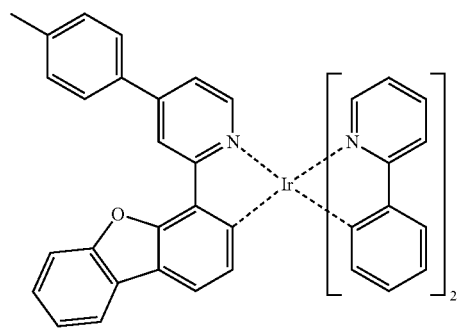
D-89
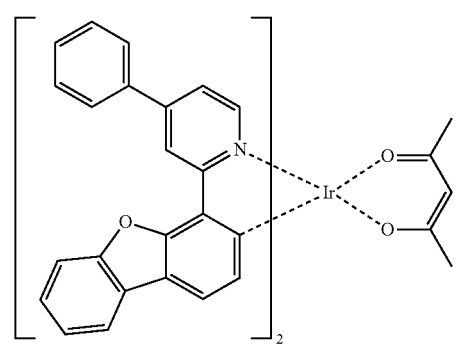
D-90
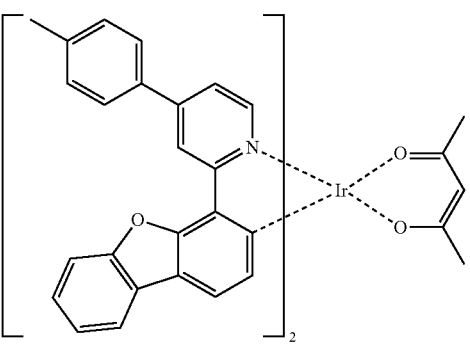
D-91
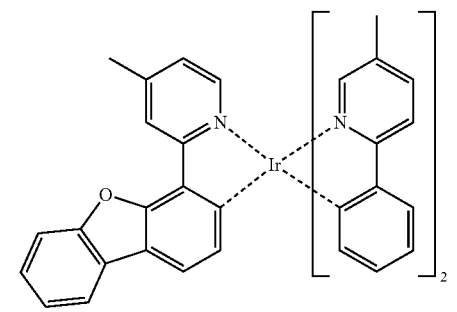
D-92
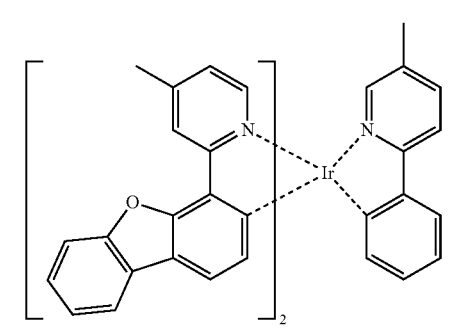
D-93
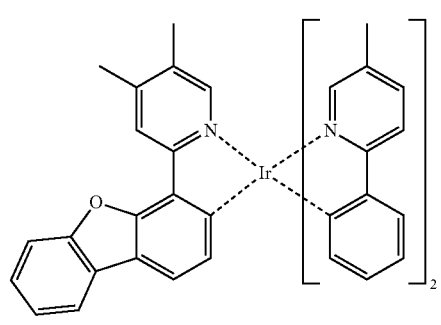
D-94
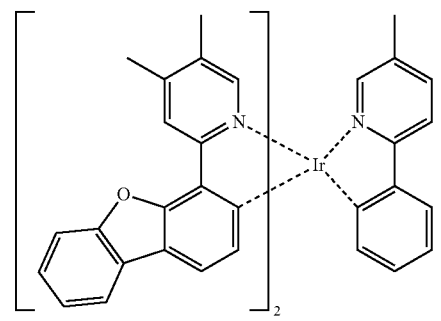
D-95
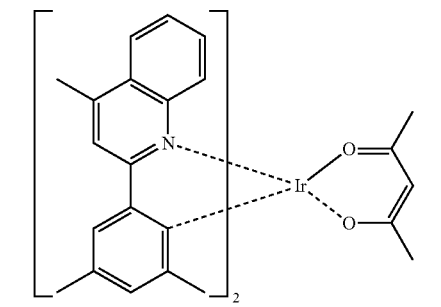
D-96
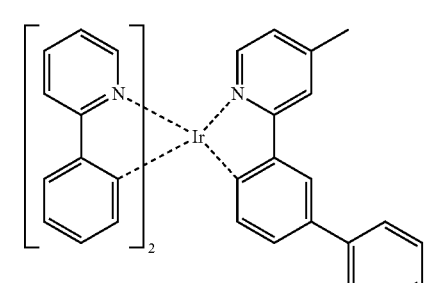
D-97
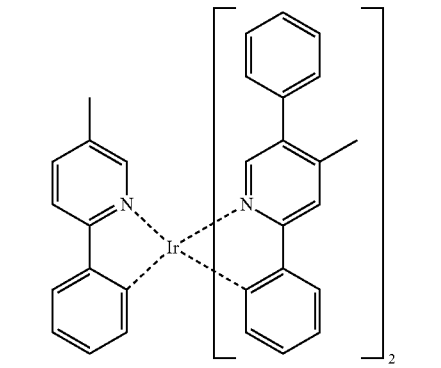

D-98
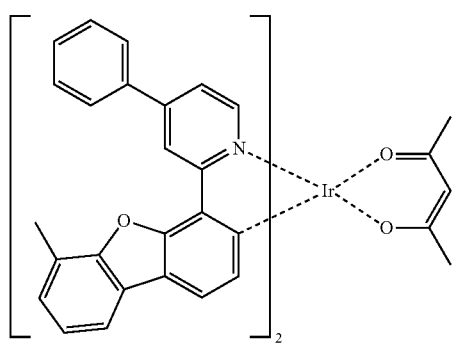
D-99
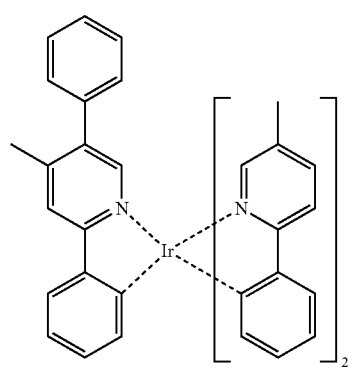
D-100
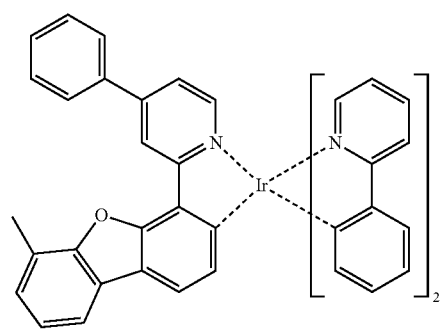
D-101
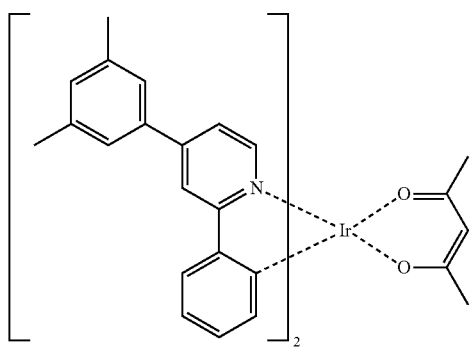
D-102
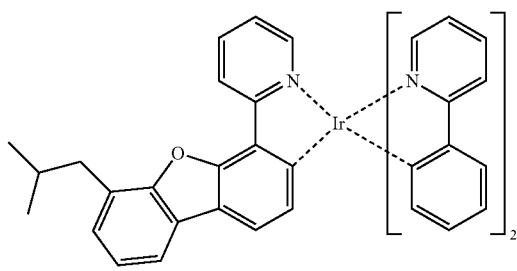
D-103
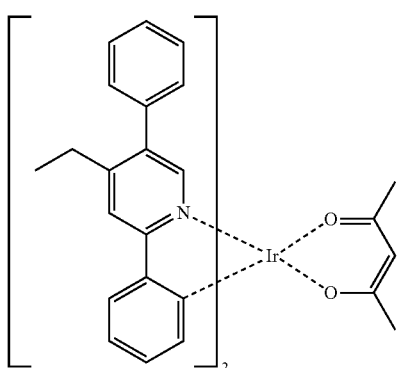
D-104
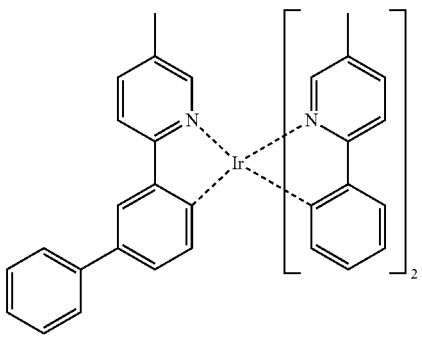
D-105
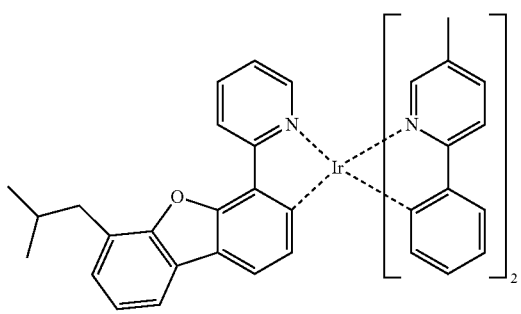

D-106
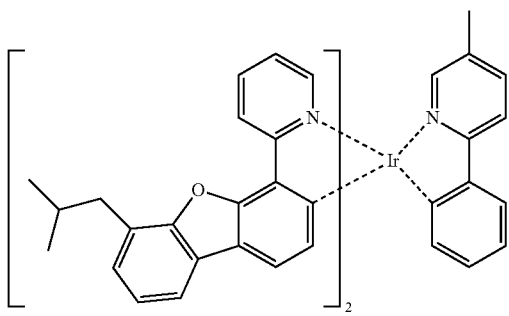
D-110
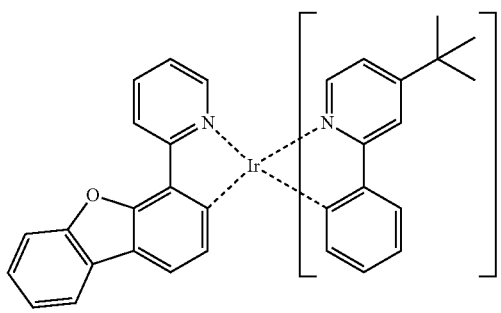
D-107
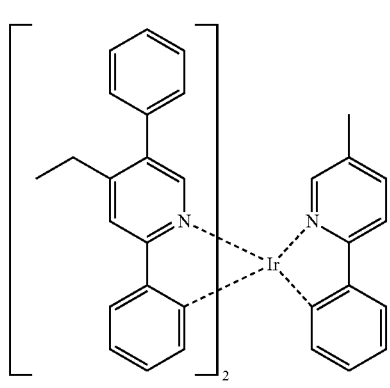
D-111
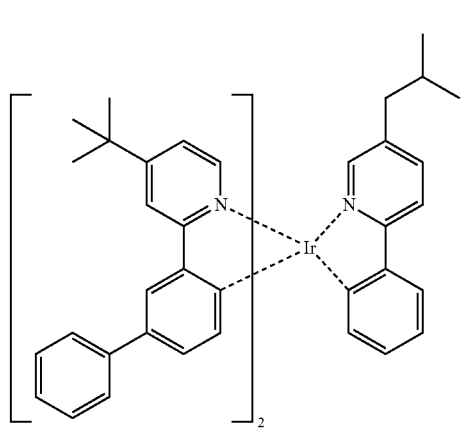
D-108
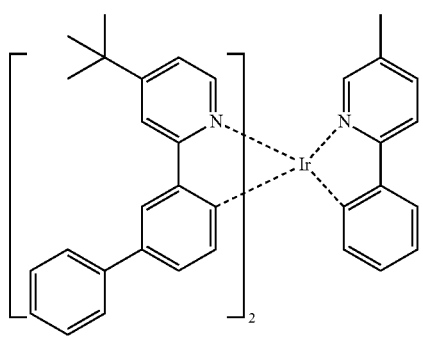
D-112
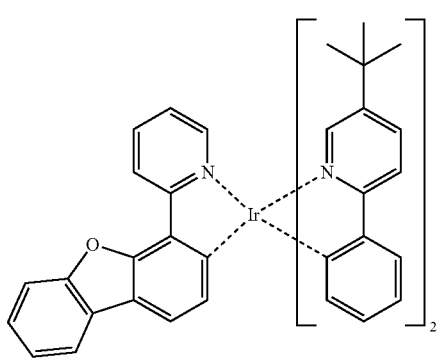
D-109
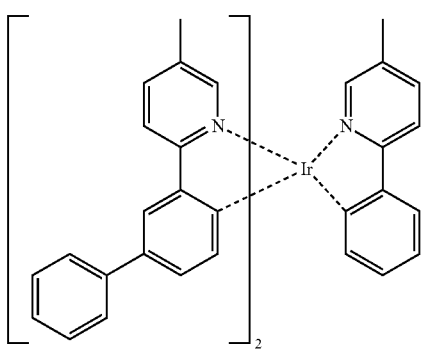
D-113
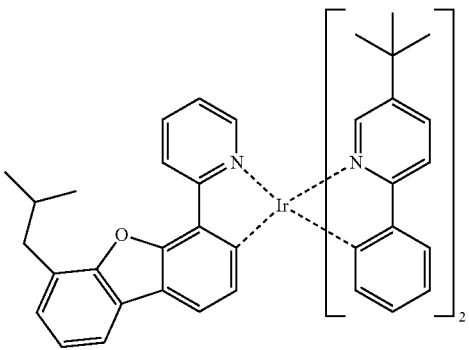

D-114
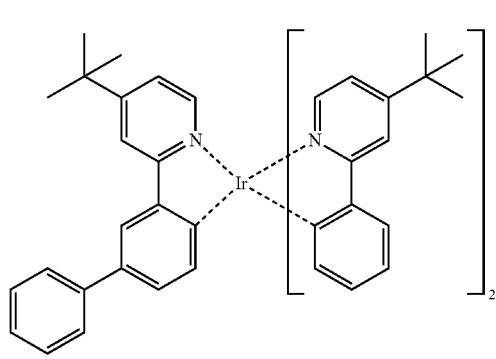
D-118
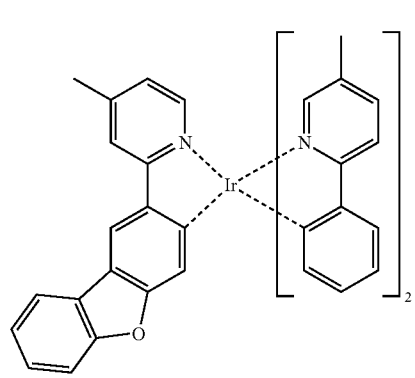
D-115
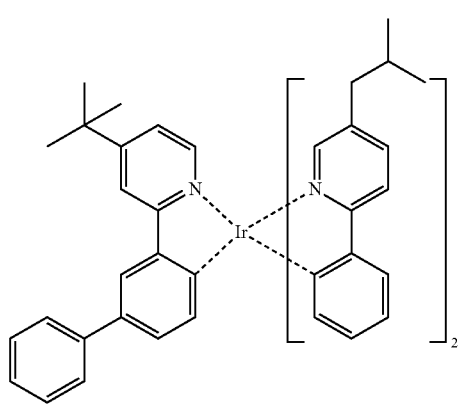
D-119
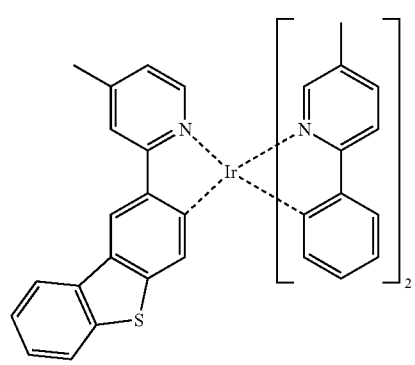
D-116
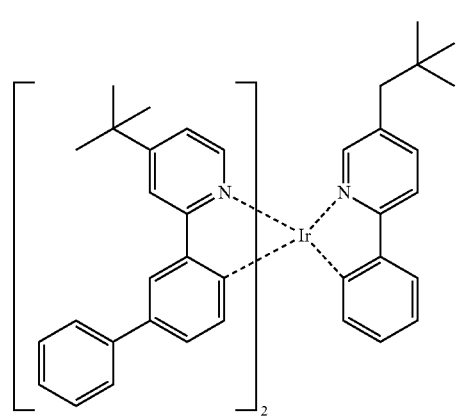
D-120
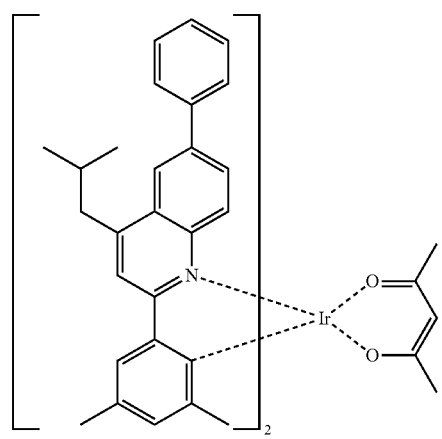
D-117
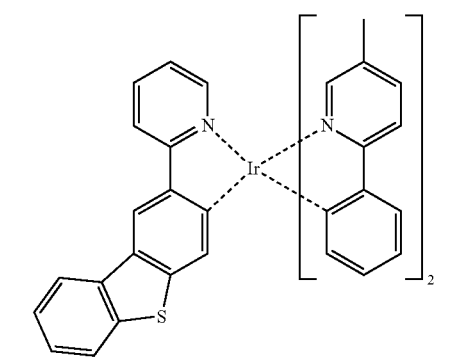
D-121
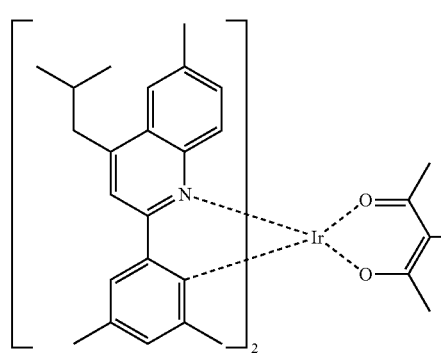

D-122
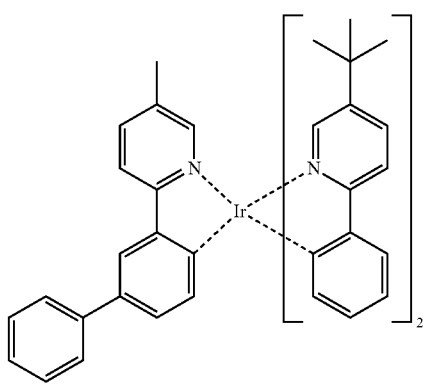
D-123
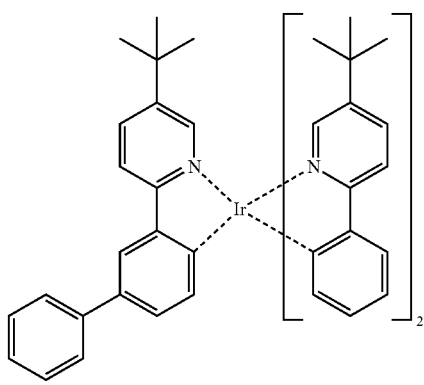
D-124
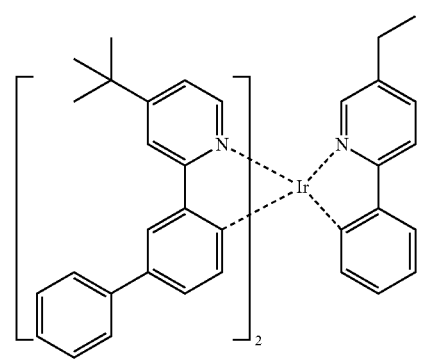
D-125
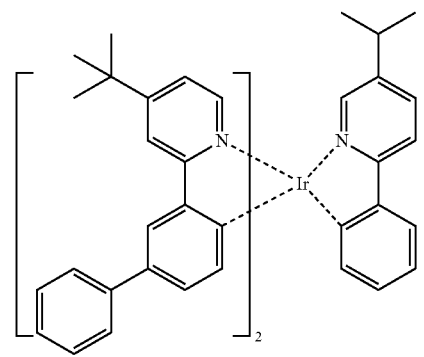
D-126
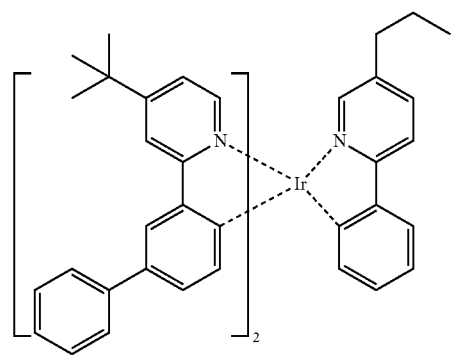
D-127
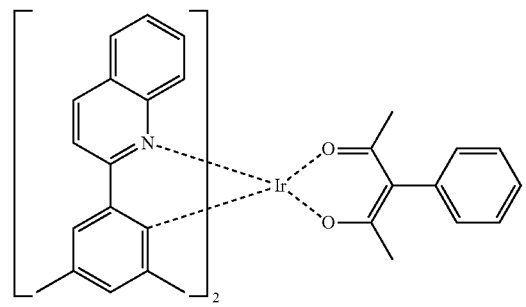
D-128
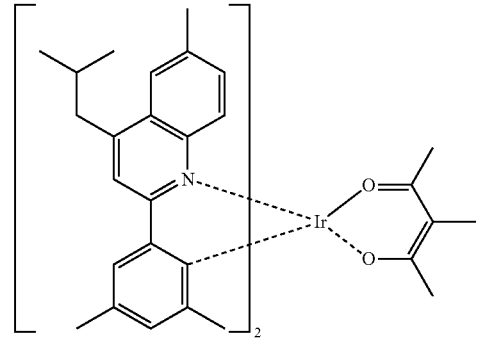
D-129
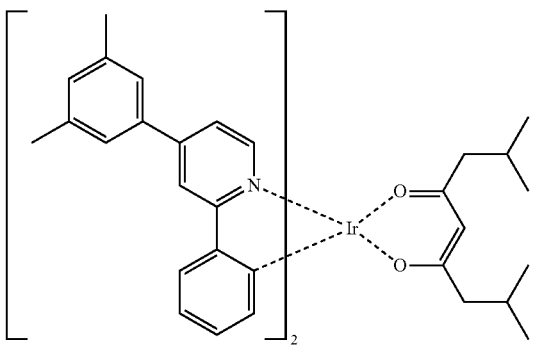

D-130
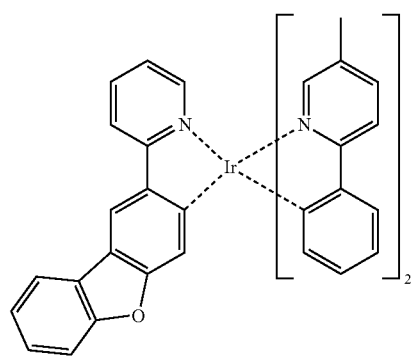
D-131
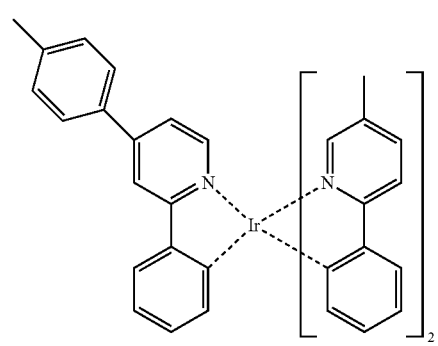
D-132
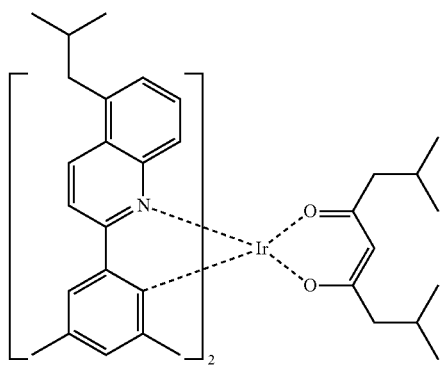
D-133
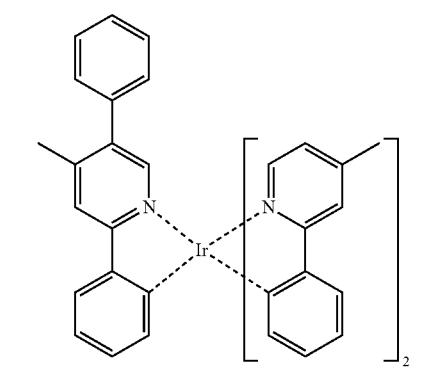
D-134
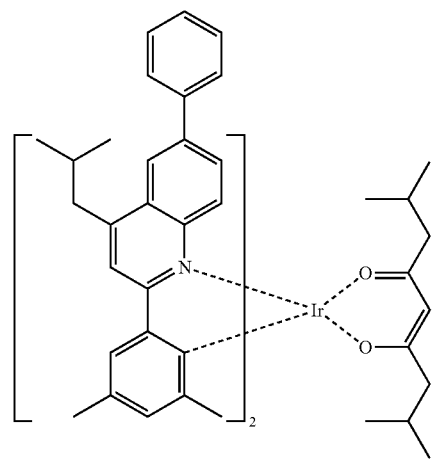
D-135
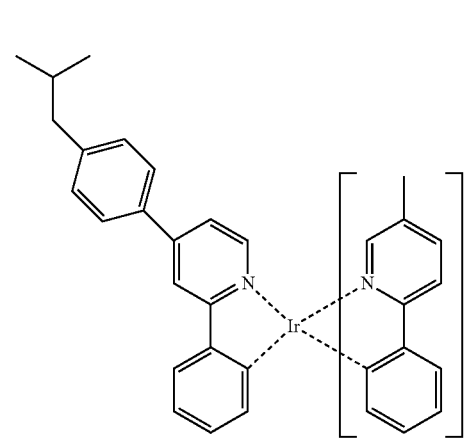
D-136
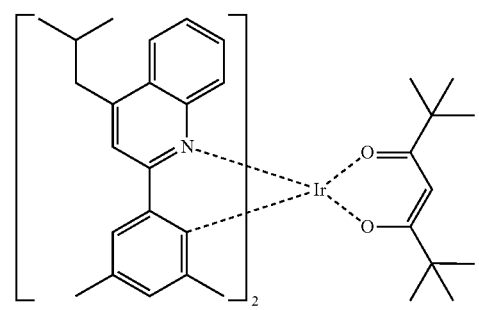
D-137
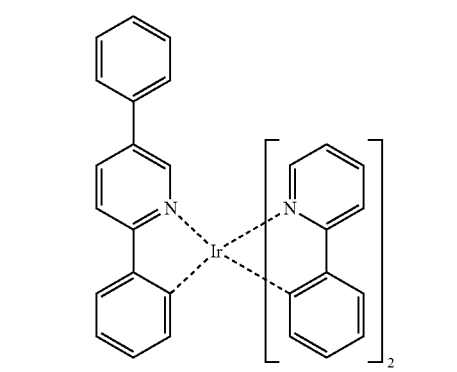

-continued
D-138
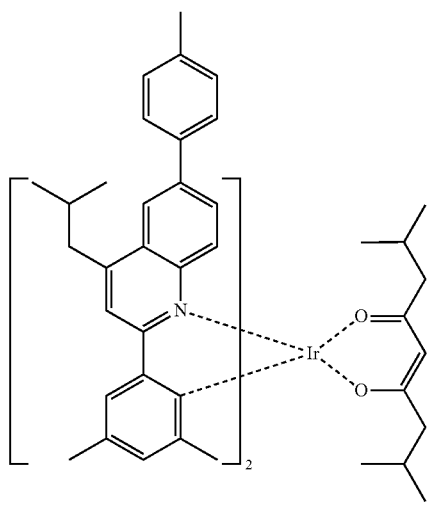
D-139
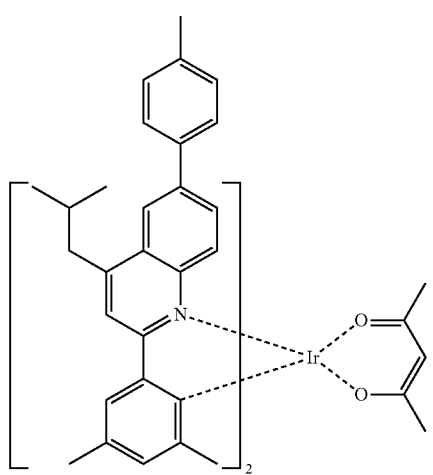
D-140
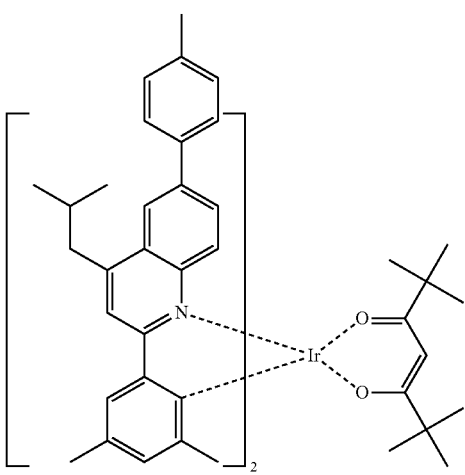
-continued
D-141
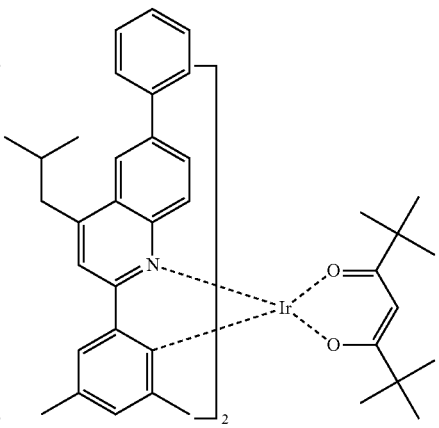
D-142
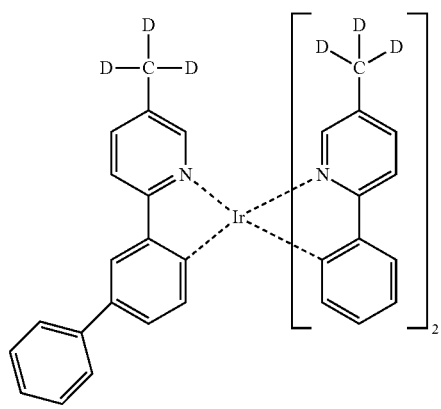
D-143
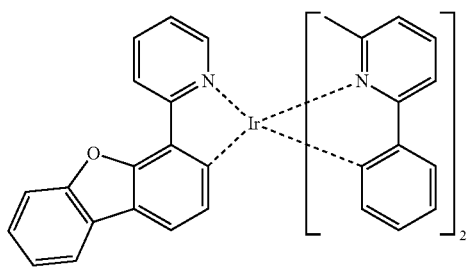
D-144
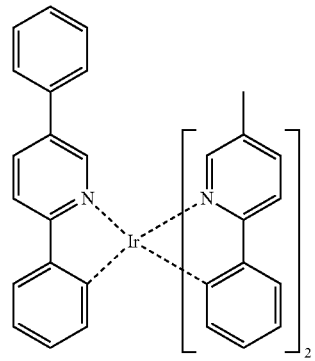

D-145

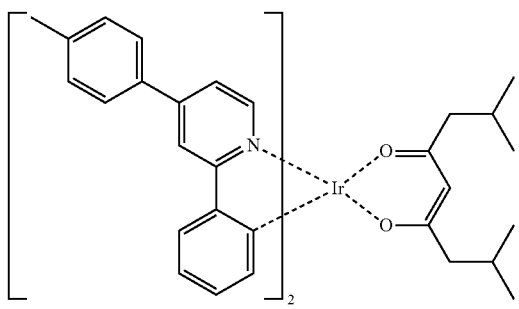

D-146

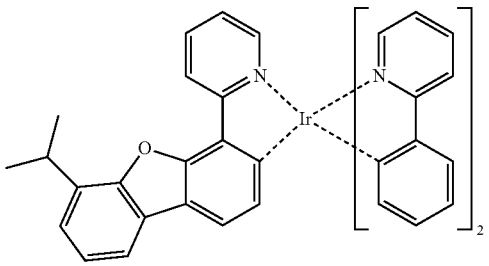

D-147

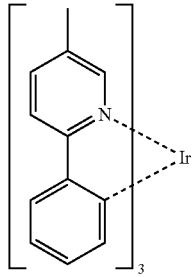

D-148

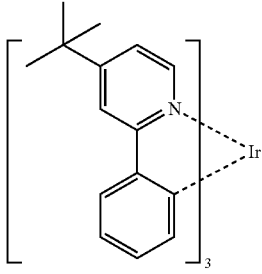

The organic electroluminescent device of the present disclosure may comprise the compound of formula 1, and further comprise at least one compound selected from the group consisting of arylamine-based compounds and styrylarylamine-based compounds, simultaneously.

According to one embodiment of the present disclosure, at least one layer of the emitting-layer in the organic electroluminescent device of the present disclosure may comprise at least one dopant compound and at least one host compound, wherein the host compound may be the compound represented by formula 1. Also, an electron buffer layer of the organic electroluminescent device may comprise the compound represented by formula 1.

According to one embodiment of the present disclosure, at least one layer of the light-emitting layer in the organic electroluminescent device of the present disclosure may comprise at least one dopant compound and at least two host compounds, wherein the first host compound in the host compounds may be the compound represented by formula 1, and wherein the second host compound in the host compounds may be the compound represented by formula 5. Also, an electron buffer layer of the organic electroluminescent device may comprise the compound represented by formula 1.

In the organic electroluminescent device of the present disclosure, the organic layer may comprise at least one organic electroluminescent compound represented by formula 1. Also, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal. The organic layer may further comprise one or more additional light-emitting layers and a charge generating layer.

In addition, the organic electroluminescent device of the present disclosure may emit white light by further comprising at least one light-emitting layer, which comprises a blue, red, or green electroluminescent compound known in the field, besides the compound of the present disclosure. If necessary, it may further comprise a yellow or orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer, and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used, but are not limited thereto.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the preparation method of the compounds of the present disclosure, and the properties of the device comprising the compounds will be explained in detail with reference to the representative compounds of the present disclosure. However, the present disclosure is not limited by the following examples.

Example 1: Preparation of Compound C-73

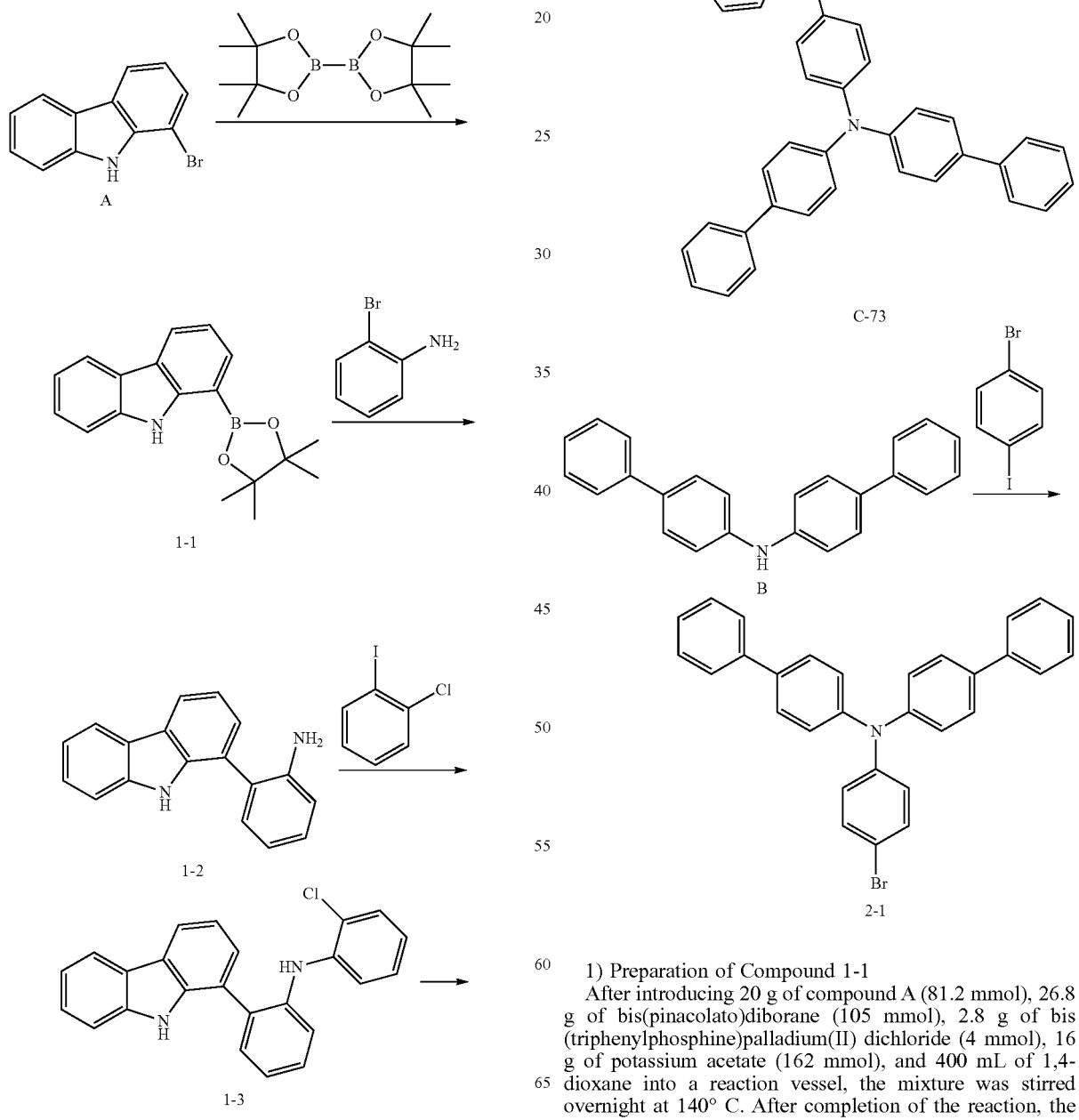

1) Preparation of Compound 1-1

After introducing 20 g of compound A (81.2 mmol), 26.8 g of bis(pinacolato)diborane (105 mmol), 2.8 g of bis(triphenylphosphine)palladium(II) dichloride (4 mmol), 16 g of potassium acetate (162 mmol), and 400 mL of 1,4-dioxane into a reaction vessel, the mixture was stirred overnight at 140° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 15.4 g of compound 1-1 (77%).

2) Preparation of Compound 1-2

After introducing 14 g of compound 1-1 (56.6 mmol), 6.1 mL of 2-bromoaniline (54 mmol), 2.6 g of tetrakis(triphenylphosphine)palladium (2.3 mmol), 19.6 g of potassium carbonate (142 mmol), 280 mL of toluene, 70 mL of ethanol, and 70 mL of distilled water into a reaction vessel, the mixture was stirred for 5 hours at 120° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 8.6 g of compound 1-2 (59%).

3) Preparation of Compound 1-3

After introducing 8.3 g of compound 1-2 (32 mmol), 4.3 mL of 1-chloro-2-iodobenzene (35 mmol), 289 mg of palladium(II) acetate (1.3 mmol), 1.27 mL of tri-tert-butylphosphine (2.6 mmol), 6.2 g of sodium tert-butoxide (64 mmol), and 160 mL of o-xylene into a reaction vessel, the mixture was stirred for 2 hours at 160° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 3.4 g of compound 1-3 (29%).

4) Preparation of Compound 1-4

After introducing 3.4 g of compound 1-3 (9.2 mmol), 1 g of palladium(II) acetate (4.6 mmol), 4.3 mL of tri-tert-butylphosphine (9.2 mmol), 12 g of cesium carbonate (36.8 mmol), and 60 mL of o-xylene into a reaction vessel, the mixture was stirred for 2 hours at 16° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 1.2 g of compound 1-4 (40%).

5) Preparation of Compound 2-1

After introducing 10 g of compound B (31 mmol), 13.2 g of 1-bromo-4-iodobenzene (46 mmol), 855 mg of tris(dibenzylideneacetone)dipalladium(0) (0.9 mmol), 757 mg of tri(o-tolyl)phosphine (2.5 mmol), 6 g of sodium tert-butoxide (62 mmol), and 310 mL of toluene into a reaction vessel, the mixture was stirred for 4 hours at 120° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 7 g of compound 2-1 (47%).

6) Preparation of Compound C-73

After introducing 2.7 g of compound 1-4 (8.1 mmol), 4.6 g of compound 2-1 (9.7 mmol), 223 mg of tris(dibenzylideneacetone)dipalladium(0) (0.2 mmol), 198 mg of tri(o-tolyl) phosphine (0.6 mmol), 1.6 g of sodium tert-butoxide (16 mmol), and 80 mL of toluene into a reaction vessel, the mixture was stirred for 2 hours at 120° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 4 g of compound C-73 (61%).

|      | MW    | UV     | PL     | M.P.    |
|------|-------|--------|--------|---------|
| C-73 | 727.9 | 393 nm | 459 nm | 258° C. |

Example 2: Preparation of Compound C-7

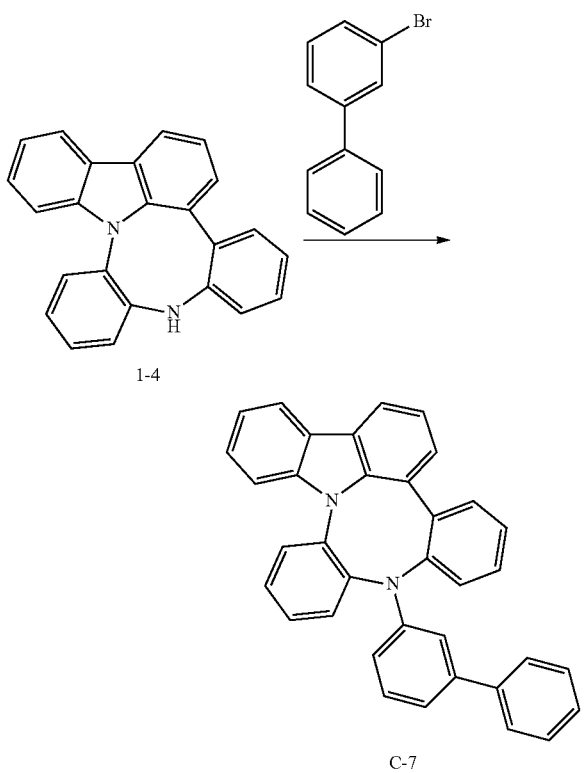

After introducing 3.1 g of compound 1-4 (9.3 mmol), which was prepared by the same method as in Example 1, 2.6 g of 3-bromo-1,1'-biphenyl (11.2 mmol), 256 mg of tris(dibenzylideneacetone)dipalladium(0) (0.28 mmol), 227 mg of tri(o-tolyl)phosphine (0.74 mmol), 1.8 g of sodium tert-butoxide (18.6 mmol), and 93 mL of toluene into a reaction vessel, the mixture was stirred for 3 hours at 120° C. After completion of the reaction, the reaction product was cooled to room temperature, and then was extracted with ethyl acetate. After drying the extracted organic layer with magnesium sulfate, the solvent was removed with a rotary evaporator. Thereafter, the resulting product was purified by column chromatography to obtain 2.8 g of compound C-7 (62%).

|     | MW    | UV     | PL     | M.P.    |
|-----|-------|--------|--------|---------|
| C-7 | 484.6 | 307 nm | 395 nm | 274° C. |

Example 3: Preparation of Compound C-91

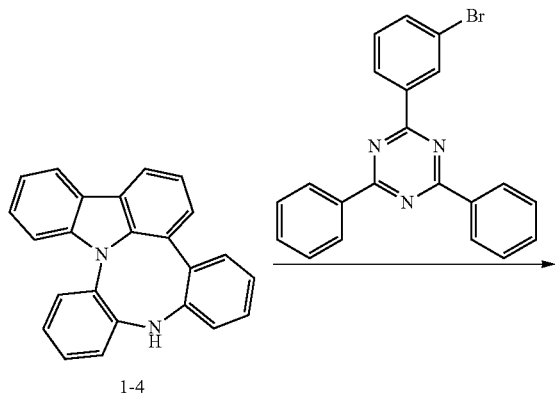

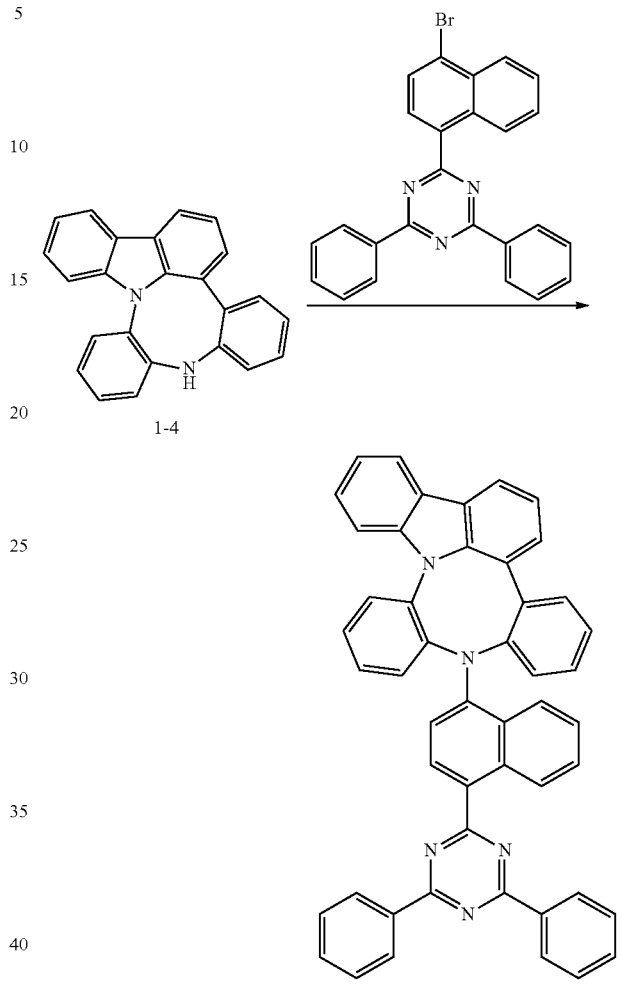

After introducing 3.5 g of compound 1-4 (10.5 mmol), which was prepared by the same method as in Example 1, 4.9 g of 2-(3-bromophenyl)-4,6-diphenyl-1,3,5-triazine (12.6 mmol), 385 mg of tris(dibenzylideneacetone)dipalladium(0) (0.4 mmol), 256 mg of tri(o-tolyl)phosphine (0.8 mmol), 2.0 g of sodium tert-butoxide (21 mmol), and 90 mL of toluene into a reaction vessel, the mixture was stirred for 2 hours at 130° C. After completion of the reaction, the reaction product was cooled to room temperature, and the solvent was removed with a rotary evaporator. Thereafter, the resulting product was purified by column chromatography to obtain 2.4 g of compound C-91 (36%).

|  | MW | UV | PL | M.P. |
| --- | --- | --- | --- | --- |
| C-91 | 640.10 | 308 nm | 428 nm | 198° C. |

Example 4: Preparation of Compound C-92

After introducing 2.7 g of compound 1-4 (8.1 mmol), which was prepared by the same method as in Example 1, 3.9 g of 2-(4-bromo-1-naphthalenyl)-4,6-diphenyl-1,3,5-triazine (8.9 mmol), 300 mg of tris(dibenzylideneacetone)dipalladium(0) (0.3 mmol), 333 mg of 2-dichlorohexylphosphino-2',6'-dimethoxybiphenyl (0.8 mmol), 2.0 g of sodium tert-butoxide (21 mmol), and 41 mL of o-xylene into a reaction vessel, the mixture was stirred for 2 hours at 150° C. After completion of the reaction, the reaction product was cooled to room temperature, and the solvent was removed with a rotary evaporator. Thereafter, the resulting product was purified by column chromatography to obtain 3.0 g of compound C-92 (54%).

|  | MW | UV | PL | M.P. |
| --- | --- | --- | --- | --- |
| C-92 | 690.10 | 390 nm | 457 nm | 318° C. |

Hereinafter, the luminescent properties of the organic light-emitting diode (OLED) device comprising the compound of the present disclosure will be explained in detail.

Device Example 1-1: Producing an OLED Device by a Co-Evaporation of First and Second Host Compounds of the Present Disclosure An OLED device was produced by using the organic electroluminescent compound according to the present disclosure. A transparent electrode indium tin oxide (ITO) thin film (10 Ω/sq) on a glass substrate for an OLED device (GEOMATEC CO., LTD., Japan) was subjected to an ultrasonic washing with acetone, ethanol, and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus, and was evaporated by applying an electric current to the cell, thereby forming a second hole injection layer having a thickness of 5 nm on the first hole injection layer. Compound HT-1 was then introduced into another cell of the vacuum vapor deposition apparatus, and was evaporated by applying an electric current to the cell, thereby forming a first hole transport layer having a thickness of 10 nm on the second hole injection layer. Compound HT-2 was then introduced into another cell of the vacuum vapor deposition apparatus, and was evaporated by applying an electric current to the cell, thereby forming a second hole transport layer having a thickness of 30 nm on the first hole transport layer. After forming the hole injection layer and the hole transport layer, a light-emitting layer was formed thereon as follows: Compound C-7 and compound B-51 were introduced into two cells of the vacuum vapor depositing apparatus, respectively, as a host, and compound D-1 was introduced into another cell as a dopant. The two host compounds were evaporated at the same rate of 1:1, while the dopant was evaporated at a different rate from the host compounds, so that the dopant was deposited in a doping amount of 15 wt % based on the total amount of the host and dopant to form a light-emitting layer having a thickness of 40 nm on the second hole transport layer. Compound ET-1 and compound EI-1 were then introduced into another two cells, and respectively evaporated at a rate of 4:6 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited by another vacuum vapor deposition apparatus. Thus, an OLED device was produced. Each of the materials used for producing the OLED device was purified by vacuum sublimation at $10^{-6}$ torr.

Comparative Example 1-1: Producing an OLED Device Comprising a Second Host Compound as a Sole Host An OLED device was produced in the same manner as in Device Example 1-1, except that only compound B-51 was used as a host for a light-emitting layer.

Comparative Example 1-2: Producing an OLED Device Comprising a Conventional Compound as a Host An OLED device was produced in the same manner as in Device Example 1-1, except for the following: A light-emitting layer having a thickness of 40 nm was deposited on the second hole transport layer by using compound CBP as a host and compound D-1 as a dopant; compound Balq was deposited as a hole blocking layer having a thickness of 10 nm; and thereafter, compound ET-1 and compound EI-1 were introduced into another two cells, and evaporated at a rate of 4:6 to form an electron transport layer having a thickness of 25 nm on the light-emitting layer.

The driving voltage, the luminous efficiency, the power efficiency, and the CIE color coordinate at a luminance of 1,000 nits of the OLED devices produced in Device Example 1-1, and Comparative Examples 1-1 and 1-2 are provided in Table 1 below.

TABLE 1

|  | Host | Voltage [V] | Luminous Efficiency [cd/A] | Power Efficiency [lm/W] | Color Coordinate (x, y) |
| --- | --- | --- | --- | --- | --- |
| Device Example 1-1 | C-7: B-51 | 3.4 | 52.6 | 48.6 | 0.310, 0.664 |
| Comparative Example 1-1 | B-51 | 3.9 | 33.6 | 27.1 | 0.325, 0.655 |
| Comparative Example 1-2 | CBP | 5.5 | 43.2 | 24.7 | 0.304, 0.669 |

Device Example 2-1: Producing an OLED Device by a Co-Evaporation of First and Second Host Compounds of the Present Disclosure An OLED device was produced in the same manner as in Device Examples 1-1, except for using compound D-13 as a dopant, and using the first and second host compounds shown in Table 2 below as a host.

Comparative Example 2-1: Producing an OLED Device Comprising a Second Host Compound as a Sole Host An OLED device was produced in the same manner as in Device Examples 2-1, except that only compound B-51 was used as a host for a light-emitting layer.

Comparative Example 2-2: Producing an OLED Device Comprising a Conventional Compound as a Host An OLED device was produced in the same manner as in Device Example 2-1, except for the following: A light-emitting layer having a thickness of 40 nm was deposited on the second hole transport layer by using compound CBP as a host and compound D-13 as a dopant; compound Balq was deposited as a hole blocking layer having a thickness of 10 nm; and thereafter, compound ET-1 and compound EI-1 were introduced into another two cells, and evaporated at a rate of 4:6 to form an electron transport layer having a thickness of 25 nm on the light-emitting layer.

The driving voltage, the luminous efficiency, the power efficiency, and the CIE color coordinate at a luminance of 1,000 nits of the OLED devices produced in Device Example 2-1, and Comparative Examples 2-1 and 2-2 are provided in Table 2 below.

TABLE 2

| | Host | Voltage [V] | Luminous Efficiency [cd/A] | Power Efficiency [lm/W] | Color Coordinate (x, y) |
|---|---|---|---|---|---|
| Device Example 2-1 | C-7: B-51 | 3.2 | 55.9 | 54.9 | 0.300, 0.661 |
| Comparative Example 2-1 | B-51 | 3.1 | 41.6 | 42.2 | 0.314, 0.653 |
| Comparative Example 2-2 | CBP | 6.0 | 43.9 | 23.0 | 0.292, 0.666 |

Device Example 3-1: Producing an OLED Device by an Evaporation of a Host Compound of the Present Disclosure An OLED device was produced in the same manner as in Device Example 1-1, except for the following: Compound C-91 was introduced into one cell of the vacuum vapor depositing apparatus as a host, and compound D-13 was introduced into another cell as a dopant. The dopant was evaporated at a different rate from the host compound, so that the dopant was deposited in a doping amount of 15 wt % based on the total amount of the host and dopant to form a light-emitting layer having a thickness of 40 nm on the second hole transport layer.

Comparative Example 3-1: Producing an OLED Device Comprising a Conventional Compound as a Host An OLED device was produced in the same manner as in Device Example 3-1, except for the following: A light-emitting layer having a thickness of 40 nm was deposited on the second hole transport layer by using compound CBP as a host and compound D-13 as a dopant; compound Balq was deposited as a hole blocking layer having a thickness of 10 nm; and thereafter, compound ET-1 and compound EI-1 were introduced into another two cells, and evaporated at a rate of 4:6 to form an electron transport layer having a thickness of 25 nm on the light-emitting layer.

The driving voltage, the luminous efficiency, the power efficiency, and the CIE color coordinate at a luminance of 1,000 nits of the OLED devices produced in Device Example 3-1 and Comparative Example 3-1 are provided in Table 3 below.

TABLE 3

| | Host | Voltage [V] | Luminous Efficiency [cd/A] | Power Efficiency [lm/W] | Color Coordinate (x, y) |
|---|---|---|---|---|---|
| Device Example 3-1 | C-91 | 3.8 | 62.0 | 50.7 | 0.301, 0.663 |
| Comparative Example 3-1 | CBP | 5.8 | 42.7 | 23.1 | 0.295, 0.665 |

Device Example 4-1: Producing an OLED Device by an Evaporation of a Host Compound of the Present Disclosure An OLED device was produced in the same manner as in Device Example 1-1, except for the following: Compound C-91 was introduced into one cell of the vacuum vapor depositing apparatus as a host, and compound D-74 was introduced into another cell as a dopant. The dopant was evaporated at a different rate from the host compound, so that the dopant was deposited in a doping amount of 10 wt % based on the total amount of the host and dopant to form a light-emitting layer having a thickness of 40 nm on the second hole transport layer.

Comparative Example 4-1: Producing an OLED Device Comprising a Conventional Compound as a Host An OLED device was produced in the same manner as in Device Example 4-1, except for the following: A light-emitting layer having a thickness of 40 nm was deposited on the second hole transport layer by using compound CBP as a host and compound D-74 as a dopant; compound Balq was deposited as a hole blocking layer having a thickness of 10 nm; and thereafter, compound ET-1 and compound EI-1 were introduced into another two cells, and evaporated at a rate of 4:6 to form an electron transport layer having a thickness of 25 nm on the light-emitting layer.

The driving voltage, the luminous efficiency, the power efficiency, and the CIE color coordinate based on 10 mA/cm$^2$ of the OLED devices produced in Device Example 4-1 and Comparative Example 4-1 are provided in Table 4 below.

TABLE 4

| | Host | Voltage [V] | Luminous Efficiency [cd/A] | Power Efficiency [lm/W] | Color Coordinate (x, y) |
|---|---|---|---|---|---|
| Device Example 4-1 | C-91 | 5.1 | 76.0 | 46.7 | 419, 565 |
| Comparative Example 4-1 | CBP | 7.7 | 66.1 | 27.2 | 422, 563 |

From Tables 1 to 4 above, it can be seen that the OLED device comprising the compound of the present disclosure as a host not only has excellent luminance property, but also improved power consumption by lowering the driving voltage and increasing luminous and power efficiencies, compared to the OLED device using conventional luminescent material.

Comparative Example 5-1: Producing a Blue Light-Emitting OLED Device not Comprising an Electron Buffer Layer An OLED device was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to 10$^{-7}$ torr. Thereafter, an electric current was applied to the cell to evaporate the introduced material, thereby forming the first hole injection layer having a thickness of 60 nm on the ITO substrate. Compound HI-2 was then introduced into another cell of the vacuum vapor deposition apparatus, and an electric current was applied to the cell to evaporate the introduced material, thereby forming the second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming the first hole transport layer having a thickness of 20 nm on the second hole injection layer. Compound HT-3 was then introduced into another cell of the vacuum vapor deposition apparatus, and an electric current was applied to the cell to evaporate the introduced material, thereby forming the second hole transport layer having a thickness of 5 nm on the first hole transport layer. After forming the hole injection layers and the hole transport layers, a light-emitting layer was then deposited as follows. Compound BH-1 as a host was introduced into one cell of the vacuum vapor deposition apparatus and compound BD-1 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, compound ET-2 as an electron transport material was introduced into one cell of the vacuum vapor deposition apparatus, and compound EI-1 was introduced into another cell of the vacuum vapor deposition apparatus. The two materials were evaporated at the same rate and doped in a doping amount of 50 wt %, respectively, to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

Device Examples 5-1 and 5-2: Producing a Blue Light-Emitting OLED Device Comprising the Compound of the Present Disclosure as an Electron Buffer Material An OLED device was produced in the same manner as in Comparative Example 5-1, except that the thickness of an electron transport layer was reduced to 25 nm and an electron buffer layer having a thickness of 5 nm was inserted between the light-emitting layer and the electron transport layer.

The driving voltage, the luminous efficiency, and the CIE color coordinate at a luminance of 1,000 nits of the OLED devices produced in Comparative Example 5-1 and Device Examples 5-1 and 5-2 are provided in Table 5 below.

TABLE 5

|  | Electron Buffer Material | Voltage (V) | Luminous Efficiency (cd/A) | Color Coordinate (x) | Color Coordinate (y) |
| --- | --- | --- | --- | --- | --- |
| Comparative Example 5-1 | — | 4.2 | 5.8 | 139 | 88 |
| Device Example 5-1 | C-91 | 4.0 | 6.6 | 140 | 89 |
| Device Example 5-2 | C-92 | 4.1 | 6.2 | 140 | 90 |

From Table 5 above, it can be seen that the OLED device comprising the compound of the present disclosure as an electron buffer material improves the power consumption by lowering the driving voltage and increasing luminous efficiency, compared to the OLED device not comprising an electron buffer material.

The compounds used in the Device Examples and the Comparative Examples are provided in Table 6 below.

TABLE 6

| Hole Injection Layer/ Hole Transport Layer | |
| --- | --- |
| | H1-1 |

TABLE 6-continued
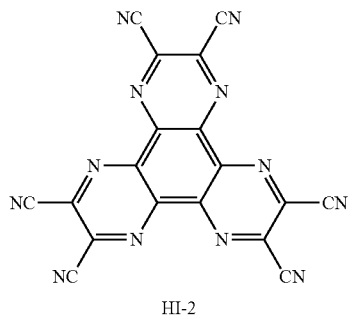
HI-2
HT-1
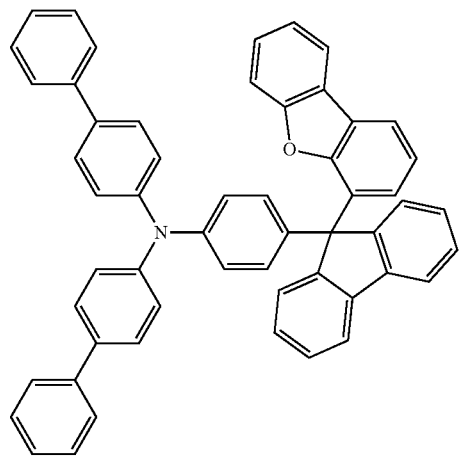
HT-2
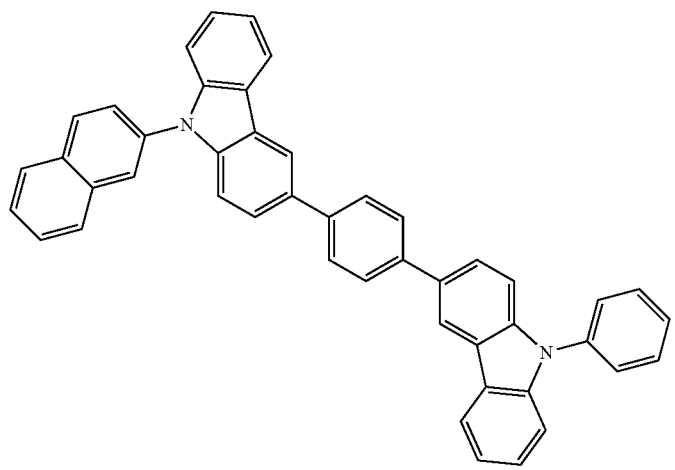
HT-3

TABLE 6-continued
Light-Emitting Layer
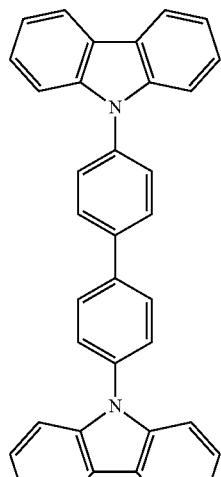
CBP
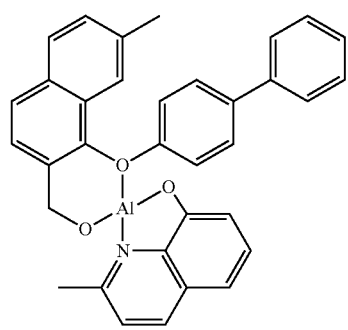
Balq
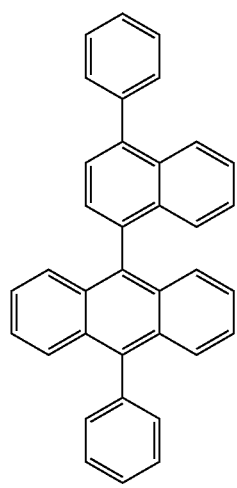
BH-1

TABLE 6-continued
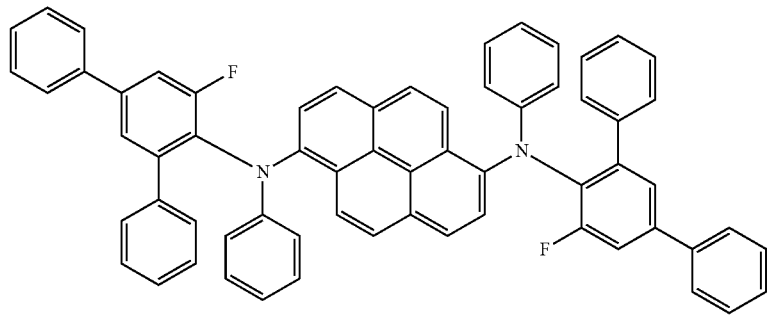
BD-1
Electron Transport Layer/
Electron Injection Layer
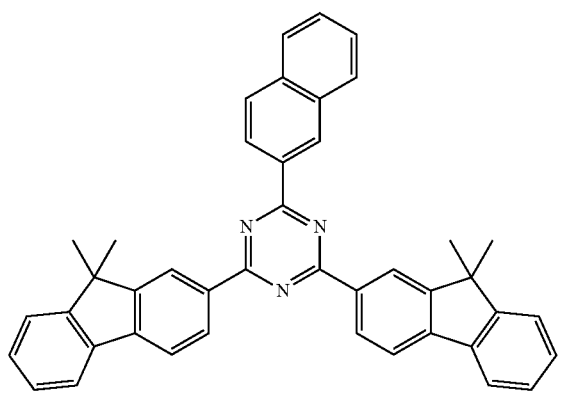
ET-1
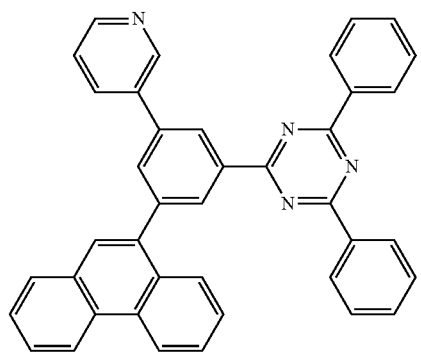
ET-2
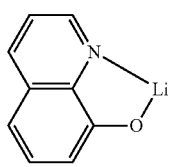
EI-1

The invention claimed is:
1. An organic electroluminescent compound represented by the following formula 1:

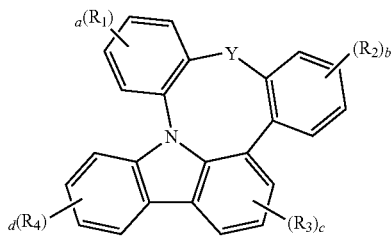

(1)

wherein
Y represents S, O or NR$_5$;
R$_1$ to R$_5$, each independently, represent deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or are linked to adjacent R$_1$ to R$_5$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;
the heteroaryl contains at least one heteroatom selected from B, N, O, S, Si, and P;
a, b and d, each independently, represent an integer of 0 to 4, c represents an integer of 0 to 3; where if a to d, each independently, represent an integer of 2 or more, each of R$_1$ to R$_4$ may be the same or different; and
with the proviso, when Y represents NR$_5$ and a represents 2, two R$_1$ are not fused with the aryl ring to which they are attached to form a carbazole ring.

2. The organic electroluminescent compound according to claim 1, wherein the substituents of the substituted (C1-C30)alkyl, the substituted (C6-C30)aryl, the substituted (3- to 30-membered)heteroaryl, the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic or aromatic ring, or the combination thereof, in R$_1$ to R$_5$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered) heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered)heteroaryl; a tri(C1-C30) alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30) arylcarbonyl; a di(C6-C30)arylboronyl; a di(C1-C30)alkyl-boronyl; a (C1-C30)alkyl(C6-C30)arylboronyl; a (C6-C30) aryl(C1-C30)alkyl; and a (C1-C30)alkyl(C6-C30)aryl.

3. The organic electroluminescent compound according to claim 1, wherein formula 1 is represented by the following formula 2:

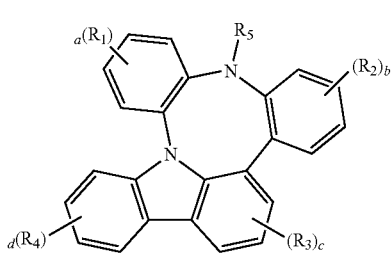

(2)

wherein
R$_1$ to R$_4$, each independently, represent a substituted or unsubstituted (C6-C25)aryl, a substituted or unsubstituted (5- to 25-membered)heteroaryl, or a substituted or unsubstituted di(C6-C25)arylamino; or are linked to adjacent R$_1$ to R$_4$, respectively, to form a substituted or unsubstituted, mono- or polycyclic, (C5-C25) aromatic ring, whose carbon atom(s) may be replaced with at least one heteroatom selected from nitrogen, oxygen, and sulfur;
R$_5$ represents a substituted or unsubstituted (C6-C30)aryl, or a substituted or unsubstituted (3- to 25-membered) heteroaryl;
the heteroaryl contains at least one heteroatom selected from B, N, O, S, Si, and P;
a to d are as defined in claim 1; and
with the proviso, when a represents 2, two R$_1$ are not fused with the aryl ring to which they are attached to form a carbazole ring.

4. The organic electroluminescent compound according to claim 1, wherein formula 1 is represented by the following formula 3:

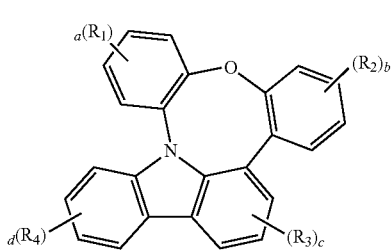

(3)

wherein
R$_1$ to R$_4$, each independently, represent a substituted or unsubstituted (C6-C25)aryl, a substituted or unsubsti-tuted (5- to 25-membered)heteroaryl, or a substituted or unsubstituted di(C6-C25)arylamino; or are linked to adjacent $R_1$ to $R_4$, respectively, to form a substituted or unsubstituted, mono- or polycyclic, (C5-C25) aromatic ring, whose carbon atom(s) may be replaced with at least one heteroatom selected from nitrogen, oxygen, and sulfur;

the heteroaryl contains at least one heteroatom selected from B, N, O, S, Si, and P; and a to d are as defined in claim 1.

5. The organic electroluminescent compound according to claim 1, wherein formula 1 is represented by the following formula 4:

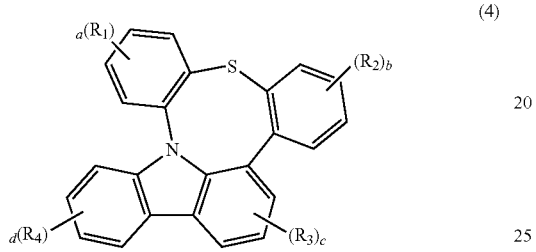

(4)

wherein $R_1$ to $R_4$, each independently, represent a substituted or unsubstituted (C6-C25)aryl, a substituted or unsubstituted (5- to 25-membered)heteroaryl, or a substituted or unsubstituted di(C6-C25)arylamino; or are linked to adjacent $R_1$ to $R_4$, respectively, to form a substituted or unsubstituted, mono- or polycyclic, (C5-C25) aromatic ring, whose carbon atom(s) may be replaced with at least one heteroatom selected from nitrogen, oxygen, and sulfur;

the heteroaryl contains at least one heteroatom selected from B, N, O, S, Si, and P; and a to d are as defined in claim 1.

6. The organic electroluminescent compound according to claim 1, wherein the compound represented by formula 1 is selected from the group consisting of:

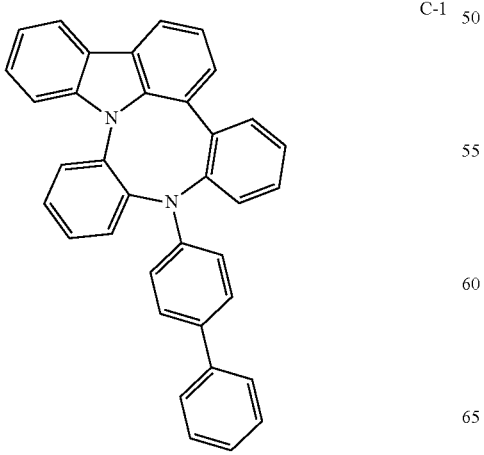

C-1

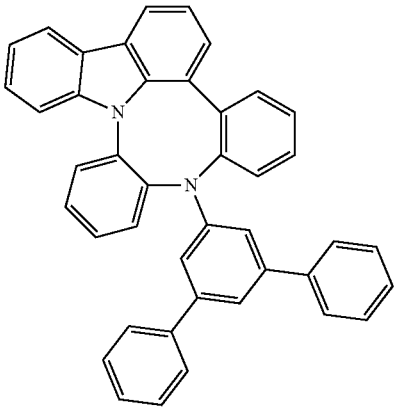

C-2

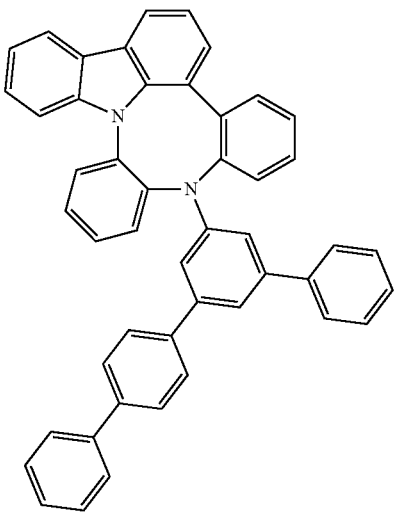

C-3

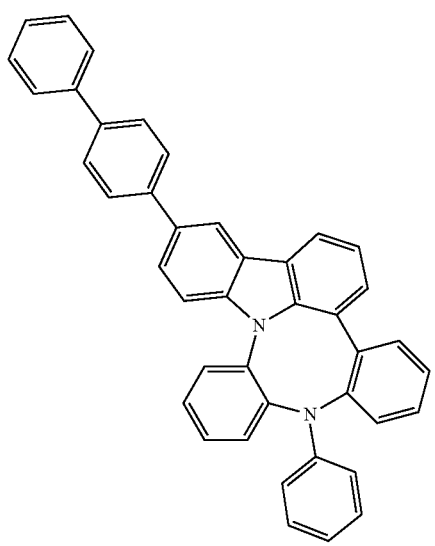

C-4

C-5
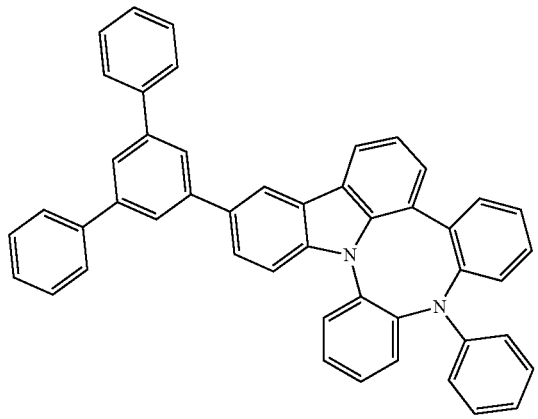
C-8
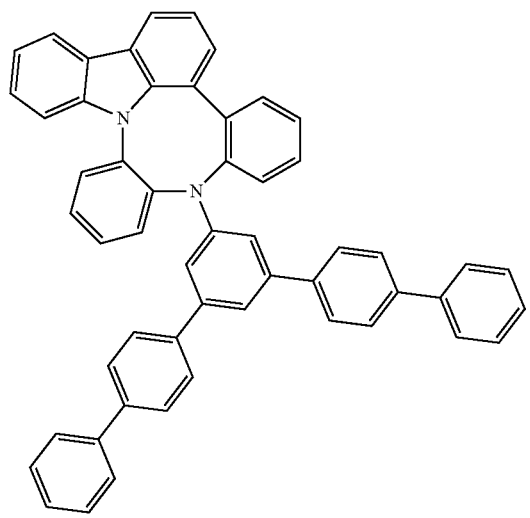
C-6
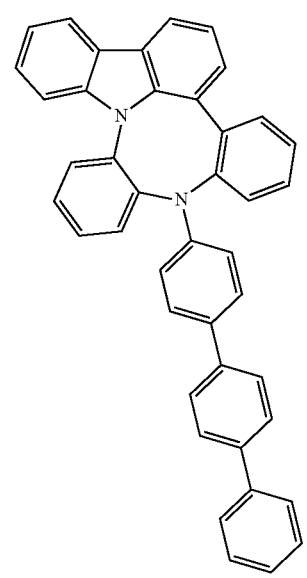
C-9
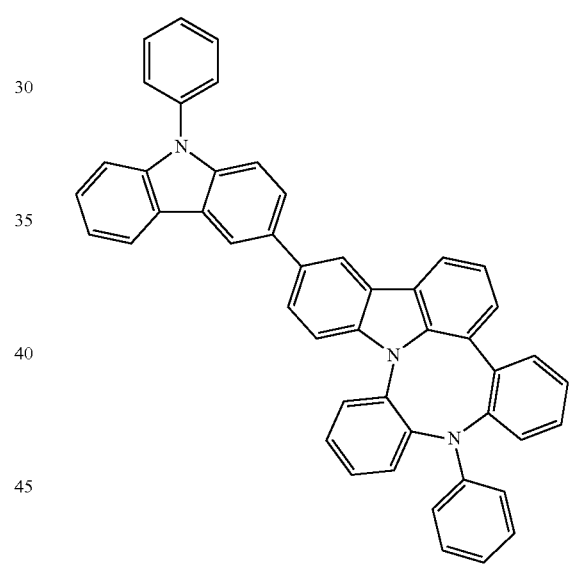
C-7
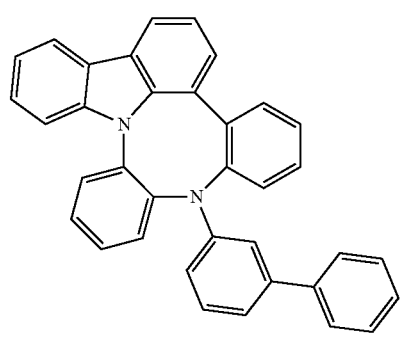
C-10

C-11
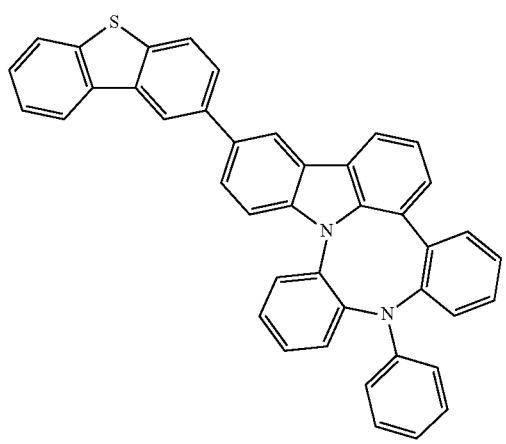
C-12
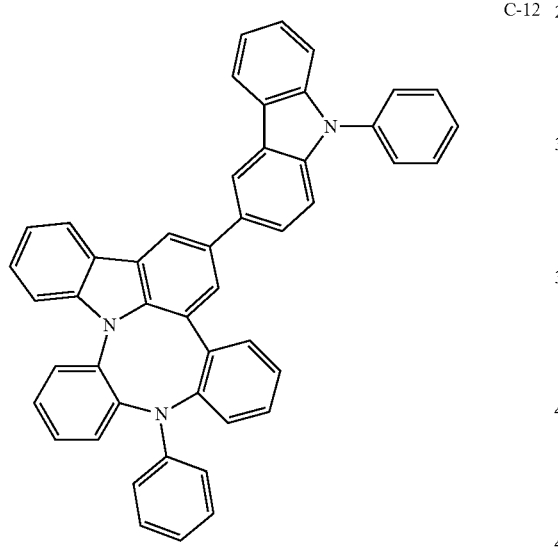
C-13
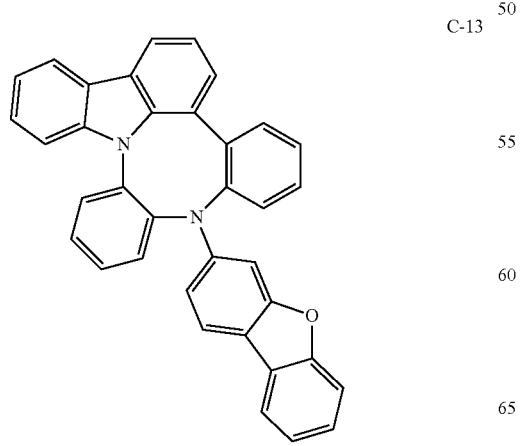
C-14
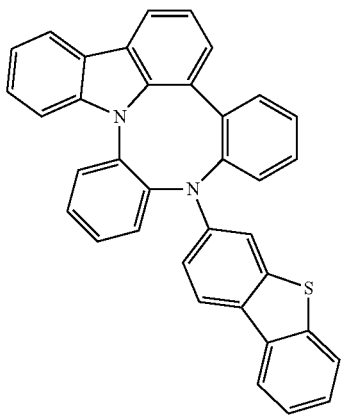
C-15
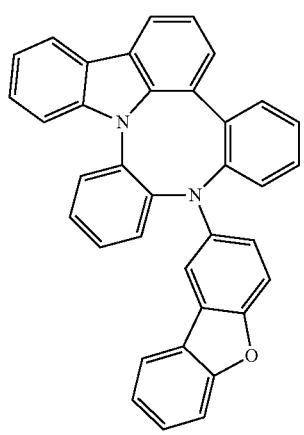
C-16
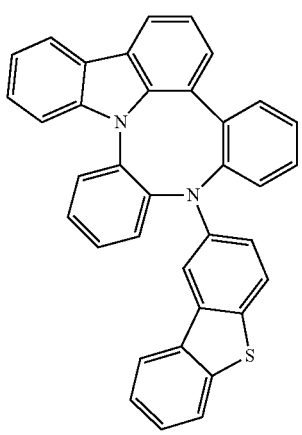

C-17
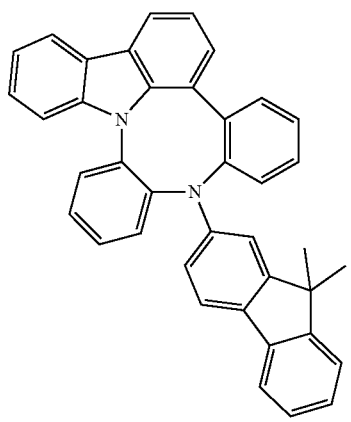
C-18
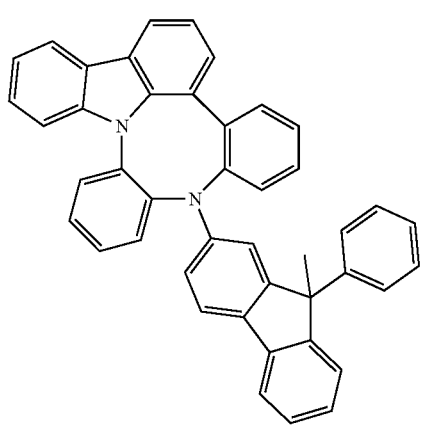
C-19
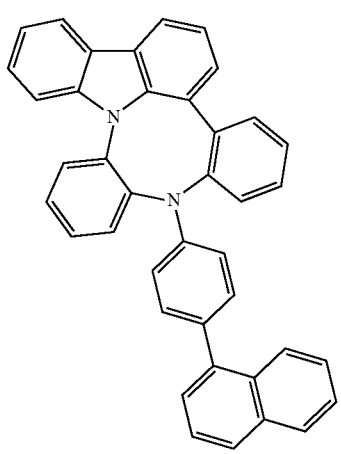
C-20
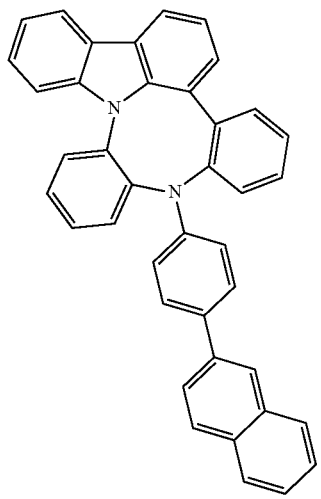
C-21
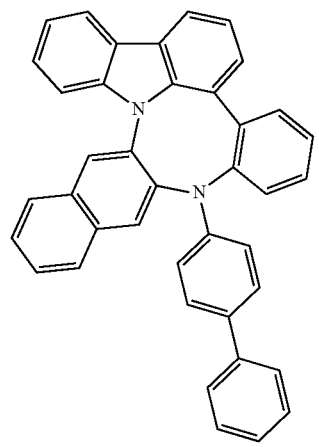
C-22
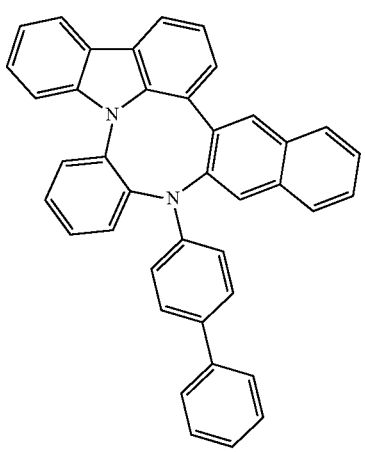

C-23
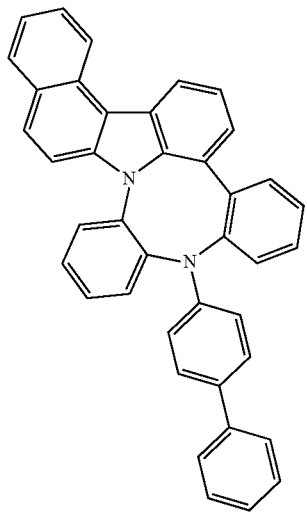
C-26
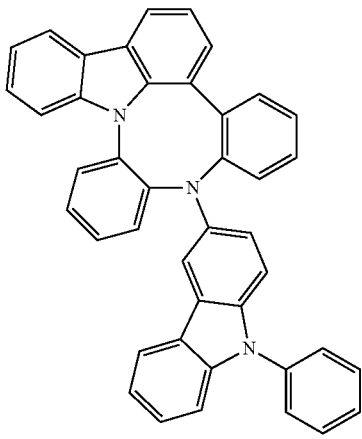
C-24
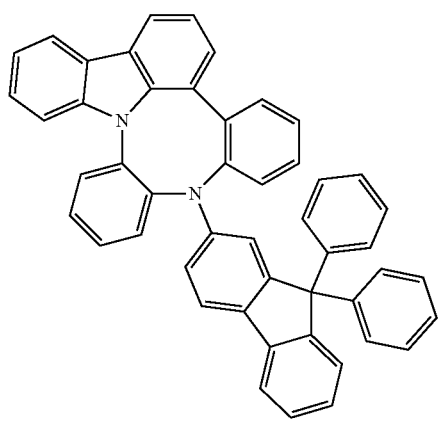
C-27
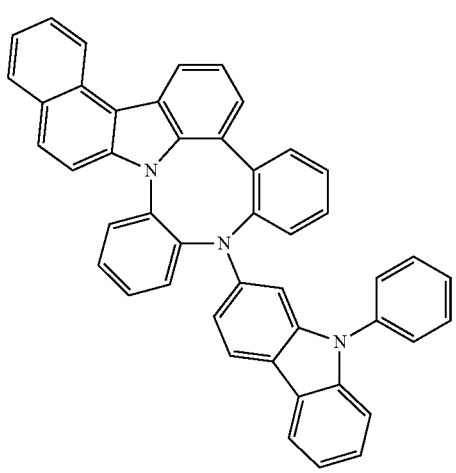
C-25
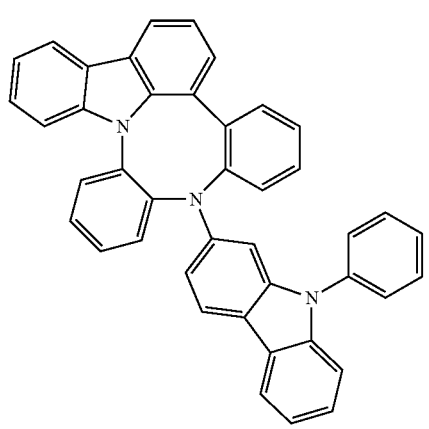
C-28
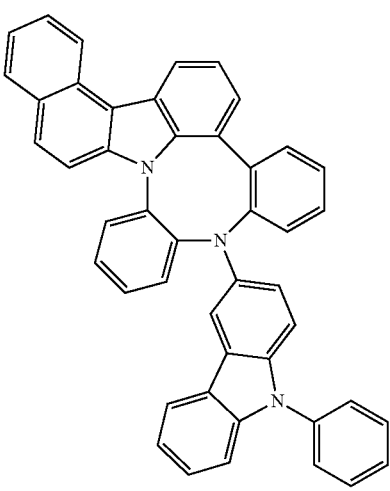

C-29
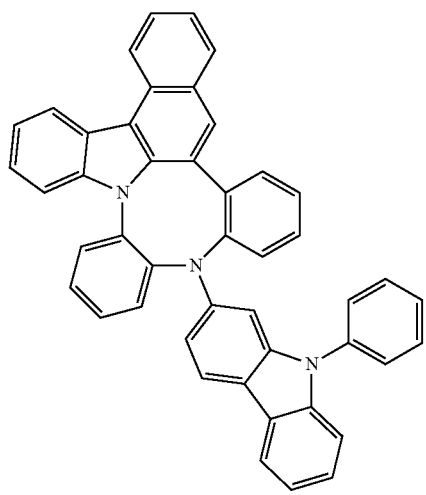
C-30
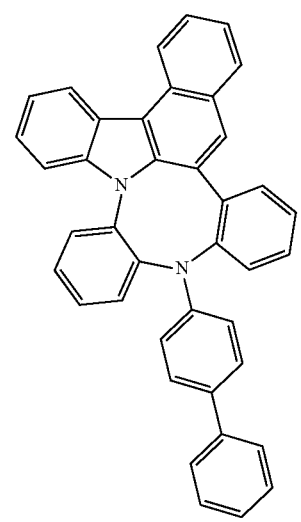
C-31
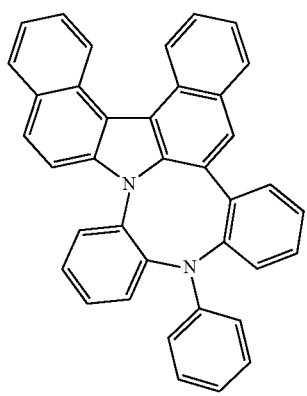
C-32
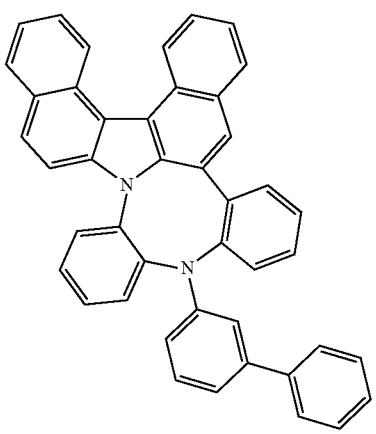
C-33
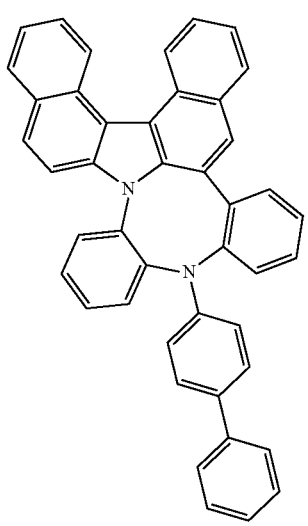
C-34
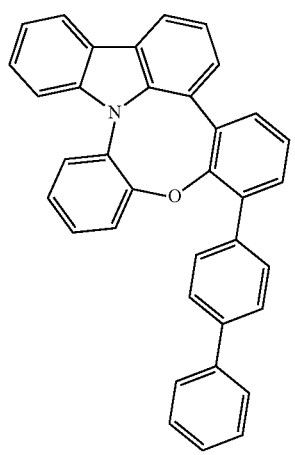

C-35
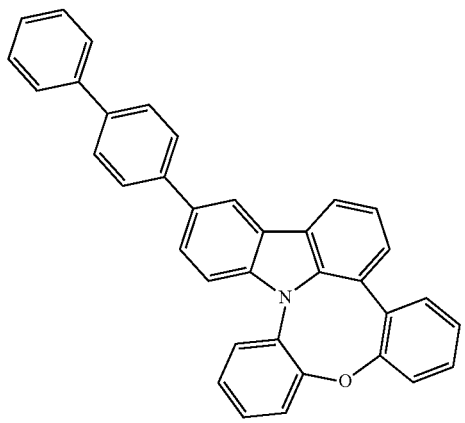
C-36
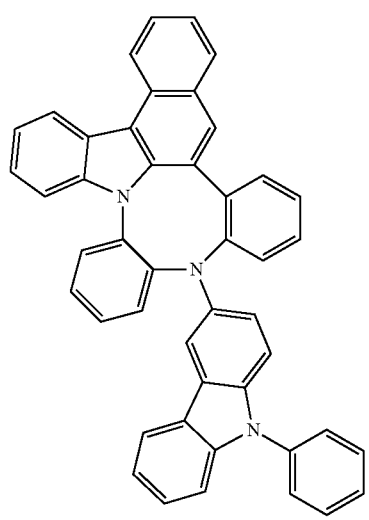
C-37
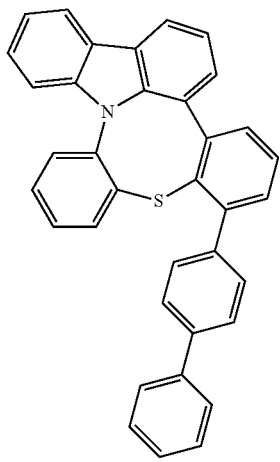
C-38
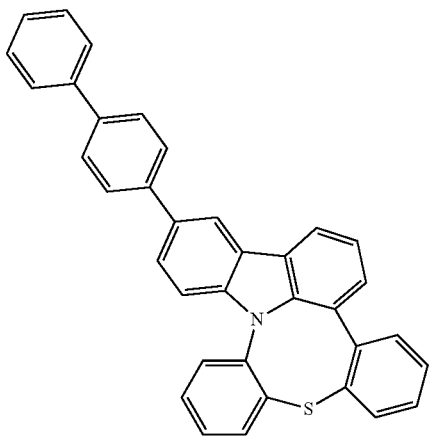
C-39
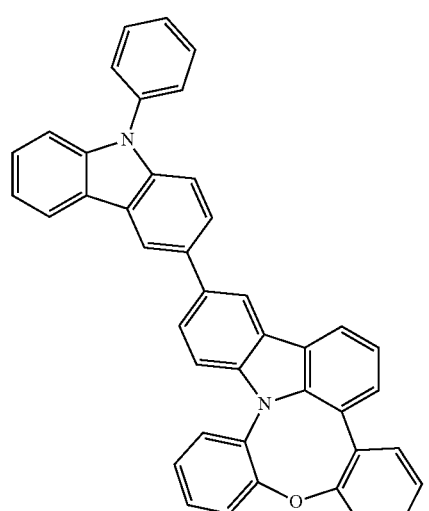
C-40
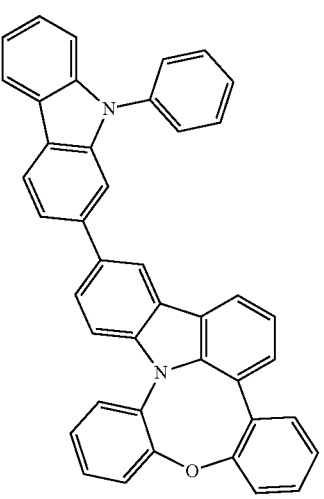

-continued
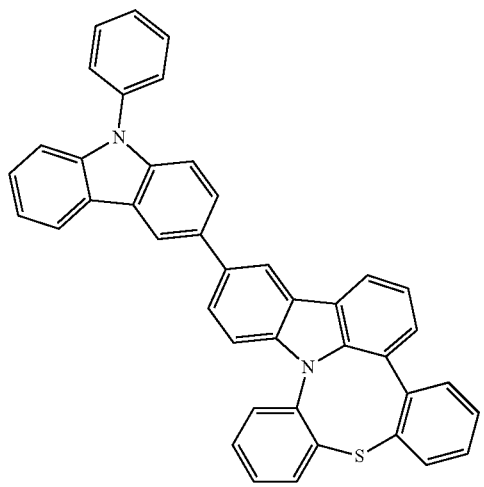
C-41
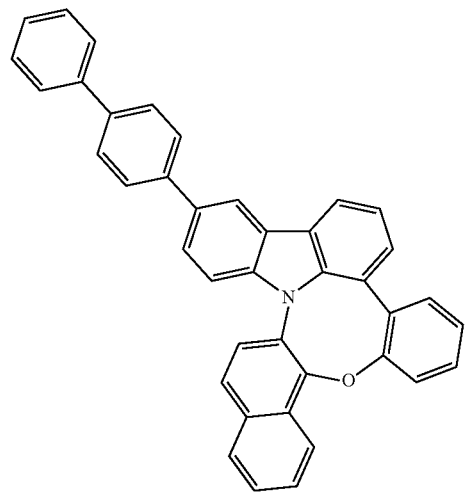
C-44
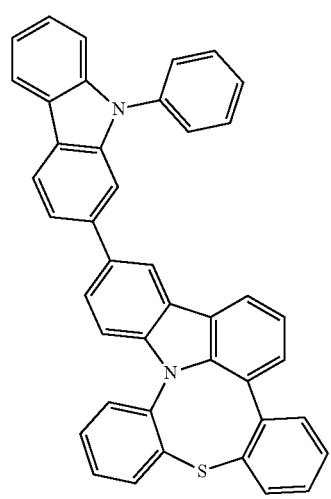
C-42
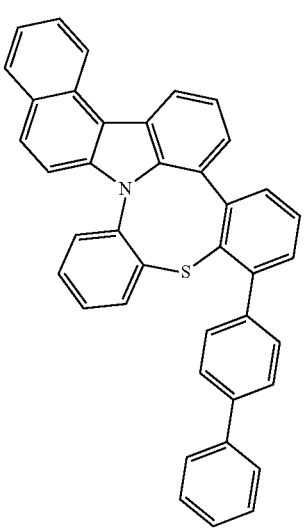
C-45
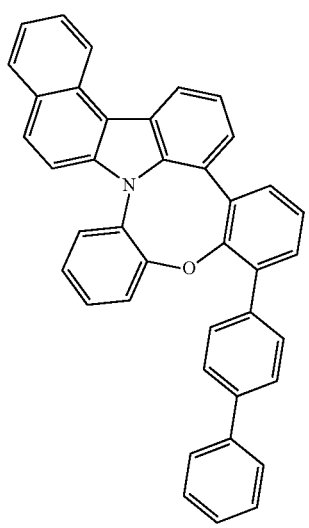
C-43
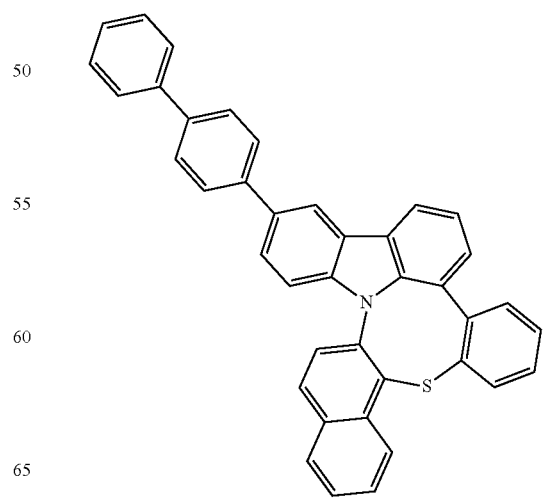
C-46

C-47
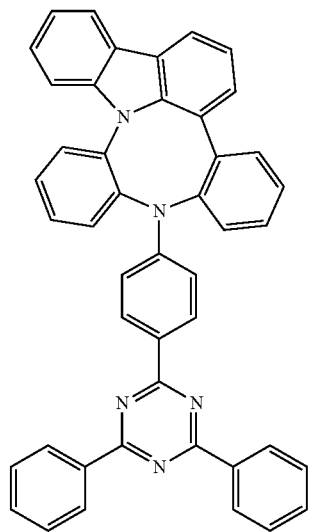
C-50
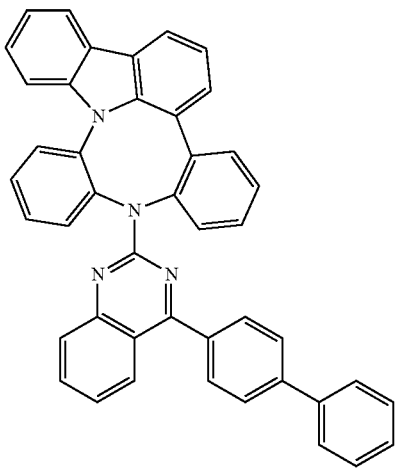
C-48
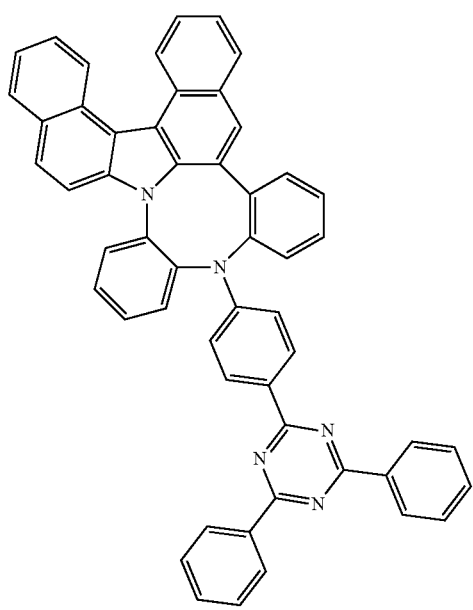
C-51
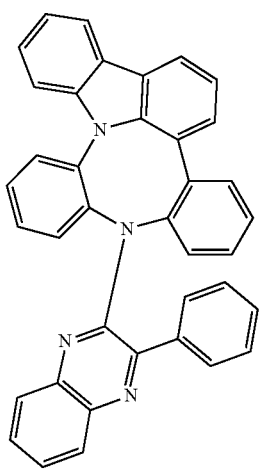
C-49
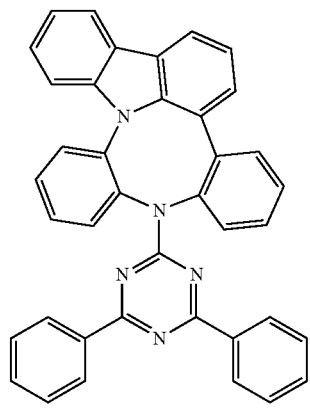
C-52
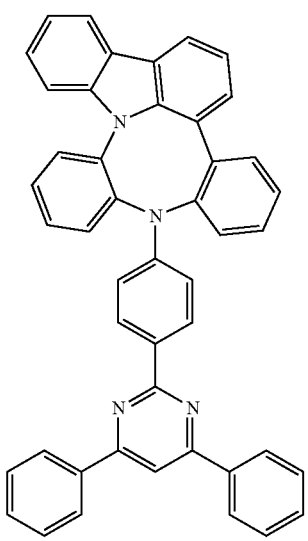

C-53
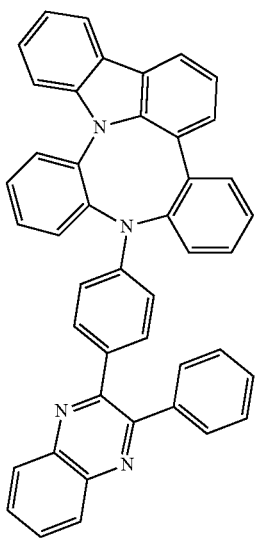
C-54
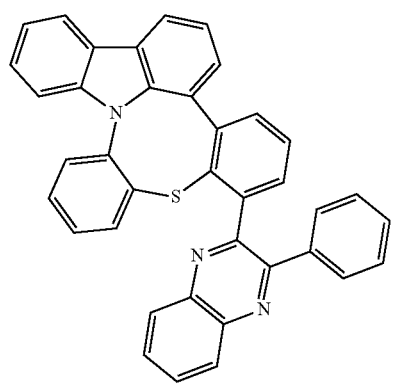
C-55
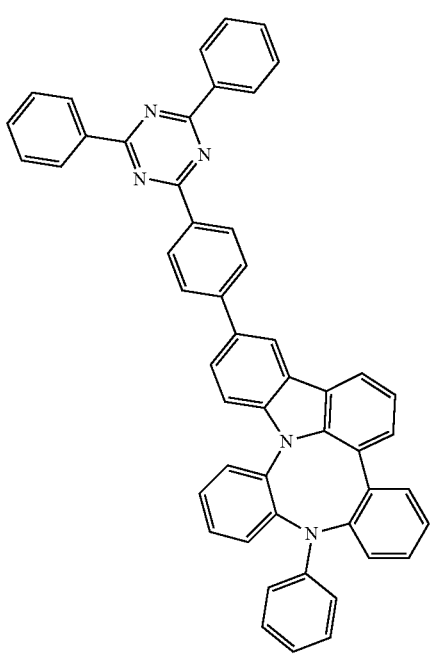
C-56
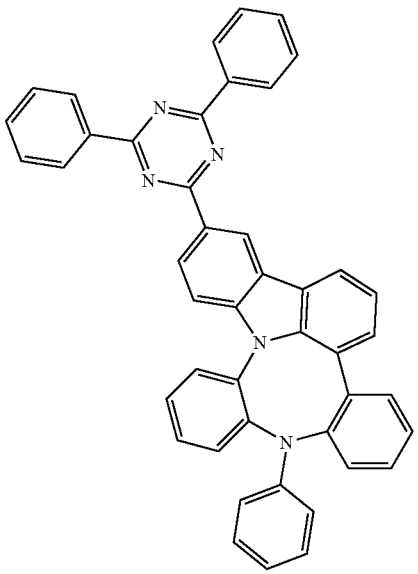
C-57
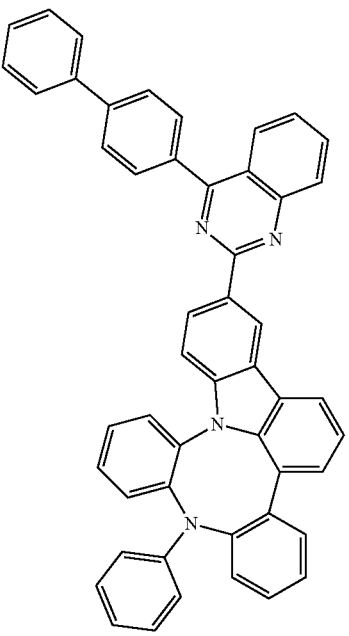

C-58
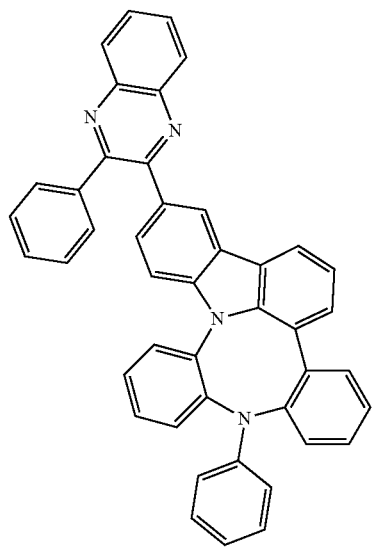
C-60
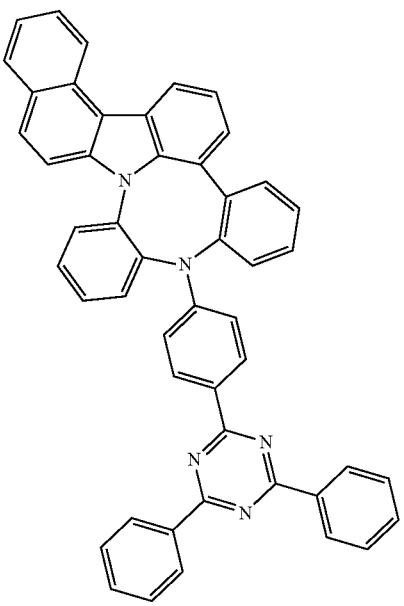
C-59
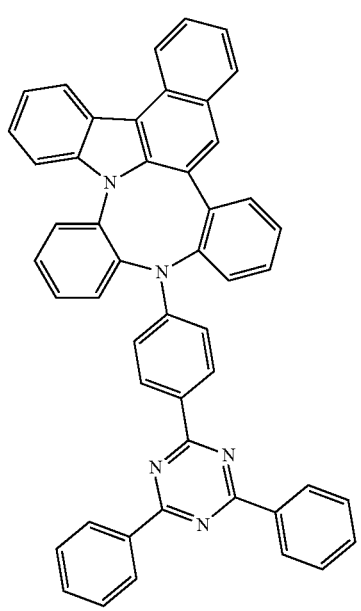
C-61
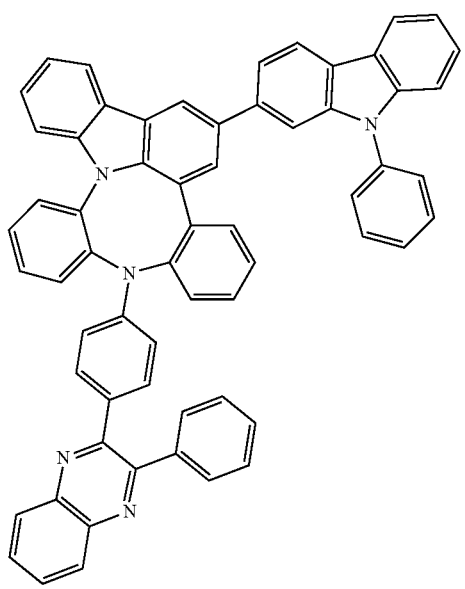

C-62
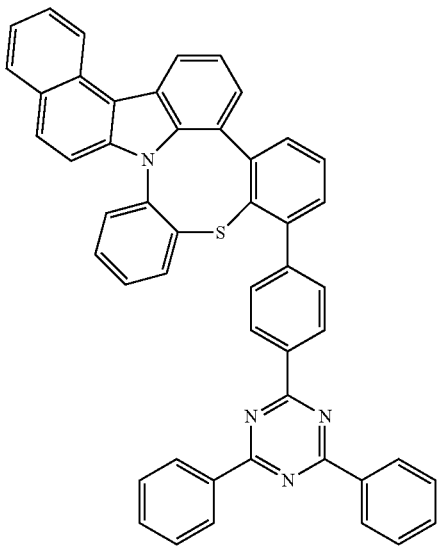
C-63
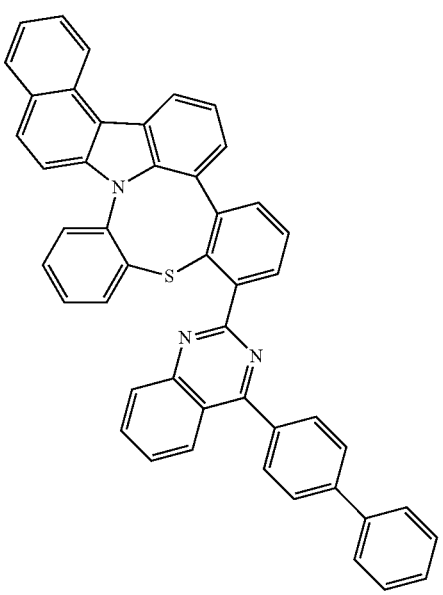
C-64
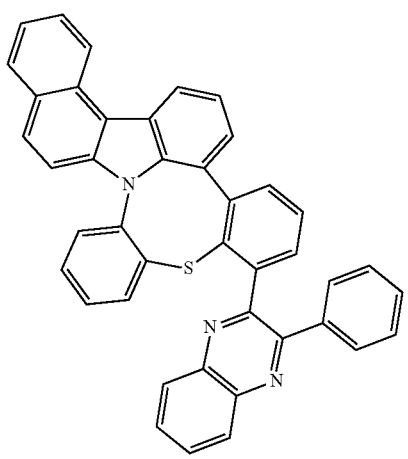
C-65
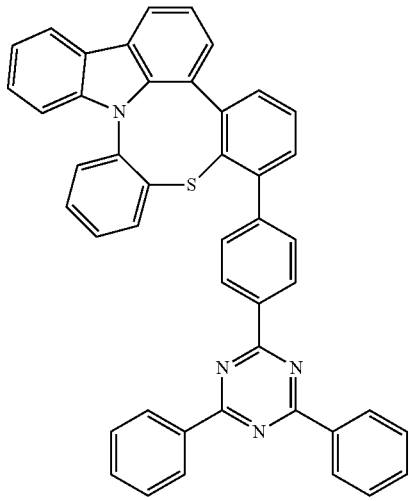
C-66
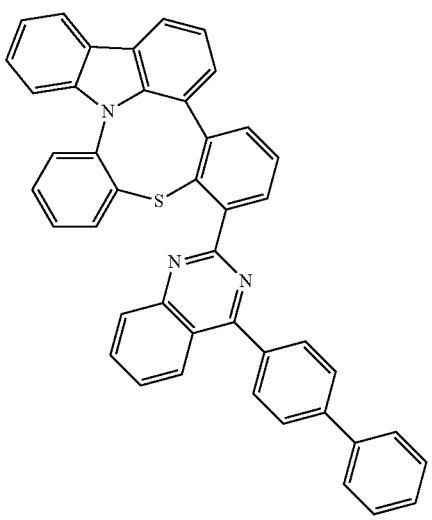
C-67
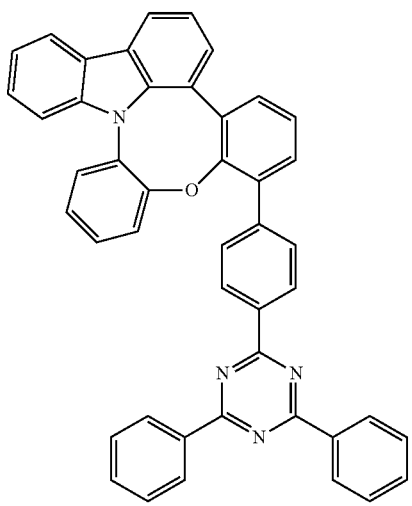

-continued
C-68
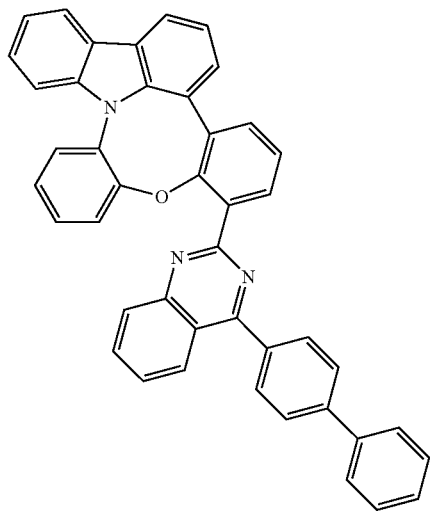
C-69
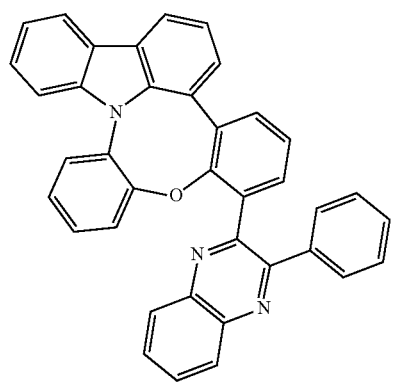
C-70
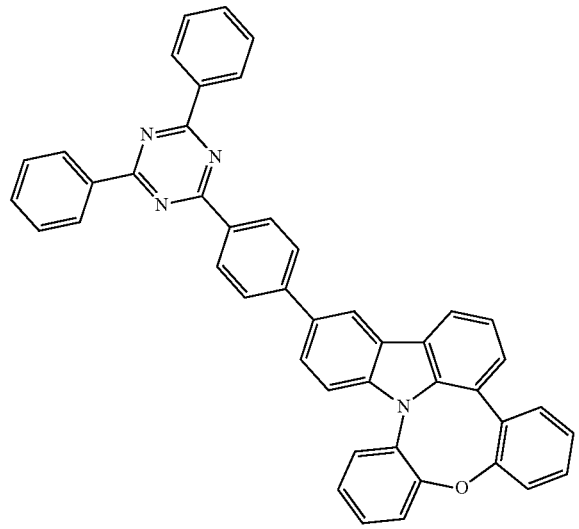
-continued
C-71
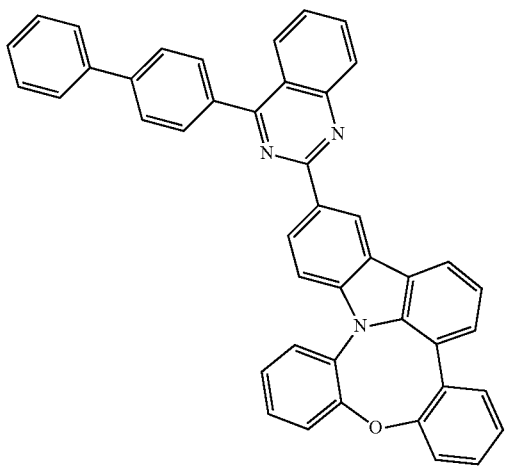
C-72
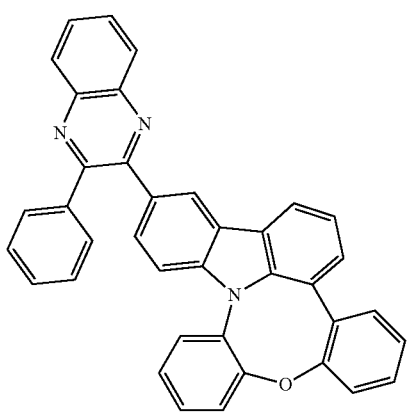
C-73
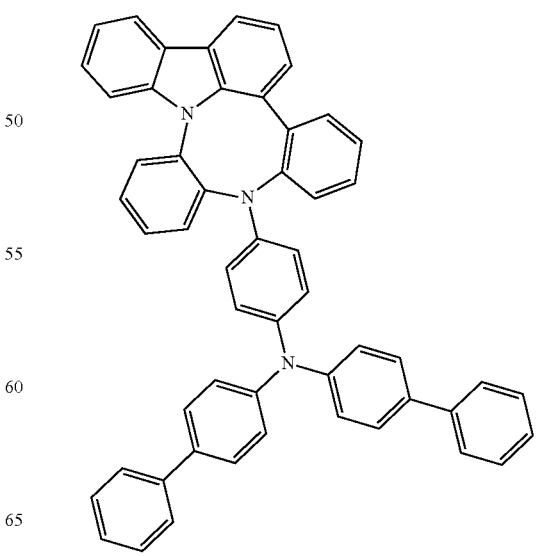

C-74
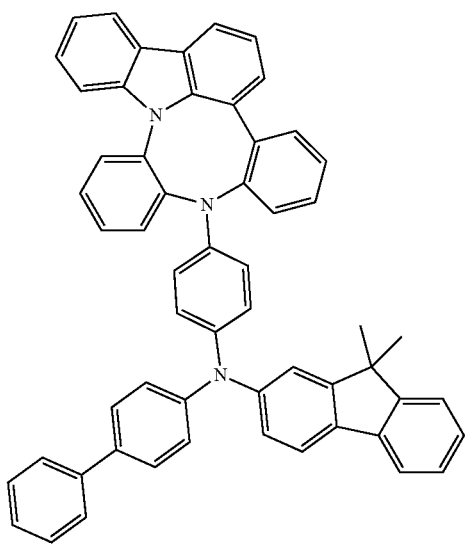
C-75
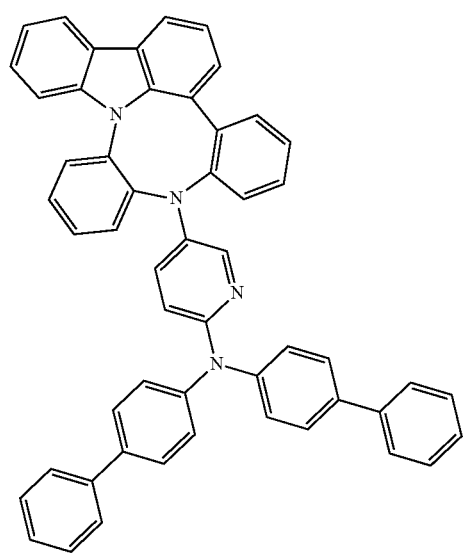
C-76
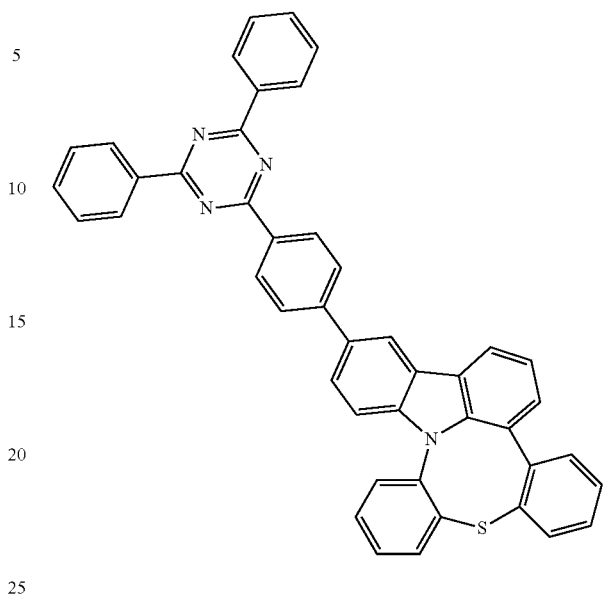
C-77
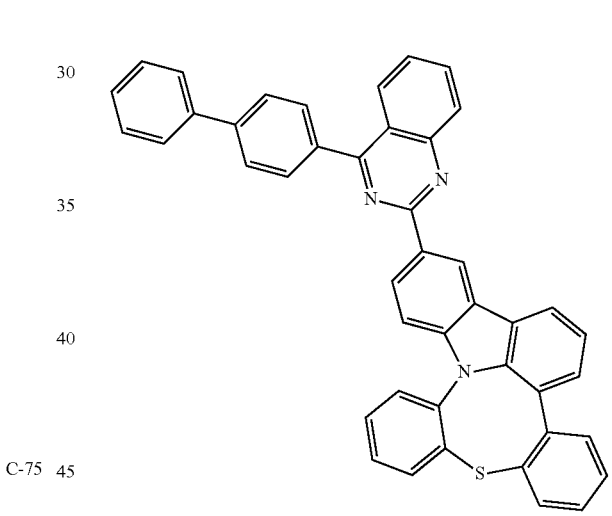
C-78
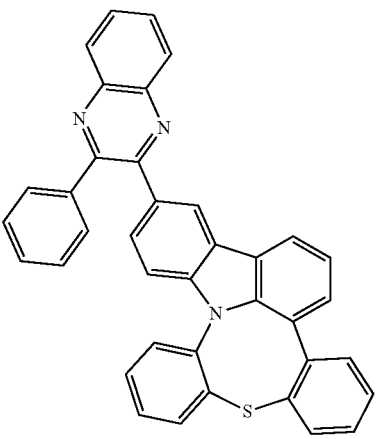

C-79
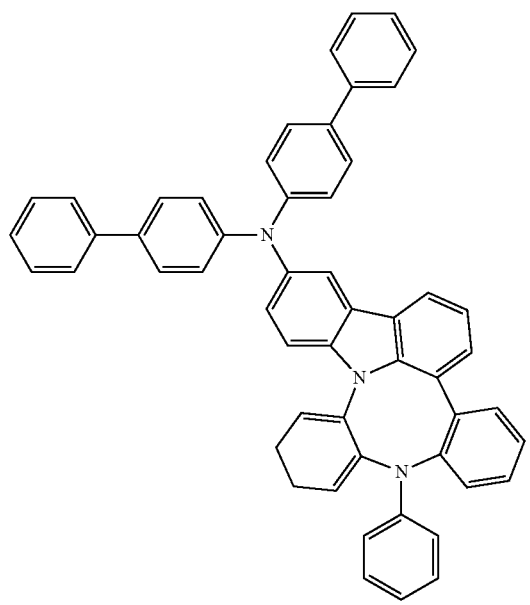
C-81
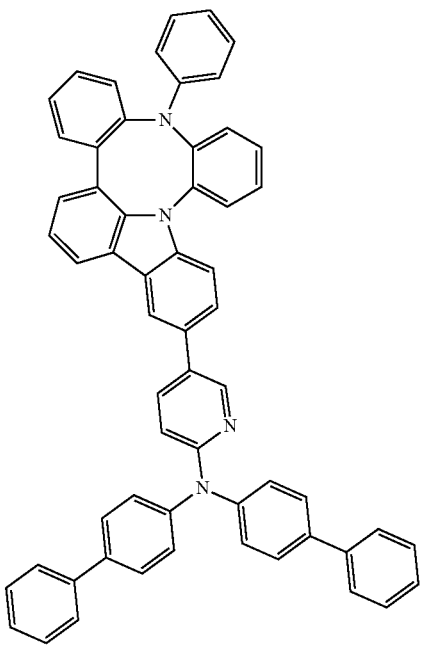
C-80
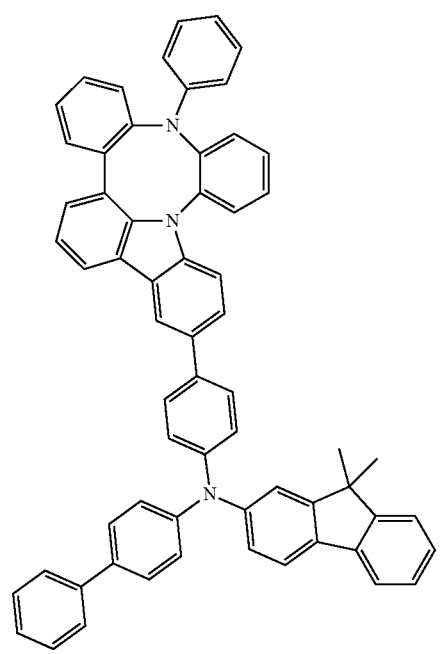
C-82
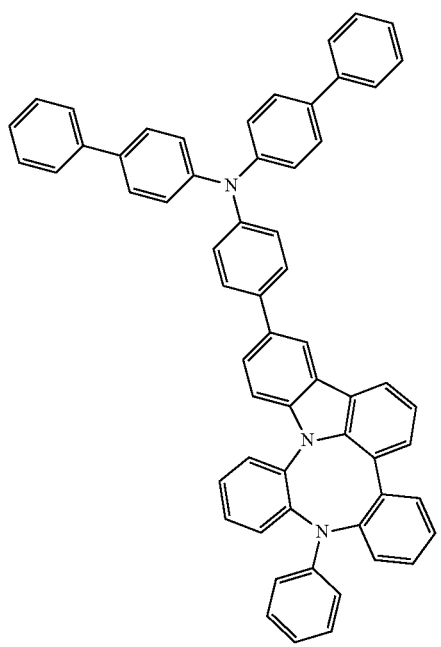

-continued
C-83
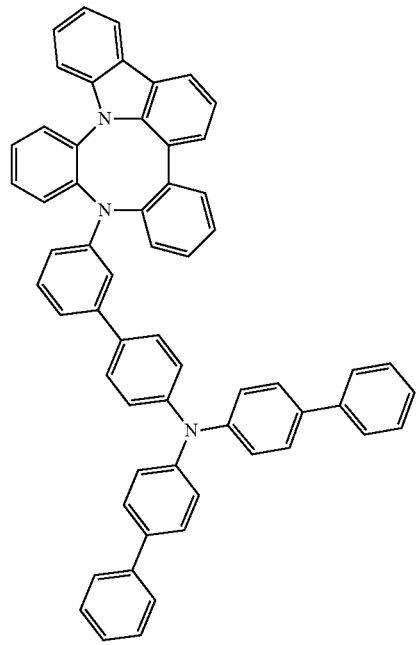
C-84
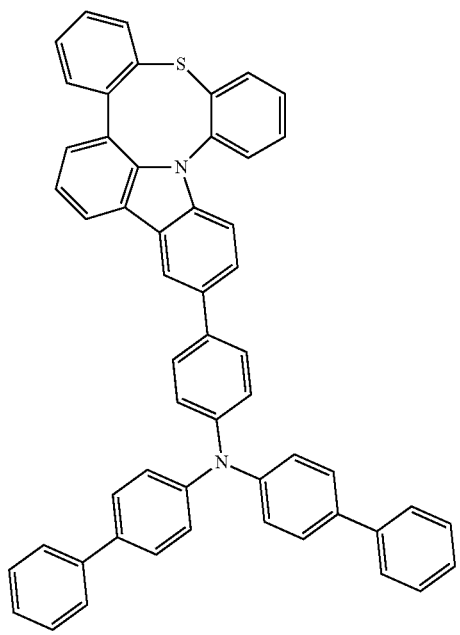
C-85
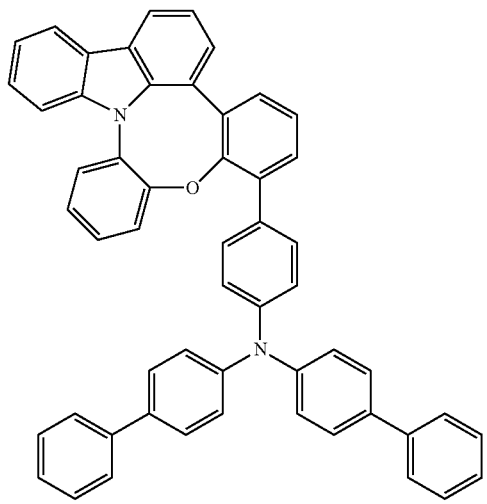
C-86
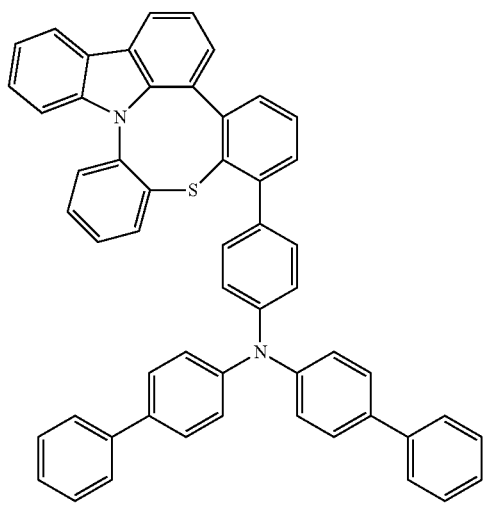

C-87
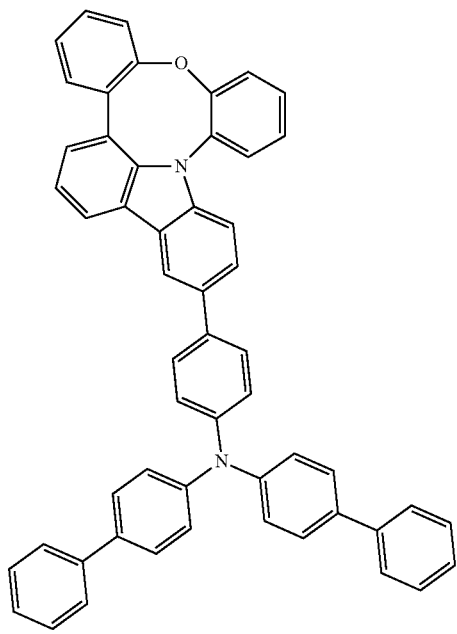
C-89
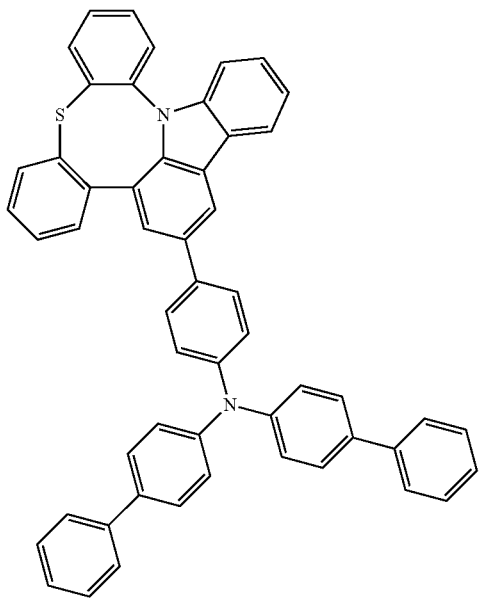
C-88
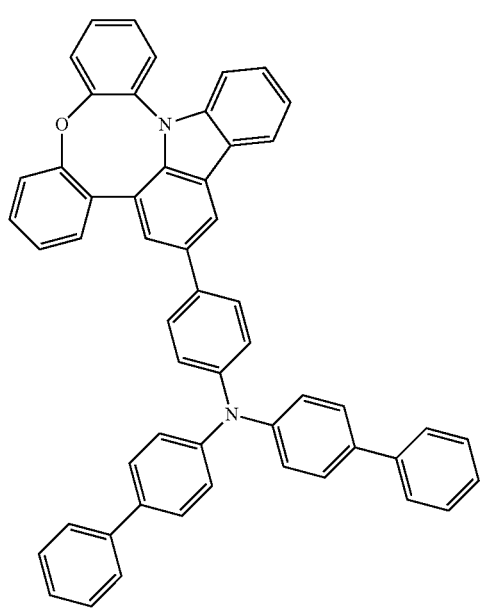
C-90
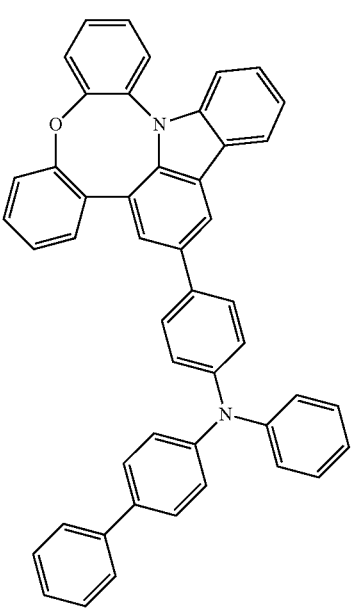

-continued

C-91

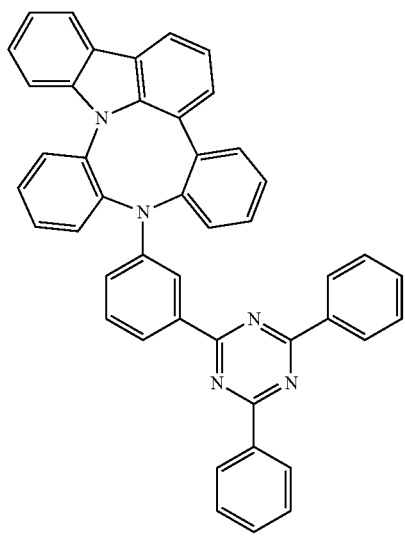

C-92

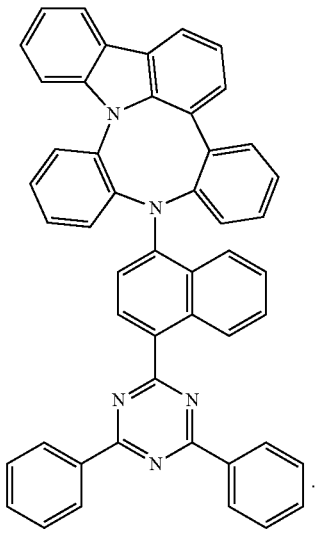

7. An organic electroluminescent material comprising the organic electroluminescent compound according to claim 1.

8. The organic electroluminescent material according to claim 7, wherein the organic electroluminescent material is a host material or an electron buffer material.

9. The organic electroluminescent material according to claim 7, wherein the organic electroluminescent material is a host material comprising at least one of a first host compound and at least one of a second host compound, wherein the first host compound comprises the compound represented by the formula 1, and wherein the second host compound comprises the compound represented by the following formula 5:

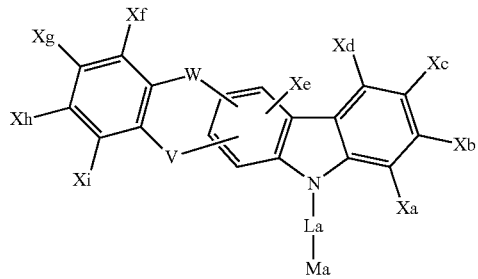

(5)

wherein

Ma represents a substituted or unsubstituted nitrogen-containing (5- to 30-membered)heteroaryl;

La represents a single bond, a substituted or unsubstituted (3- to 30-membered)heteroarylene, or a substituted or unsubstituted (C6-C30)arylene;

one of V and W represents a single bond, and the other of V and W represents any one of $NR_6$, $CR_7R_8$, S and O;

Xa to Xi, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or may be linked to adjacent Xa to Xi, respectively, to form a substituted or unsubstituted mono- or polycyclic (C3-C30), alicyclic or aromatic ring, or the combination thereof, whose carbon atom(s) may be replaced with at least one heteroatom selected from nitrogen, oxygen, and sulfur;

$R_6$ to $R_8$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; and the heteroaryl contains at least one heteroatom selected from B, N, O, S, Si, and P.

10. An organic electroluminescent device comprising the organic electroluminescent compound according to claim 1.

* * * * *